United States Patent [19]
Posner et al.

[11] Patent Number: 6,156,790
[45] Date of Patent: Dec. 5, 2000

[54] C-10 CARBON-SUBSTITUTED ARTEMISININ-LIKE TRIOXANE COMPOUNDS HAVING ANTIMALARIAL, ANTIPROLIFERATIVE AND ANTITUMOR ACTIVITIES

[75] Inventors: Gary H. Posner, Baltimore, Md.; Soon Hyung Woo, Pointe-Claire, Canada; Poonsakdi Ploypradith; Michael H. Parker, both of Baltimore, Md.; Theresa A. Shapiro, Towson, Md.; Qun Y. Zheng, Wayne, N.J.; Christopher Murray; Randall J. Daughenbaugh, both of Longmont, Colo.

[73] Assignees: Hauser, Inc., Boulder, Colo.; Johns Hopkins University, Baltimore, Md.

[21] Appl. No.: 09/001,242

[22] Filed: Dec. 30, 1997

[51] Int. Cl.$^7$ ..................... A61K 31/335; C07D 493/18
[52] U.S. Cl. ..................... 514/450; 514/85; 514/253; 514/338; 544/375; 546/281.7; 549/208; 549/348
[58] Field of Search .................. 549/348, 208; 544/375; 546/281.7; 514/85, 338, 450, 253

[56] References Cited

U.S. PATENT DOCUMENTS

| | | | |
|---|---|---|---|
| 5,225,437 | 7/1993 | Posner et al. | 514/450 |
| 5,225,562 | 7/1993 | McChesney et al. | 549/348 |
| 5,677,468 | 10/1997 | Zheng et al. | 549/348 |

FOREIGN PATENT DOCUMENTS

| | | | |
|---|---|---|---|
| WO 93/08195 | 4/1993 | WIPO | 549/348 |

OTHER PUBLICATIONS

Jung et al, Heterocycles, vol. 45, No. 6, p. 1055–1058, Jun. 1997.
"Conversion of Glycosyl Fluorides into C–Glycosides Using Organoaluminum Regeants. Stereospecific Alkylation at C–6 of a Pyranose Sugar," Gary H. Posner, et al., *Tetrahedron Letters*, vol. 26, No. 15 (1985), pp. 1823–1826.
"A Convenient, One–Step, High–Yield Replacement of an Anomeric Hydroxyl Group by a Fluorine Atom Using DAST. Preparation of Glycosyl Fluorides," Gary H. Posner, et al., *Tetrahedron Letters*, vol. 26, No. 1 (1985), pp. 5–8.
"Synthesis and Antimalarial Activity of Heteroatom–Containing Bicyclic Endoperoxides," Gary H. Posner, et al., *Tetrahedron*, vol. 53, No. 1 (1997), pp. 37–50.
"Synthesis and Antimalarial Activities of 12β–Allyldcoxoartemisinin and Its Derivatives," Yu Ming Pu, et al., *J. Med Chem.*, vol. 38 (1995), pp. 613–616.
"Synthesis and Cytotoxicity of Novel Artemisinin Analogs," Mankil Jung, *Bioorganic & Medicinal Chemistry Letters*, vol. 7, No. 8 (1997), pp. 1091–1094.
"Trioxane Dimers Have Potent Antimalarial, Antiproliferative and Antitumor Activities in Vitro," Gary H. Posner, et al., *Bioorganic & Medicinal Chemistry*, vol. 5, No. 7, (1997), pp. 1257–1265.

"A Concise and Stereoselective Synthesis of (+)–12–n–Butyldeoxoartemisinin," Mankil Jung, et al., *Synleu*, (1990), pp. 743–744.
"Phosphonate Analogs of Carbocyclic Nucleotides," Robert D. Elliott, et al., *J. Med. Chem.*, vol. 37, (1994), pp. 739–744.
"Carbocyclic Arabinofuranosyladenine (Cyclaradine): Efficacy Against Genital Herpes in Guinea Pigs," Robert Vince, et al., *Science*, vol. 221, (1983), pp. 1405–1406.
"An Unusual Acid–Catalyzed Rearrangement of 1,2,4–Trioxanes," Yu–Ming Pu, et al., *Heterocycles*, vol. 36, No. 9, (1993), pp. 2099–2107.
"Efficient Preparation of Novel Qinghaosu (Artemisinin) Derivatives: Conversion of Qinghao (Artemisinic) Acid into Deoxoqinghaosu Derivatives and 5–Carba–4–deoxoartesunic Acid," Richard K. Haynes, et al., *Synlen*, (1992), pp. 481–483.
"Artemishinin and the Antimalarial Endoperoxides: from Herbal Remedy to Targeted Chemotherapy," S.R.Meshnick, et al., *Microbiological Reviews*, vol. 60, No. 2, (1996), pp. 301–315.
"Some Aspects of the Chemistry and Biological Activity of Artemisinin and Related Antimalarials," Syed S. Zaman, et al., *Heterocycles*, vol. 32, No. 8, (1991), pp. 1593–1638.
"Transactions of the Royal society of Tropical Medicine and Hygiene," vol. 88:1, (Jun. 1994), pp. S1/1–S1/65.
"Extraordinarily Potent Antimalarial Compounds: New, Structurally, Simple, Easily Synthesized, Tricyclic 1,2, 4–Trioxanes," Gary H. Posner, et al., *J. Med. Chem.*, vol. 35, No. 13, (1992), pp. 2459–2467.
"Artemisinin (Qinghaosu): A New Type of Antimalarial Drug," Anthony R. Butler, et al., (1992), pp. 85–90, Chem. Soc. Rev.

(List continued on next page.)

*Primary Examiner*—Bernard Dentz
*Attorney, Agent, or Firm*—Hogan & Hartson L.L.P.; Steven C. Petersen; Sarah O'Rourke

[57] ABSTRACT

The present invention provides a two-step procedure for the replacement of the pyranose anomeric 10-OH group in dihydroartemisinin by a variety of carbon nucleophiles, resulting in the novel C-10 carbon-substituted trioxanes of structure:

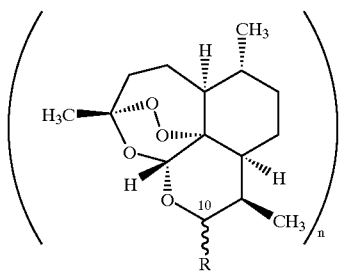

wherein, when n is 1, R is selected from a group of unsubstituted or substituted aryls, heteroaryls, polyethylene glycol, acetylenics, or benzoylmethylenes, or alkanoylmethylenes; or when n is 2, R is selected from a group of unsubstituted or substituted aryls, heteroaryls, polyethylene glycol, alkenyls, alkyls, diketones or bis-acetylenes.

30 Claims, 19 Drawing Sheets

OTHER PUBLICATIONS

"Cytotoxicity of Artemisinin–Related Endoperoxides to Ehrlich Ascites Tumor Cells," Herman J. Woerdenbag, et al., *Journal of Natural Products,* vol. 56, No. 6, (1993), pp. 849–856.

"Qinghaosu (Artemisinin): An Antimalarial Drug from China," Daniel L. Klayman, Science, vol. 228 (1985) p. 1049–1055.

"Synthesis of Novel Ring Contracted Artemisinin Derivative," B. Venugopalan, et al., *Bioorganic & Medicinal Chemistry Letters,* vol. 4, No. 5 (1994), pp. 751–752.

C-10 CARBON-SUBSTITUTED ARTEMISININ-LIKE TRIOXANE COMPOUNDS HAVING ANTIMALARIAL, ANTIPROLIFERATIVE AND ANTITUMOR ACTIVITIES

CROSS-REFERENCE DISCLOSURE DOCUMENTS

This patent application references Disclosure Document entitled "A Novel Class of 12-C Artemisinin Dimers," No.: 392,815, filed Feb. 23, 1996.

CONTRACTUAL ORIGIN OF THE INVENTION

The study was supported in-part by National Institutes of Health grant AI 34885 (to G.H.P.) and NCRR OPTD-GCRC RR00722 (to T.A.S.) and joint inventors G.H.P., T.A.S., S.H.W., M.H.P. and P.P., have assigned their rights to the Johns Hopkins University.

BACKGROUND OF THE INVENTION

1. Field of the Invention

The present invention relates to a direct two-step procedure for the replacement of the pyranose anomeric 10-OH group in dihydroartemisinin by various carbon nucleophiles without the destruction of the trioxane peroxide bond. The present invention further relates to the formation of monomeric and dimeric C-10 carbon-substituted (rather than oxygen substituted) derivative of the trioxane 10-deoxoartemisinin which demonstrate potent and potentially therapeutically valuable antimalarial, and antiproliferative and antitumour activities.

2. Description of the State of Art

Each year approximately 200–300 million people experience a malarial illness and over 1 million individuals die. In patents with severe and complicated disease, the mortality rate is between 20 and 50%.

Plasmodium is the genus of protozoan parasites which is responsible for all cases of malaria and *Plasmodium falciparum* is the species of parasite that is responsible for the vast majority of fatal malaria infections. Malaria has traditionally been treated with quinolines such as chloroquine, quinine, mefloquine, and primaquine and with antifolates such as sulfadoxine-pyrimethamine. Unfortunately, most *P. falciparum* strains have now become resistant to chloroquine, and some, such as those in Southeast Asia, have also developed resistance to mefloquine and halofantrine; multidrug resistance is developing in Africa also.

The endoperoxides are a promising class of antimalarial drugs which may meet the dual challenges posed by drug-resistant parasites and the rapid progression of malarial illness. The first generation endoperoxides include artemisinin and several synthetic derivatives, discussed in further detail below.

*Artemisia annua L.,* also known as qinghao or sweet wormwood, is a pervasive weed that has been used for many centuries in Chinese traditional medicine as a treatment for fever and malaria. Its earliest mention, for use in hemorrhoids, occurs in the *Recipes for 52 Kinds of Diseases* found in the Mawangdui Han dynasty tomb dating from 168 B.C. Nearly five hundred years later Ge Hong wrote the *Zhou Hou Bei Ji Fang* (Handbook of Prescriptions for Emergency Treatments) in which he advised that a water extract of qinghao was effective at reducing fevers. In 1596, Li Shizhen, the famous herbalist, wrote that chills and fever of malaria can be combated by qinghao preparations.

Finally, in 1972, Chinese chemists isolated from the leafy portions of the plant the substance responsible for its reputed medicinal action. This crystalline compound, called qinghaosu, also referred to as QHS or artemisinin, is a sesquiterpene lactone with an internal peroxide linkage.

Artemisinin is a member of the amorphane subgroup of cadinenes and has the following structure (I):

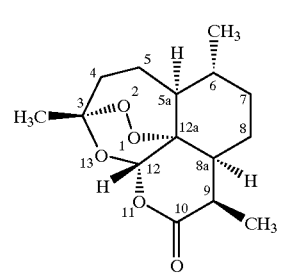

Artemisinin or QHS was the subject of a 1979 study conducted by the Qinghaosu Antimalarial Coordinating Research Group involving the treatment of 2099 cases of malaria (*P. vivax* and *P. falciparum* in a ratio of about 3:1) with different dosage forms of QHS, leading to the clinical cure of all patients. See, Qinghaosu Antimalarial Coordinating Research Group, *Chin. Med. J.,* 92:811 (1979). Since the time artemisinin has been used successfully in many thousand malaria patients throughout the world including those infected with both chloroquine-sensitive and chloroquine-resistant strains of *P. falciparum*. Assay of artemisinin against *P. falciparum* in vitro revealed that its potency is comparable to that of chloroquine in two Hanian strains (Z. Ye, et al., *J. Trad. Chin. Med.,* 3:95 (1983)) and of mefloquine in the Camp (chloroquine-susceptible) and Smith (chloroquine-resistant) strains, D. L. Klayman, et al., *J. Nat. Prod.,* 47:715 (1984).

Although artemisinin is effective at suppressing the parasitemias of *P. vivax* and *P. falciparum*, the problems encountered with recrudescence, and the compound's insolubility in water, led scientists to modify artemisinin chemically, a difficult task because of the chemical reactivity of the peroxide linkage which is believed to be an essential moiety for antimalarial activity.

Reduction of artemisinin in the presence of sodium borohydride results in the production of dihydroartemisinin (II-1) or DHQHS, (illustrated in structure II below), in which the lactone group is converted to a lactol (hemiacetal) function, with properties similar to artemisinin. Artemisinin in methanol is reduced with sodium borohydride to an equilibrium mixture of α- and β-isomers of dihydroartemisinin. The yield under controlled conditions is 79% (artemisinin, 0.85M with NaBH$_4$ 6:34M, 7:5 equivalents in methanol, 12 L at 0–5° C. for about 3 hours followed by quenching with acetic acid to neutrality at 0–5° C. and dilution with water to precipitate dihydroartemisinin), A. Brossi, et al., *Journal of Medicinal Chemistry,* 31:645–650 (1988). Using dihydroartemisinin as a starting compound a large number of other derivatives, such as:

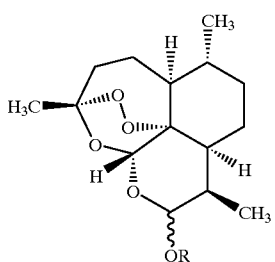

1 R = H
2 R = CH₃
3 R = CH₂CH₃
4 R = COCH₂CH₂COONa
5 R = CH₂C₆H₄COOH
6 R = CH₂CC₆H₄COONa
7 R =

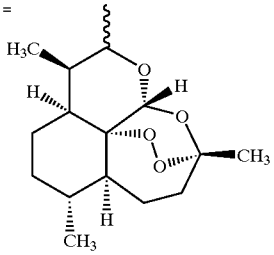

artemether (compound II-2), arteether (II-3), sodium artesunate (II-4), artelinic acid (II-5), sodium artelinate (II-6), dihydroartemisinin condensation by-product (II-7) and the olefinic compound, structure III:

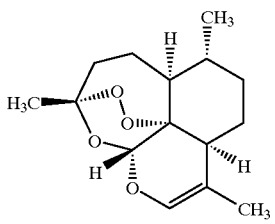

have been produced.

Artemether (II-2) is produced by reacting β-dihydroartemisinin with boron trifluoride (BF₃) etherate or HCl in methanol:benzene (1:2) at room temperature. A mixture of β- and α-artemether (70:30) is obtained, from which the former is isolated by column chromatography and recrystallized from hexane or methanol, R. Haynes, *Transactions of the Royal Society of Tropical Medicine and Hygiene,* 88(1): S1/23-S1/26 (1994). For arteether (II-3), (Brossi, et al., 1988), the α-isomer is equilibrated (epimerized) to the β-isomer in ethanol:benzene mixture containing BF₃ etherate. Treatment of dihydroartemisinin with an unspecified dehydrating agent yields both the olefinic compound, (III), and the dihydroartemisinin condensation by-product (II-7), formed on addition of dihydroartemisinin to (III), M. Cao, et al., *Chem. Abstr.,* 100:34720k (1984). Until recently, the secondary hydroxy group in dihydroartemisinin (II-1) provided the only site in an active artemisinin-related compound that had been used for derivatization. See B. Venugopalan, "Synthesis of a Novel Ring Contracted Artemisinin Derivative," *Bioorganic & Medicinal Chemistry Letters,* 4(5):751–752 (1994).

The potency of various artemisinin-derivatives in comparison to artemisinin as a function of the concentration at which the parasitemia is 90 percent suppressed (SD₉₀) was reported by D. L. Klayman, "Qinghaosu (Artemisinin): An Antimalarial Drug from China," *Science* 228:1049–1055 (1985). Dr. Klayman reported that the olefinic compound III is inactive against *P. berghei*-infected mice, whereas the dihydroartemisinin condensation by-product (II-7) has an SD₉₀ of 10 mg/Kg in *P. berghei*-infected mice. Thus, the dihydroartemisinin ether dimer proved to be less potent than artemisinin, which has an SD₉₀ of 6.20 mg/Kg. Following, in order of their overall antimalarial efficacy, are the three types of derivatives of dihydroartemisinin (II-1) that have been produced: (artemisinin)<ethers (II, R=alkyl)<esters [II, R=C(=O)-alkyl or -aryl]<carbonates [II, R=C(=O)O-alkyl or -aryl].

Other rational design of structurally simpler analogs of artemisinin has led to the synthesis of various trioxanes, some of which possess excellent antimalarial activity. Posner, G. H., et al., reported the chemistry and biology of a series of new structurally simple, easily, prepared, racemic 1,2,4-trioxanes (disclosed in U.S. Pat. No. 5,225,437 and incorporated herein by reference) that are tricyclic (lacking the lactone ring present in tetracyclic artemisinin I) and that are derivatives of trioxane alcohol IV:

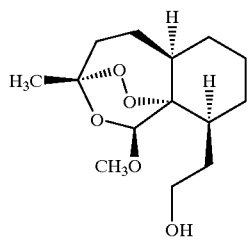

having the relative stereochemistry shown above. Especially attractive features of trioxane alcohol IV are the following: (1) is straightforward and easy preparation from cheap and readily available starting materials, (2) its availability of gram scale, and (3) its easy one-step conversion, using standard chemical transformations, into alcohol derivatives such as esters and ethers, without destruction of the crucial trioxane framework. See, Posner, G. H. et al., *J. Med. Chem.,* 35:2459–2467 (1992), incorporated herein by reference. The complete chemical synthesis of artemisinin and a variety of other derivatives is reviewed by Sharma, R. P., et al., *Heterocycles,* 32(8):1593–1638 (1991), and is incorporated herein by reference.

Metabolic studies by Baker, et al., demonstrated that β-arteether (II-3), one of the antimalarial derivatives discussed previously, was rapidly converted by rat liver microsomes into dihydroartemisinin (II-1). See Baker, J. K., et al., *Biol. Mass. Spect.,* 20:609–628 (1991). This finding and the fact that the most effective artemisinin derivatives against malaria have been ethers or esters of (II-1) suggest that they were prodrugs for (II-1). The controlled slow formation of (II-1), however, is not desirable in view of its short half-life in plasma (less than two hours) and relatively high toxicity.

The successful synthesis of anticancer and antiviral drugs by replacing a carbon-nitrogen bond in nucleosides by a carbon-carbon bond (C-nucleosides) prompted the preparation of several 10-alkyldeoxoartemisinins, V:

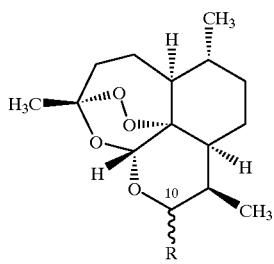

wherein R is 1-allyl, propyl, methyl, or ethyl. Typically, these syntheses involved five or six steps and the reported yields were only about 12 percent. See, Jung, M., et al., *Synlett.*, 743–744 (1990); and Haynes, R. K., et al., *Synlett.*, 481–484 (1992).

Over the past thirty years only a few drugs isolated from higher plants have yielded clinical agents, the outstanding examples being vinblastine and vincristine from the Madagascan periwinkle, *Catharnathus roseus*, etoposide, the semi-synthetic lignan, from Mayapple *Podophyllum peltatum* and the diterpenoid taxol, commonly referred to as paclitaxel, from the Pacific yew, *Taxus brevifolia*. Of these agents, paclitaxel is the most exciting, recently receiving approval by the Food and Drug Administration for the treatment of refractory ovarian cancer. Since the isolation of artemisinin, there has been a concerted effort by investigators to study other therapeutic applications of artemisinin and its derivatives.

National Institutes of Health reported that artemisinin is inactive against P388 leukemia. See NCI Report on NSC 369397 (tested on Oct. 25, 1983). Later anticancer studies that have been conducted on cell line panels consisting of 60 lines organized into nine, disease-related subpanels including leukemia, non-small-cell lung cancer, colon, CNS, melanoma, ovarian, renal, prostate and breast cancers, further confirm that artenisinin displays very little anticancer activity. A series of artemisinin-related endoperoxides were tested for cytotoxicity to Ehrlich ascites tumor (EAT) cells using the microculture tetrazolum (MTT) assay, H. J. Woerdenbag, et al. "Cytotoxicity of Artemisinin-Related Endoperoxides to Ehrlich Ascites Tumor Cells," *Journal of Natural Products*, 56(6):849–856 (1993). The MTT assay, used to test the artemisinin-related endoperoxides for cytotoxicity, is based on the metabolic reduction of soluble tetrazolium salts into insoluble colored formazan products by mitochondrial dehydrogenase activity of the tumor cells. As parameters for cytotoxicity, the $IC_{50}$ and $IC_{80}$ values, the drug concentrations causing respectively 50% and 80% growth inhibition of the tumor cells, were used. Artemisinin (I) had an $IC_{50}$ value of 29.8 μM. Derivatives of dihydroartemisinin (II-1) being developed as antimalarial drugs (artemether (II-2), arteether (III-3), sodium artesunate (II-4), artelinic acid (II-5) and sodium artelinate (II-6)), exhibited a somewhat more potent cytotoxicity. Their $IC_{50}$ values ranged from 12.2 μM to 19.9 μM. The dihydroartemisinin condensation by-product dimer (II-7), disclosed previously by M. Cao, et al., 1984, was the most potent cytotoxic agent, its $IC_{50}$ being 1.4 μM. At this drug concentration the condensation by-product (II-7) is approximately twenty-two times more cytotoxic than artemisinin and sixty times more cytotoxic than dihydroartemisinin (II-1), the parent compound.

While artemisinin and its related derivatives (II-1–6) discussed above demonstrated zero to slight antiproliferative and antitumor activity, it has been discovered that a class of artemisinin dimer compounds exhibits antiproliferative and antitumor activities that are, in vitro, equivalent to or greater than known antiproliferative and antitumor agents. See, U.S. Pat. No. 5,677,468 incorporated herein by reference. Unfortunately, while the in vitro results of these artemisinin compounds are encouraging these compounds do not appear to have significant antitumor activity on the treatment of tumor cells in mice.

There is still a need, therefore, to develop a more efficient method for the formation of hydrolytically more stable C-10 carbon-substituted deoxoartemisinin compounds and structural analogs thereof having antimalarial, and antiproliferative and antitumor activities that are equivalent to or greater than those of known antimalarial, and antiproliferative and antitumor agents, respectively.

SUMMARY OF THE INVENTION

Accordingly, it is an object of the invention to provide a class of artemisinin related dimers which demonstrate antiproliferative and antitumor activities.

More specifically, it is an object of this invention to provide a class of trioxane dimers which demonstrate antiproliferative and antitumor activities and that are considerably more stable than artemether and related C-10 ethers and esters toward hydrolysis.

A further object of the invention is to provide artemisinin dimers to be used clinically as chemotherapeutic anticancer drugs.

An additional object of this invention is to provide a class of trioxane monomers to be used clinically as chemotherapuetic antimalarial drugs.

Additional objects, advantages and novel features of this invention shall be set forth in part in the description and examples that follow, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein the compositions of this invention comprise C-10 carbon-substituted derivatives of the trioxane 10-deoxoartemisinin (VII) of the following structure of diastereomers thereof, having antimalarial, and antiproliferative and antitumor activities:

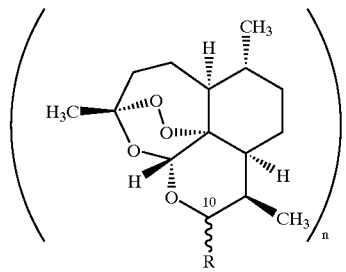

wherein, the monomers of the present invention are formed when n is 1 and R is an unsubstituted or substituted aryl, heteroaryl, polyethylene glycol, acetylenic, aroylmethylene or alkanoylmethylene group or the dimers of the present invention are formed when n is 2 and R is a linker such as an unsubstituted or substituted alkyl, alkenyl, aryl, heteroaryl, polyethylene glycol, diketone, or a bis-acetylene group.

BRIEF DESCRIPTION OF THE DRAWINGS

The accompanying drawings, which are incorporated in and form a part of the specification, illustrate the preferred embodiments of the present invention, and together with the description serve to explain the principles of the invention.

In the drawings, FIGS. 1 and 2, the horizontal axis depicts various dilutions of the test compounds, ranging from $10^{-6}$ to $7 \times 10^{-9}$ molar, that were exposed to murine keratinocytes. The vertical axis (cell number) depicts the number of murine keratinocyte cells present after exposure to a specific concentration of the tested compound as compared to the cell number at time zero.

Figure 1:
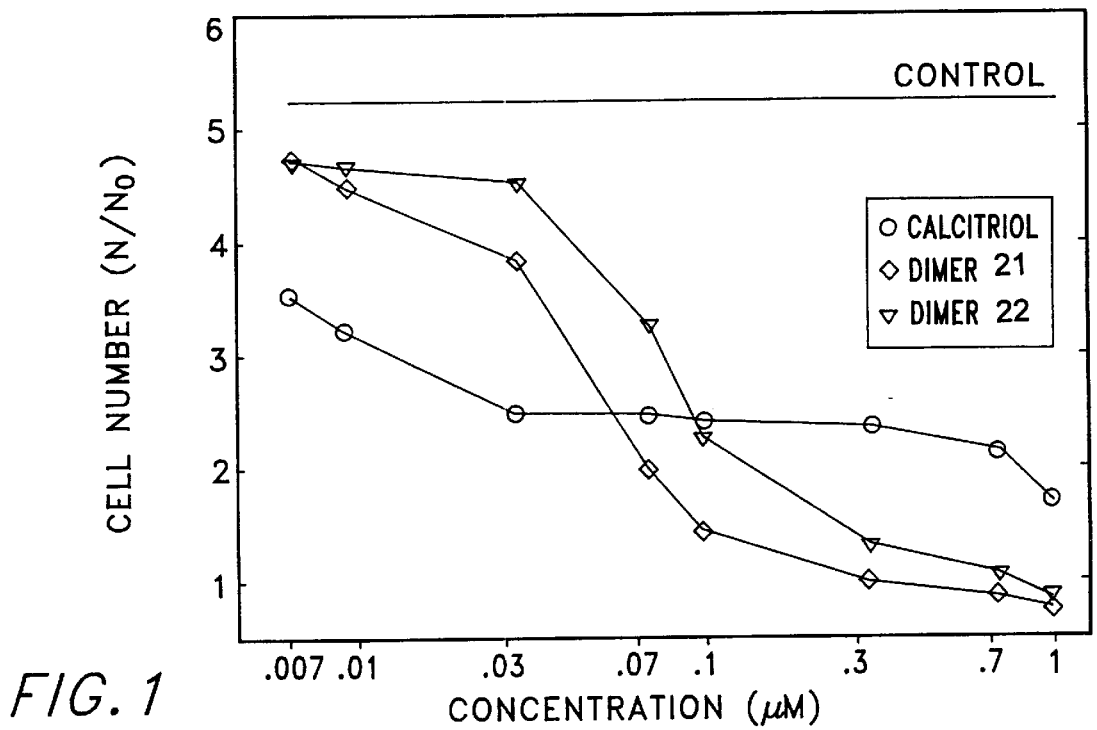

In the drawings, FIGS. 3–11, the horizontal axis depicts various dilutions of the text compound, ranging from $10^{-4}$ to $10^{-9}$ molar, that were exposed to the specified cancer cell lines. The vertical axis (percentage growth) depicts the growth of the specified cell line when exposed to a specific concentration of the tested compound as compared to the growth of the same cancer cell line not exposed to any compound.

In the Drawings:

FIG. 1 depicts the dose response curves generated by exposing murine keratinocytes to various concentrations of the C-10 carbon-substituted trioxane dimers 21 and 22 of the present invention versus calcitriol and versus a control using only a solvent.

Figure 2:
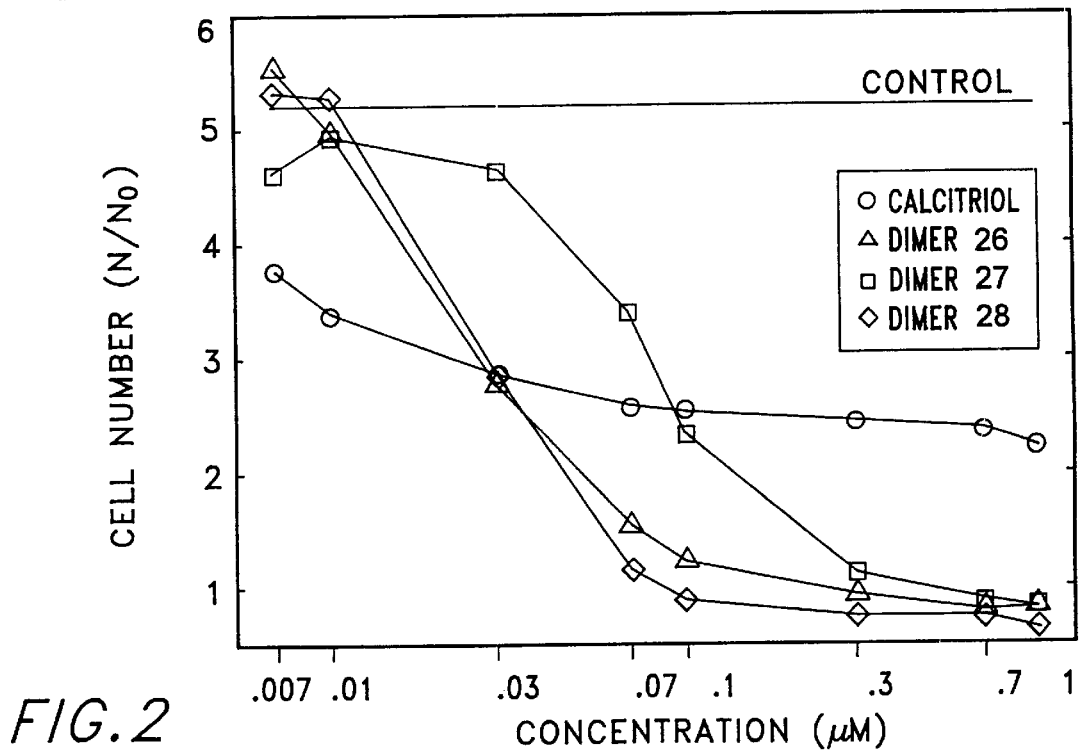

FIG. 2 depicts the dose response curves generated by exposing murine keratinocytes to various concentrations of the C-10 carbon-substituted trioxane dimers 26, 27 and 28 of the present invention versus calcitriol and versus a control using only a solvent.

Figure 3A:
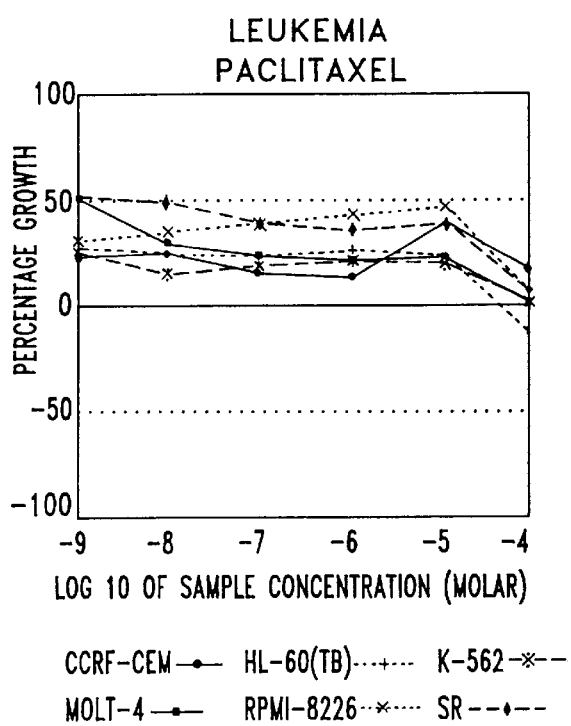

FIG. 3a depicts the dose response curves generated by exposing various leukemia cancer cell lines to various concentrations of paclitaxel.

Figure 3B:
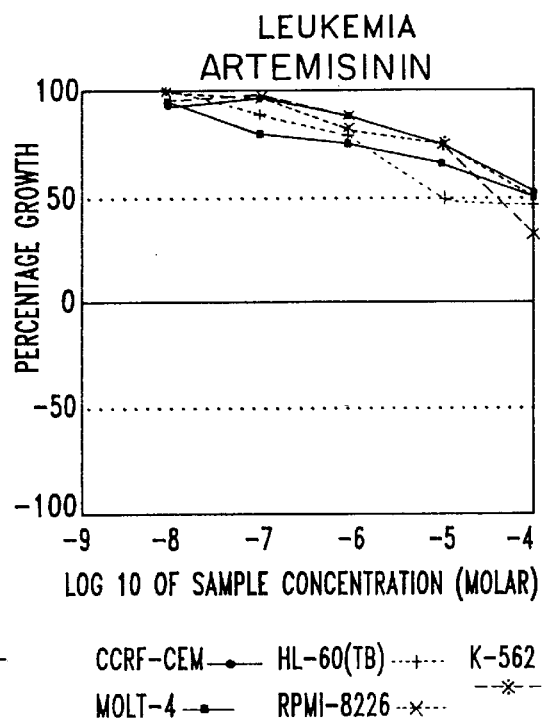

FIG. 3b depicts the dose response curves generated by exposing various leukemia cancer cell lines to various concentrations of artemisinin.

Figure 3C:
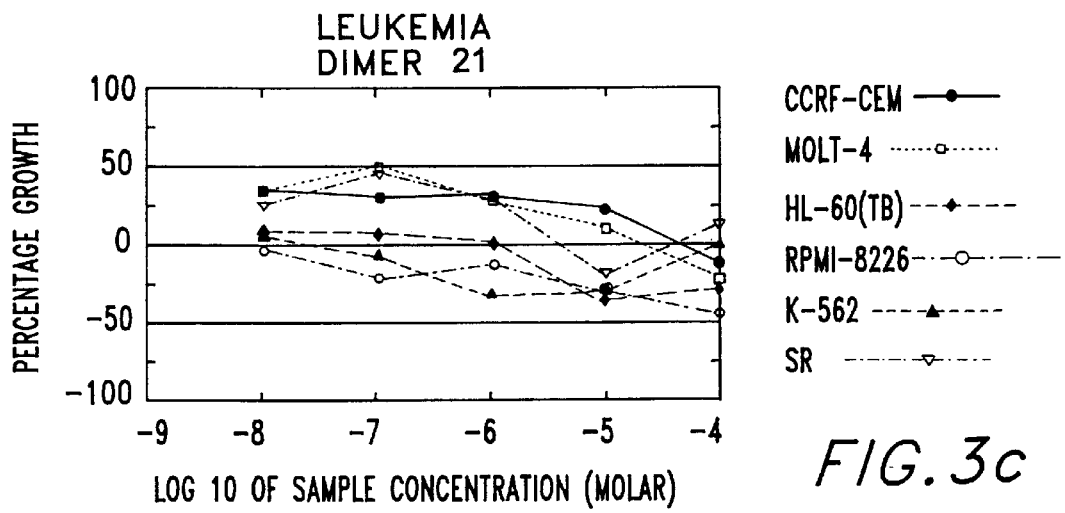

FIG. 3c depicts the dose response curves generated by exposing various leukemia cancer cell lines to various concentrations of the C-10 carbon-substituted dimer 21 of the present invention.

Figure 3D:
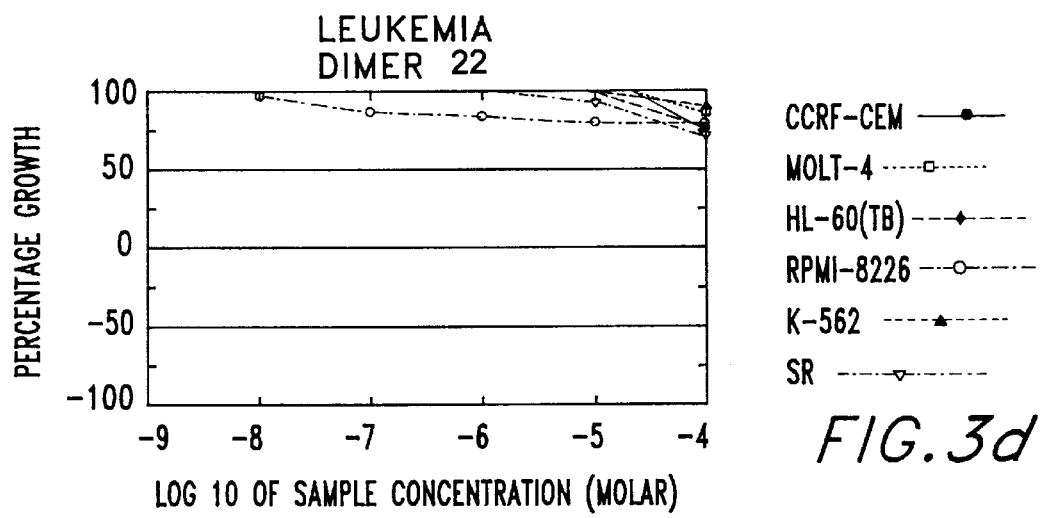

FIG. 3d depicts the dose response curves generated by exposing various leukemia cancer cell lines to various concentrations of the C-10 carbon-substituted dimer 22 of the present invention.

Figure 3E:
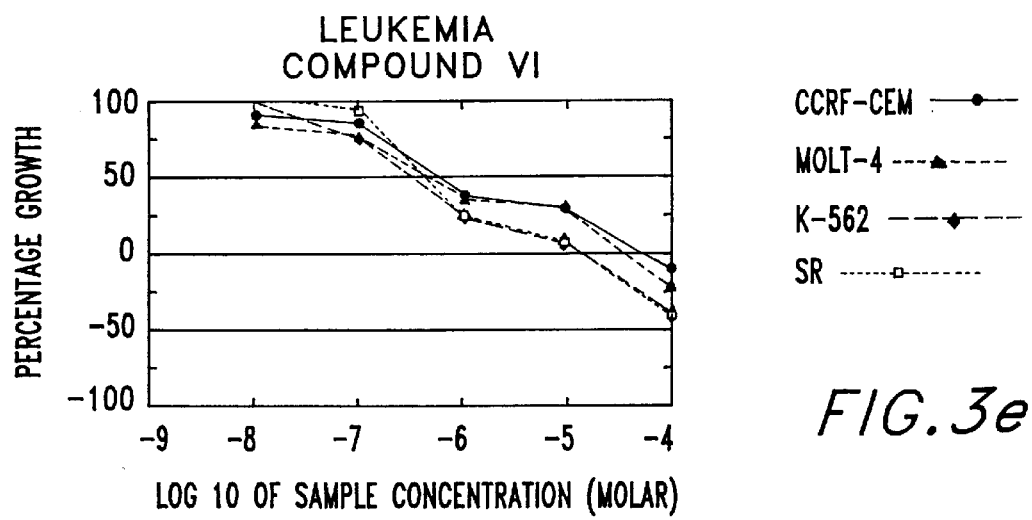

FIG. 3e depicts the dose response curves generated by exposing various leukemia cancer cell lines to various concentrations of compound VI.

Figures 4A, 4B:
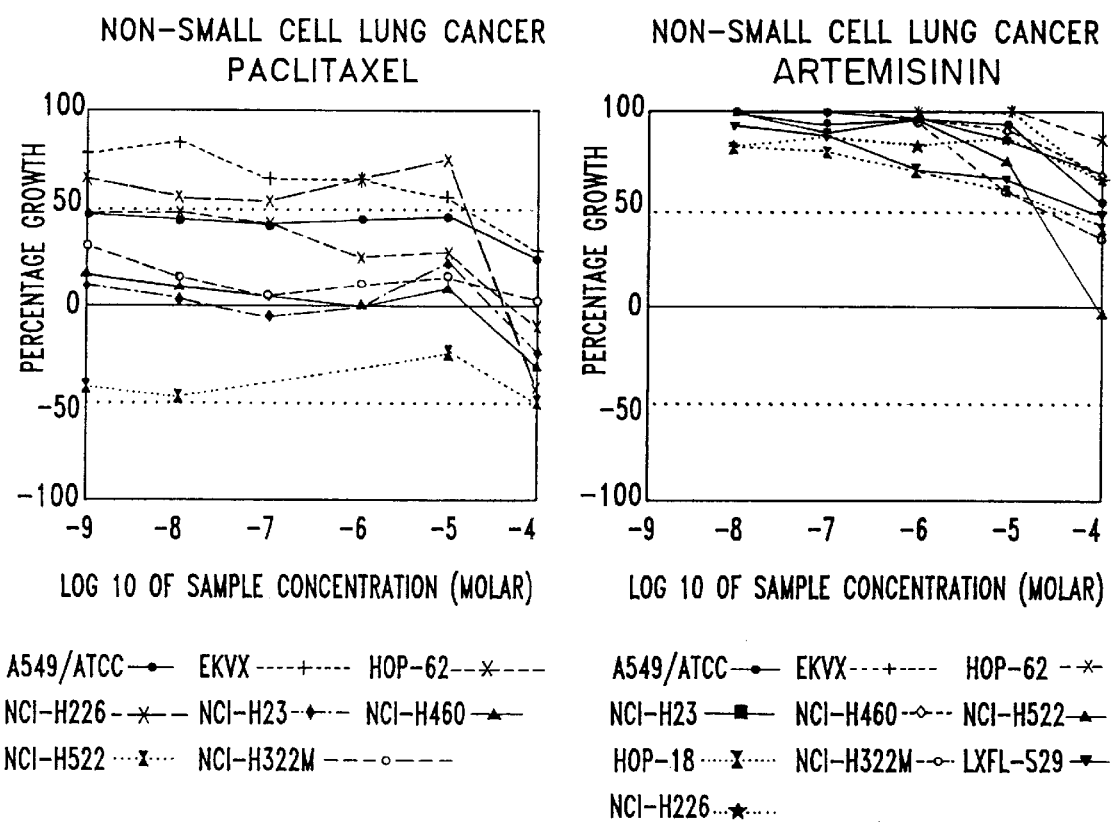

FIG. 4a depicts the dose response curve generated by exposing various non-small cell lung cancer cell lines to various concentrations of paclitaxel.

FIG. 4b depicts the dose response curves generated by exposing various non-small cell lung cancer cell lines to various concentrations of the artemisinin.

Figure 4C:
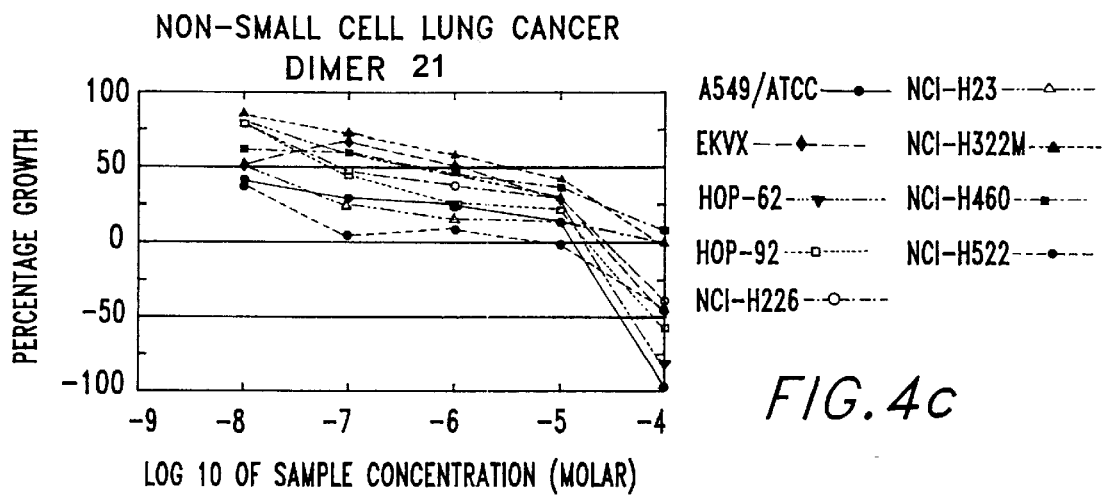

FIG. 4c depicts the dose response curves generated by exposing various non-small cell lung cancer cell lines to various concentrations of the C-10 carbon-substituted dimer 21 of the present invention.

Figure 4D:
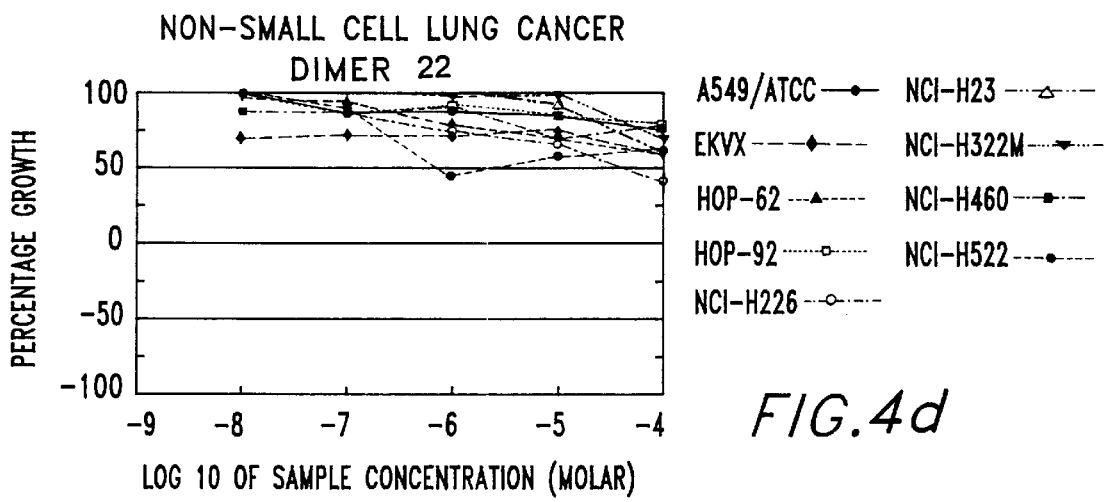

FIG. 4d depicts the dose response curves generated by exposing various non-small cell lung cancer cell lines to various concentrations of the C-10 carbon-substituted dimer 22 of the present invention.

Figure 4E:
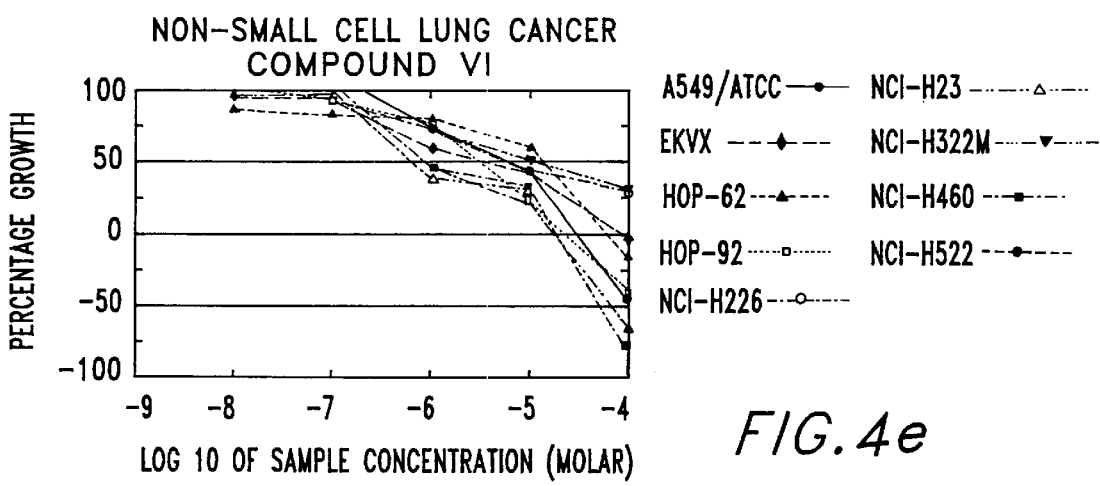

FIG. 4e depicts the dose response curves generated by exposing various small cell lung cancer cell lines to various concentrations of compound VI.

Figures 5A, 5B:
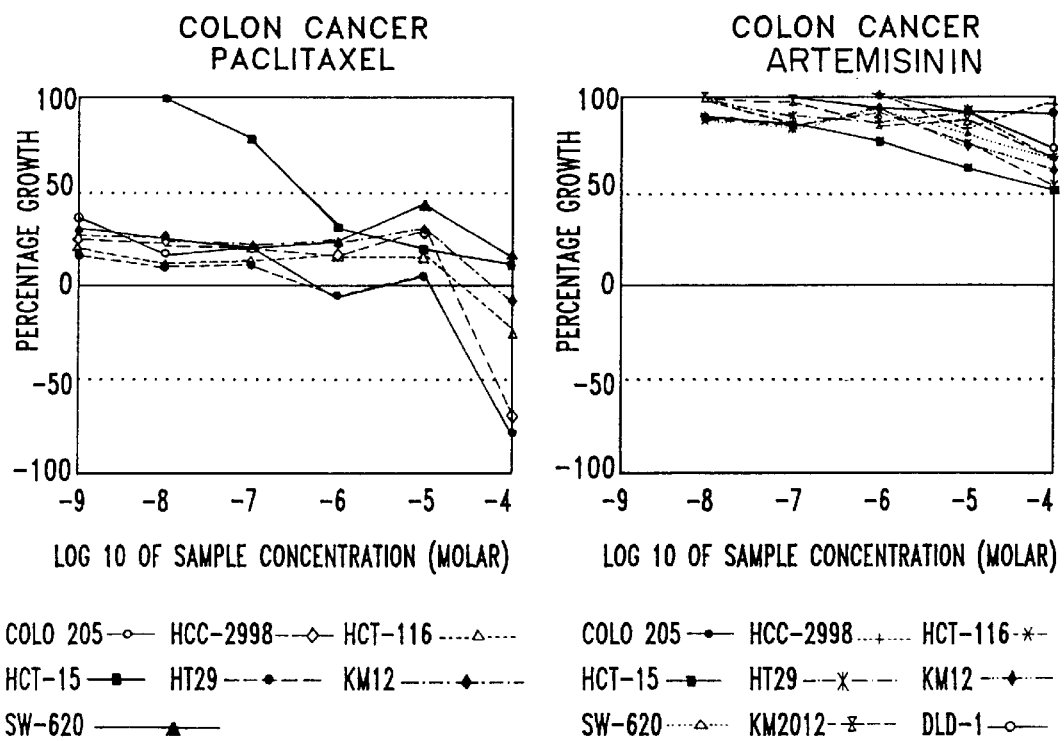

FIG. 5a depicts the dose response curves generated by exposing various colon cancer cell lines to various concentrations of paclitaxel.

FIG. 5b depicts the dose response curves generated by exposing various colon cancer cell lines to various concentrations of artemisinin.

Figure 5C:
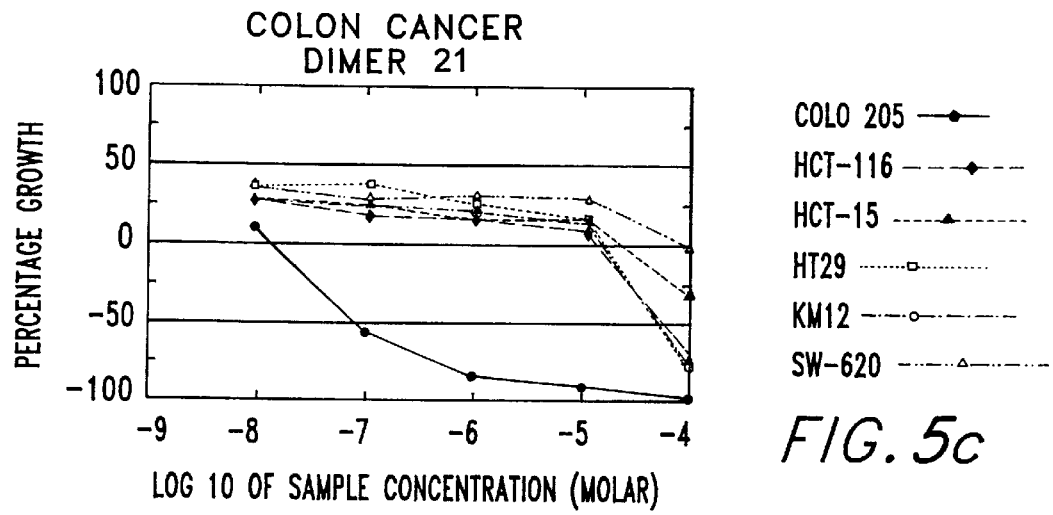

FIG. 5c depicts the dose response curves generated by exposing various colon cancer cell lines to various concentrations of the C-10 carbon-substituted dimer 21 of the present invention.

Figure 5D:
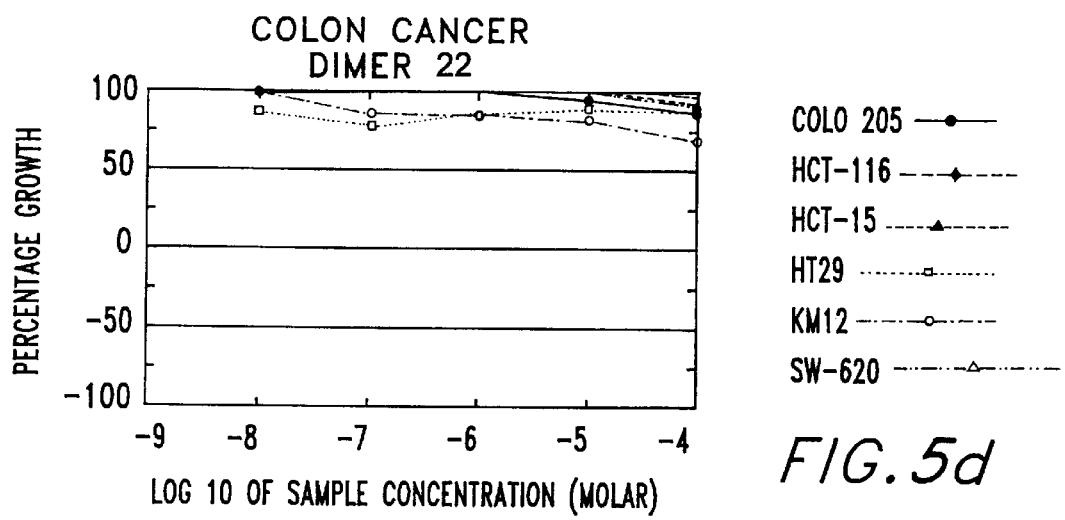

FIG. 5d depicts the dose response curves generated by exposing various colon cancer cell lines to various concentrations of the C-10 carbon-substituted dimer 22 of the present invention.

Figure 5E:
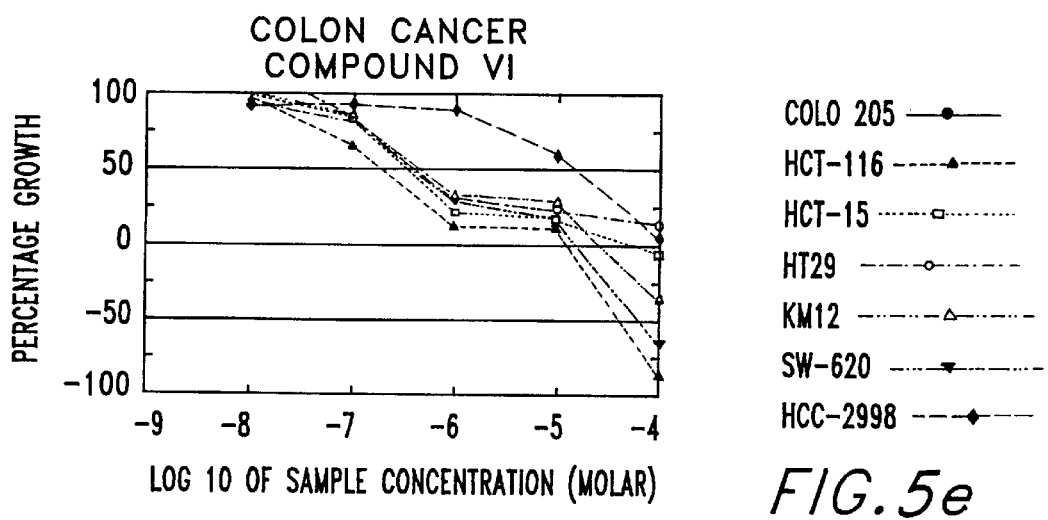

FIG. 5e depicts the dose response curves generated by exposing various colon cancer cell lines to various concentrations of compound VI.

Figures 6A, 6B:
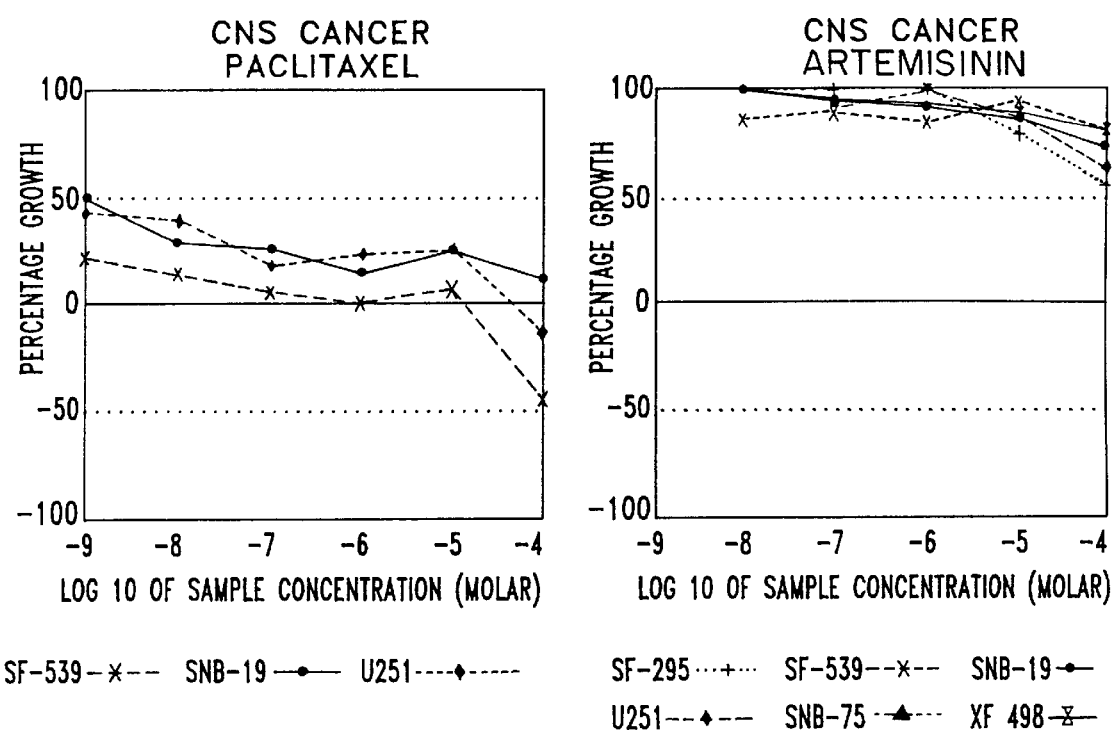

FIG. 6a depicts the dose response curves generated by exposing various CNS cancer cell lines to various concentrations of paclitaxel.

FIG. 6b depicts the dose response curves generated by exposing various CNS cancer cell lines to various concentrations of artemisinin.

Figure 6C:
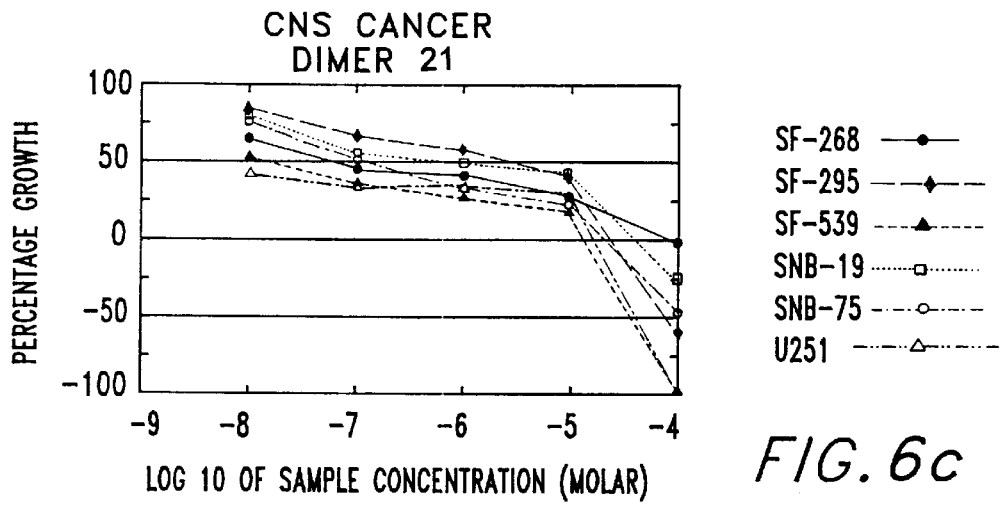

FIG. 6c depicts the dose response curves generated by exposing various CNS cancer cell lines to various concentrations of the C-10 carbon-substituted dimer 21 of the present invention.

Figure 6D:
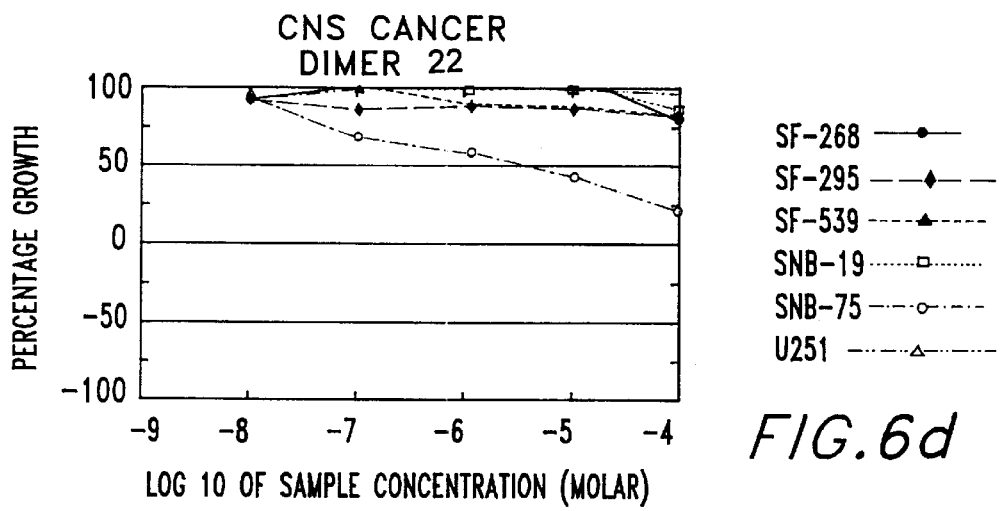

FIG. 6d depicts the dose response curves generated by exposing various CNS cancer cell lines to various concentrations of the C-10 carbon-substituted dimer 22 of the present invention.

Figure 6E:
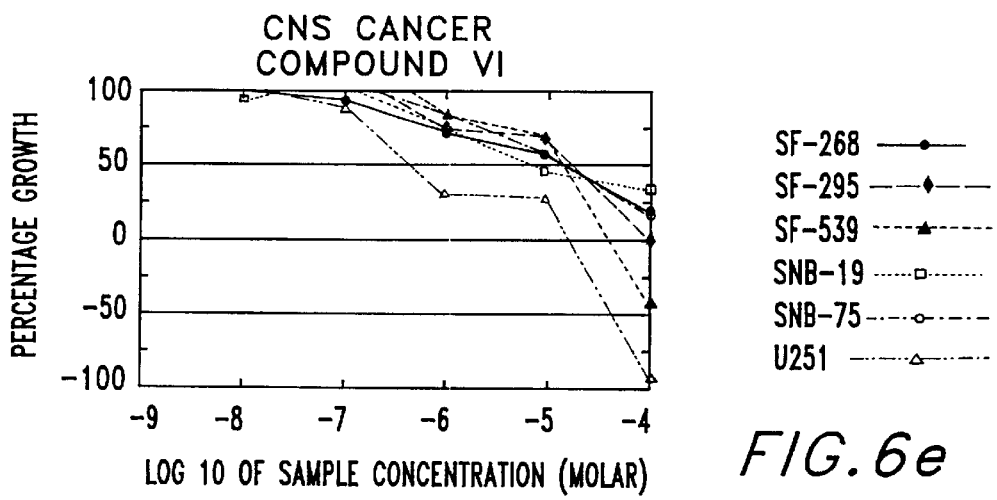

FIG. 6e depicts the dose response curves generated by exposing various CNS cancer cell lines to various concentrations of compound VI.

Figures 7A, 7B:
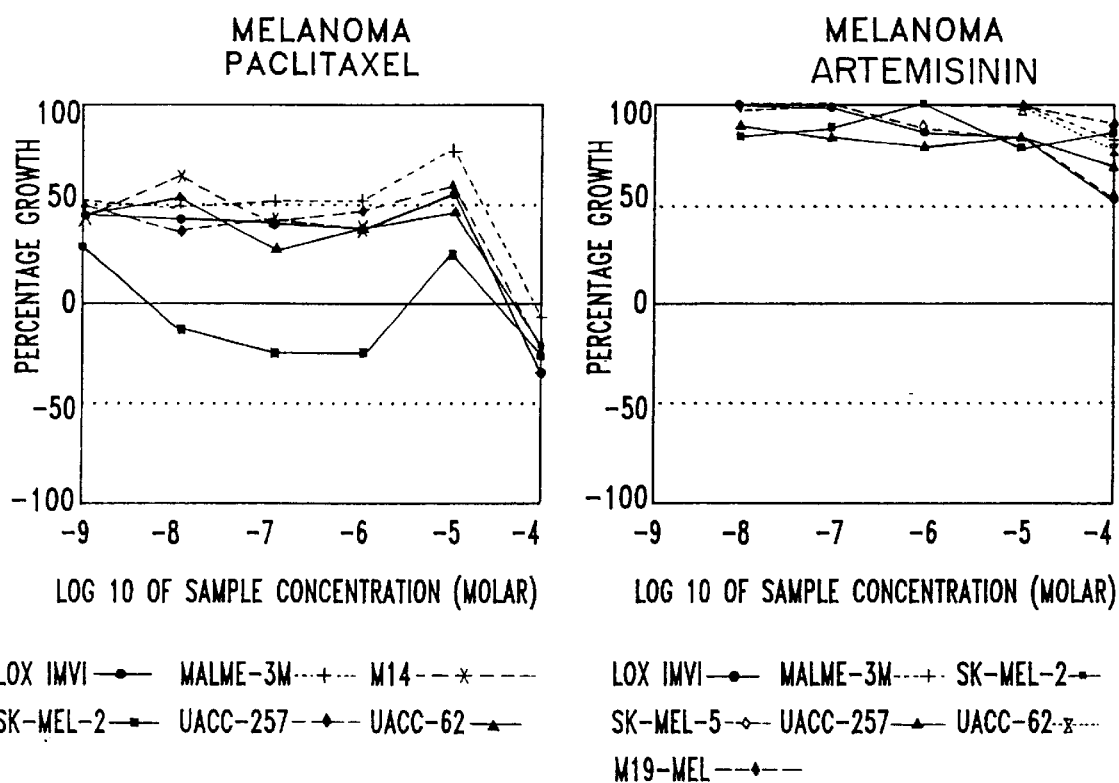

FIG. 7a depicts the dose response curves generated by exposing various melanoma cancer cell lines to various concentrations of paclitaxel.

FIG. 7b depicts the dose response curves generated by exposing various melanoma cancer cell lines to various concentrations of artemisinin.

Figure 7C:
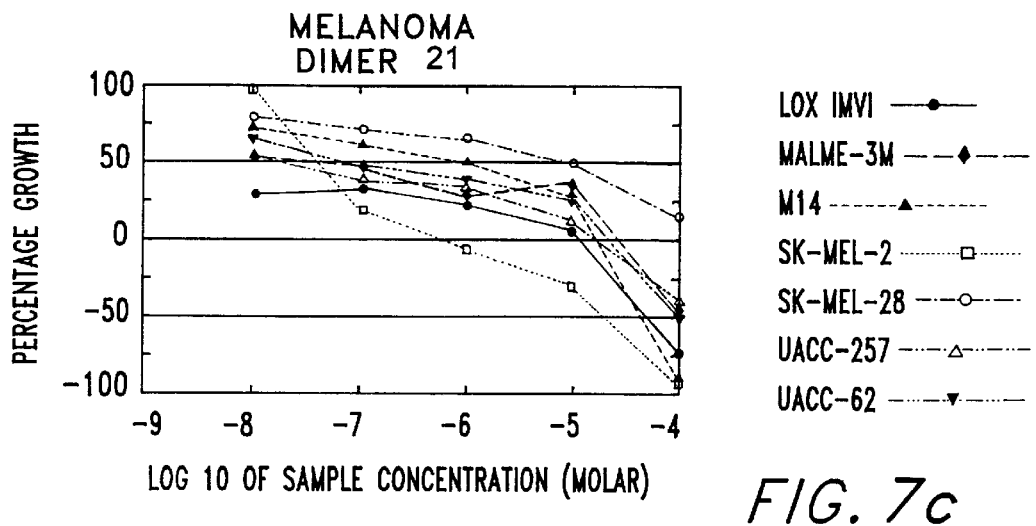

FIG. 7c depicts the dose response curves generated by exposing various melanoma cancer cell lines to various concentrations of the C-10 carbon-substituted dimer 21 of the present invention.

Figure 7D:
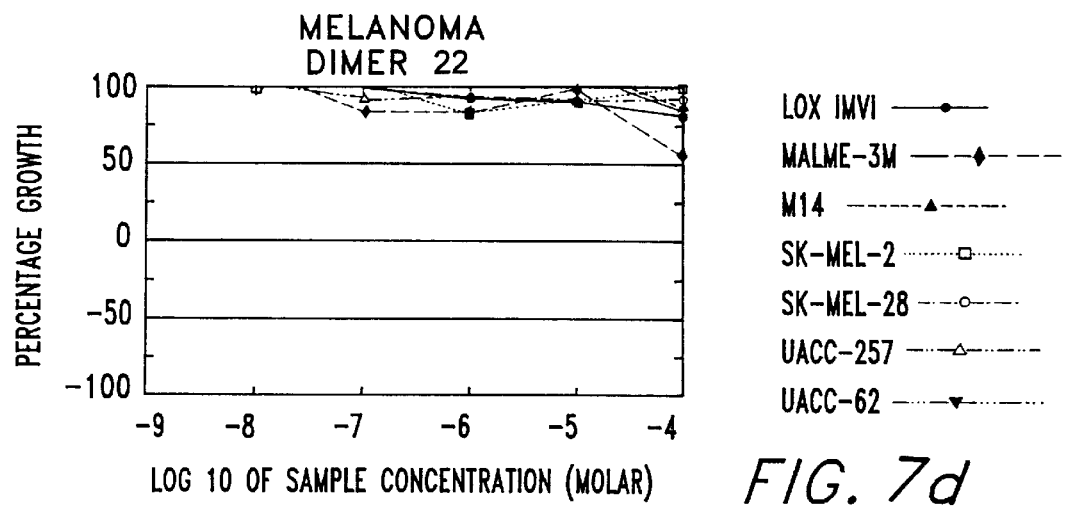

FIG. 7d depicts the dose response curves generated by exposing various melanoma cancer cell lines to various concentrations of the C-10 carbon-substituted dimer 22 of the present invention.

Figure 7E:
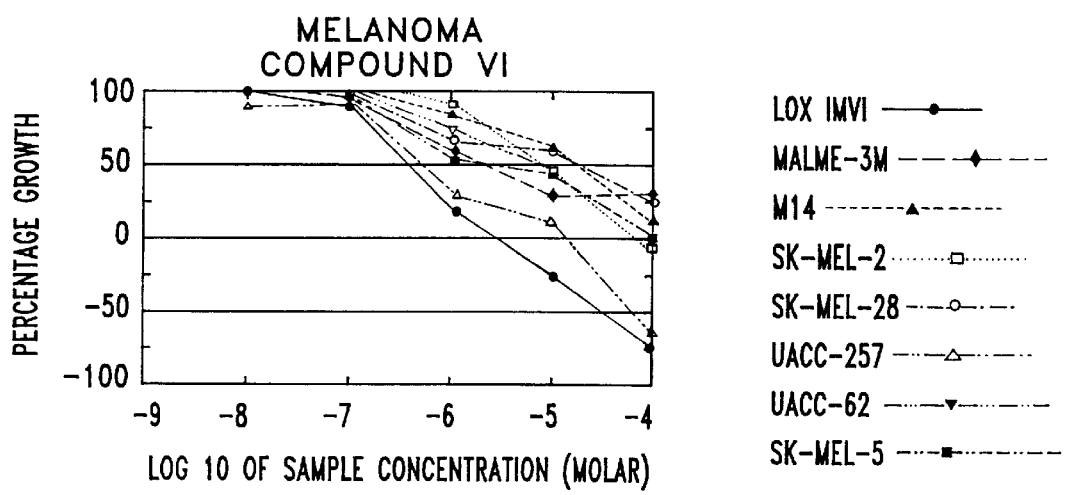

FIG. 7e depicts the dose response curves generated by exposing various melanoma cancer cell lines to various concentrations of compound VI.

Figure 8A:
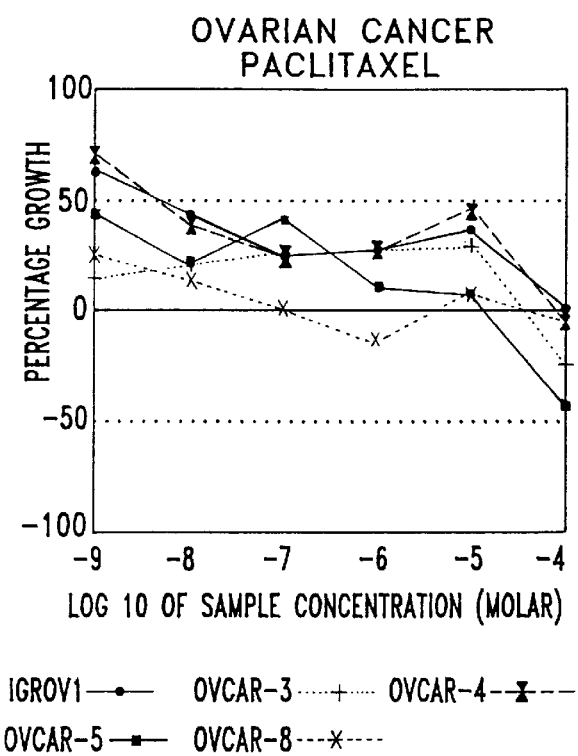

FIG. 8a depicts the dose response curves generated by exposing various ovarian cancer cell lines to various concentrations of paclitaxel.

Figure 8B:
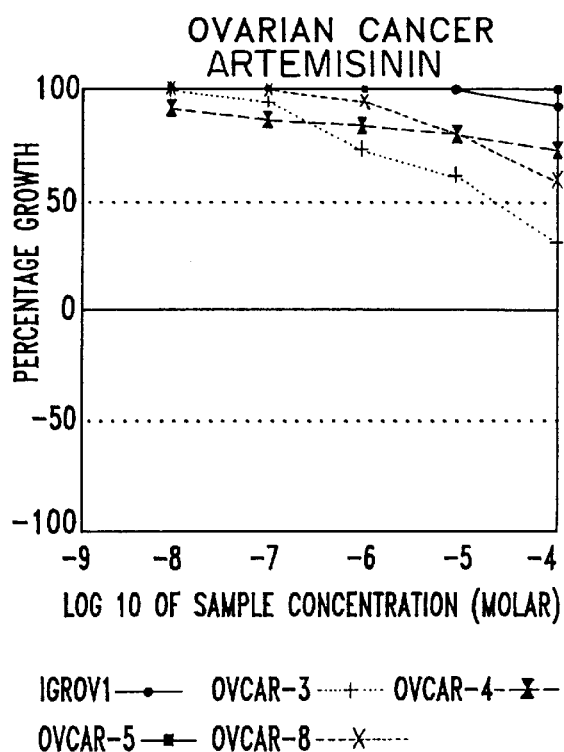

FIG. 8b depicts the dose response curves generated by exposing various ovarian cancer cell lines to various concentrations of artemisinin.

Figure 8C:
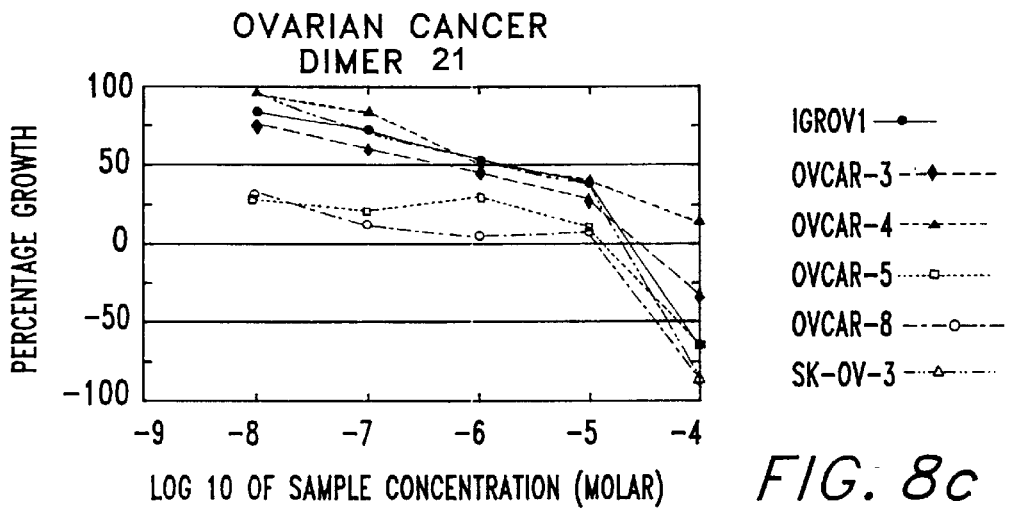

FIG. 8c depicts the dose response curves generated by exposing various ovarian cancer cell lines to various concentrations of the C-10 carbon-substituted dimer 21 of the present invention.

Figure 8D:
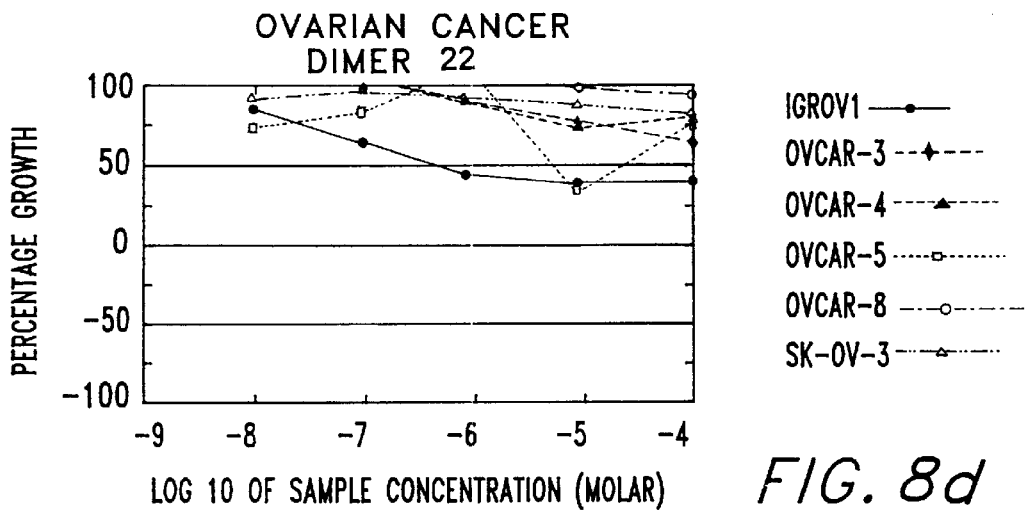
Figure 8E:
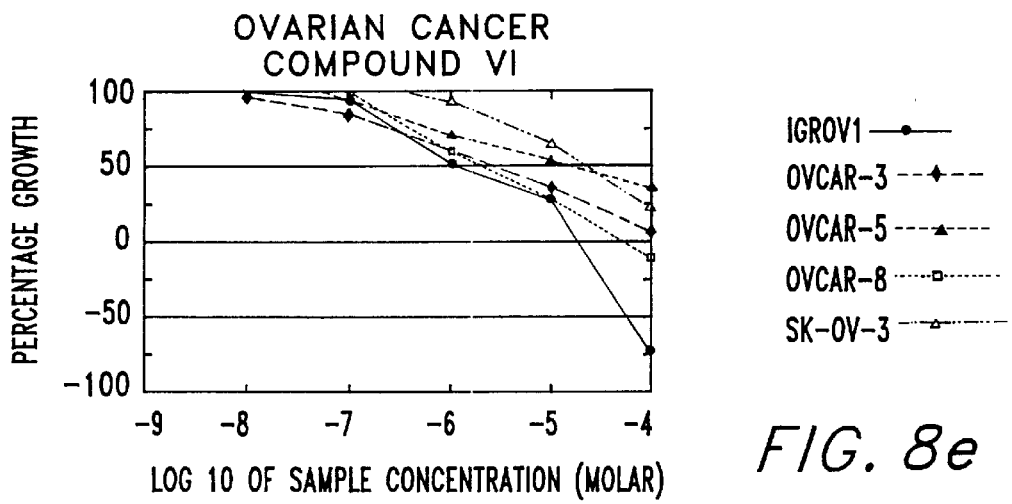

FIG. 8d depicts the dose response curves generated by exposing various ovarian cancer cell lines to various concentrations of the C-10 carbon-substituted dimer 22 of the present invention.

Figures 9A, 9B:
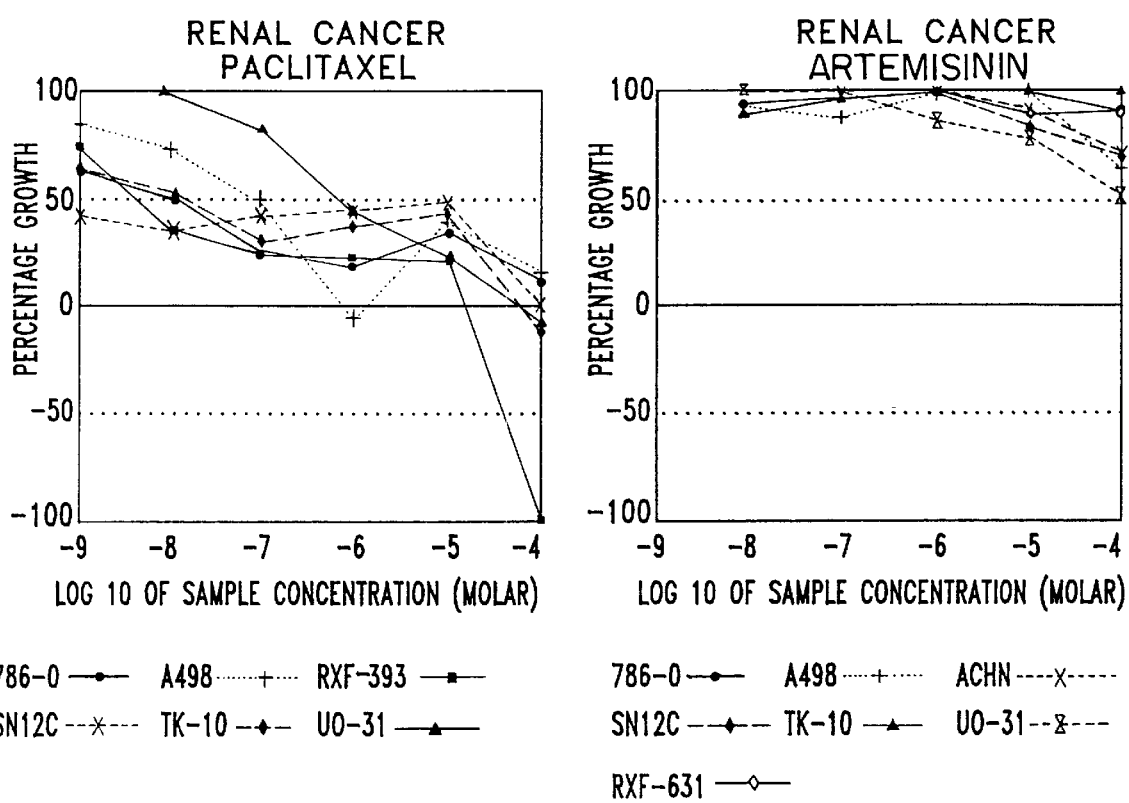

FIG. 9a depicts the dose response curves generated by exposing various renal cancer cell lines to various concentrations of paclitaxel.

FIG. 9b depicts the dose response curves generated by exposing various renal cancer cell lines to various concentrations of artemisinin.

Figure 9C:
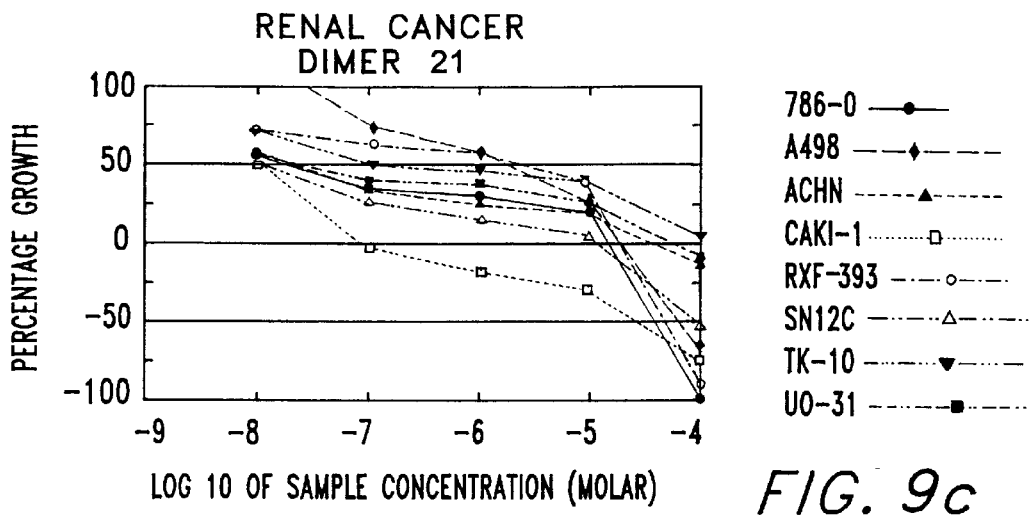

FIG. 9c depicts the dose response curves generated by exposing various renal cancer cell lines to various concentrations of the C-10 carbon-substituted dimer 21 of the present invention.

Figure 9D:
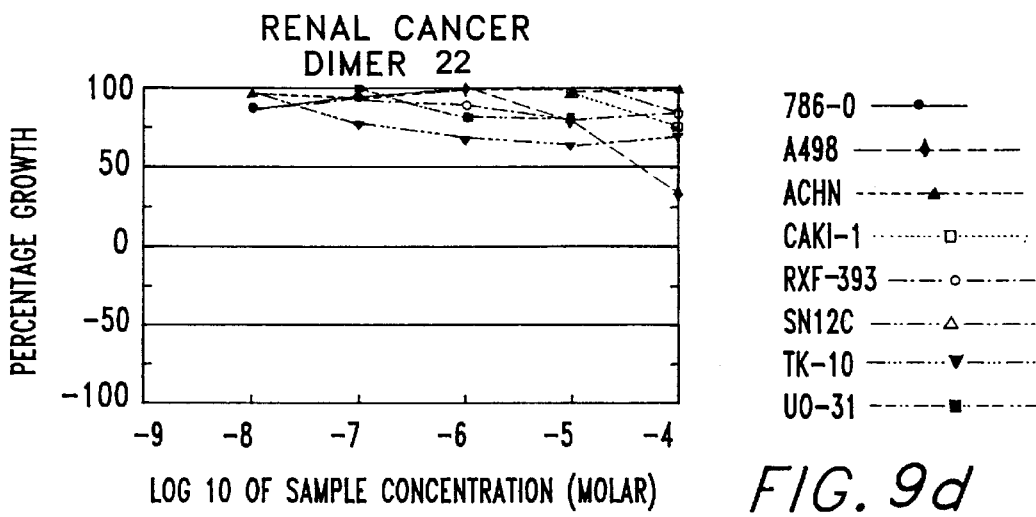

FIG. 9d depicts the dose response curves generated by exposing various renal cancer cell lines to various concentrations of the C-10 carbon-substituted dimer 22 of the present invention.

Figure 9E:
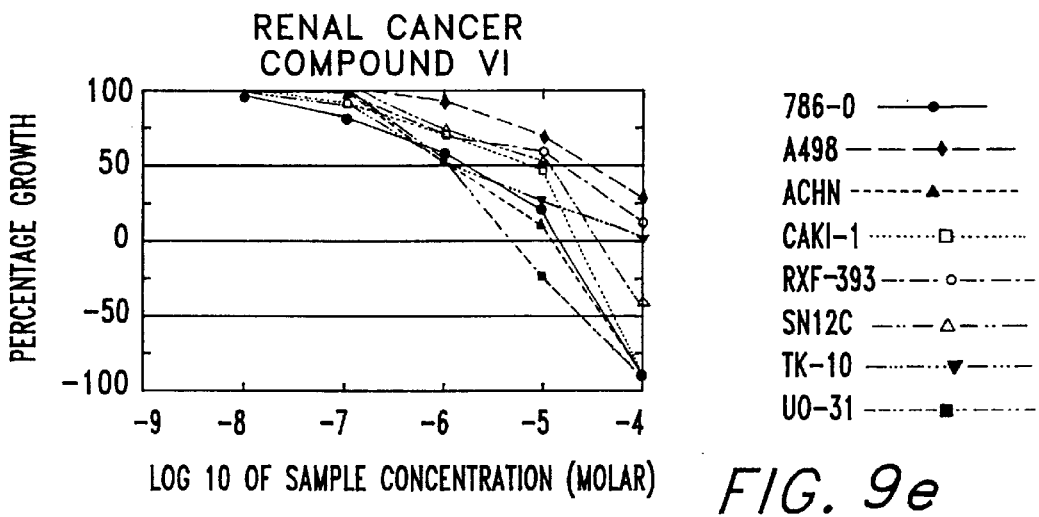

FIG. 9e depicts the dose response curves generated by exposing various renal cancer cell lines to various concentrations of compound VI.

Figures 10A, 10B:
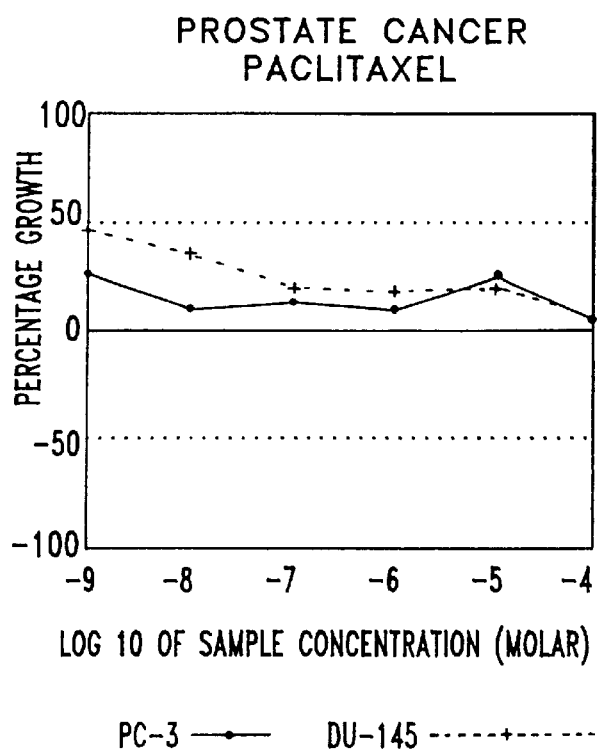

FIG. 10a depicts the dose response curves generated by exposing various prostate cancer cell lines to various concentrations of paclitaxel.

FIG. 10b the response curves generated by exposing various prostate cancer cell lines to various concentrations of artemisinin was not evaluated.

Figure 10C:
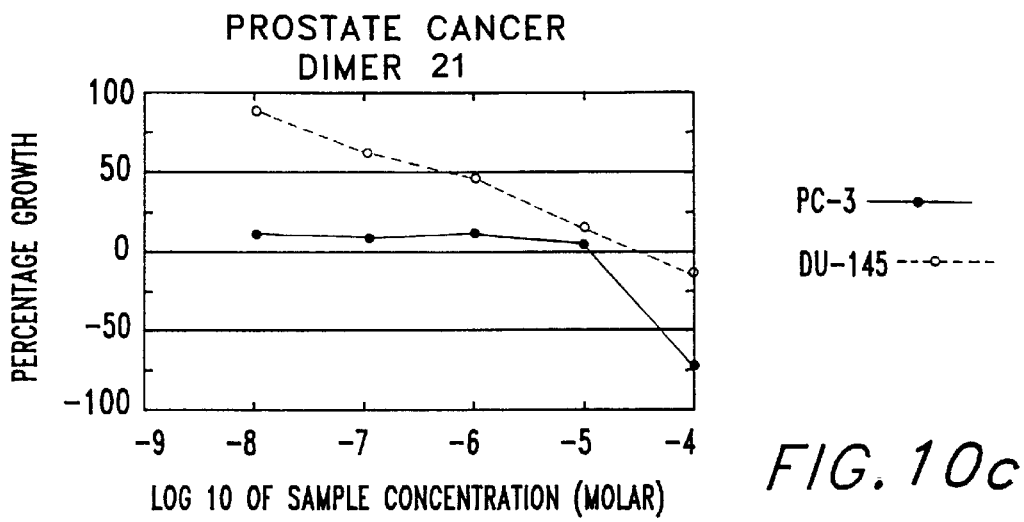

FIG. 10c depicts the dose response curves generated by exposing various prostate cancer cell lines to various concentrations of the C-10 carbon-substituted dimer 21 of the present invention.

Figure 10D:
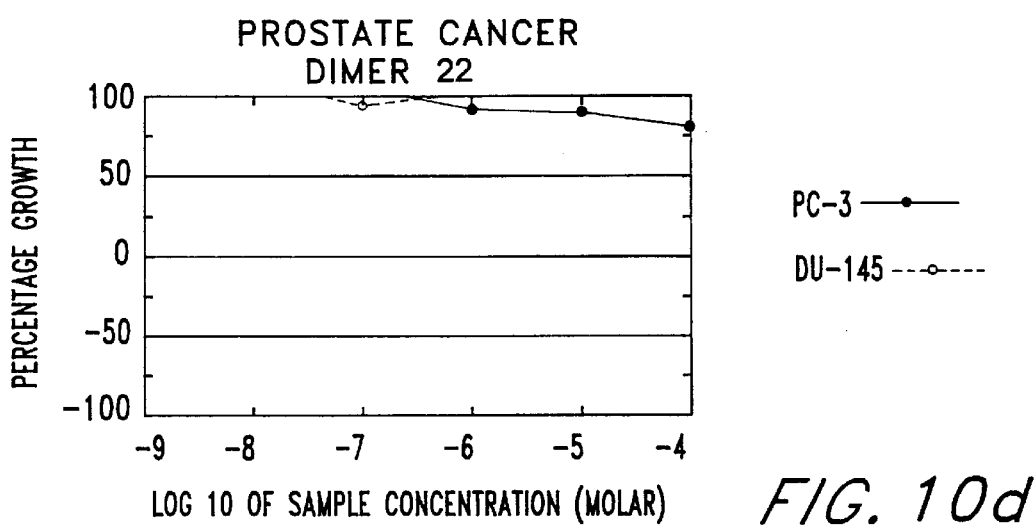

FIG. 10d depicts the dose response curves generated by exposing various prostate cancer cell lines to various concentrations of the C-10 carbon-substituted dimer 22 of the present invention.

Figure 10E:
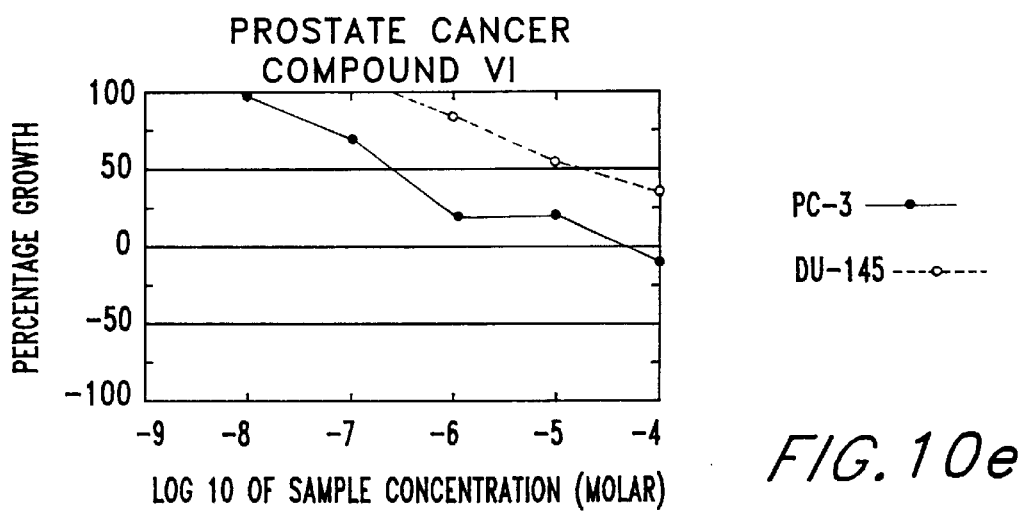

FIG. 10e depicts the dose response curves generated by exposing various prostate cancer cell lines to various concentrations of compound VI.

Figures 11A, 11B:
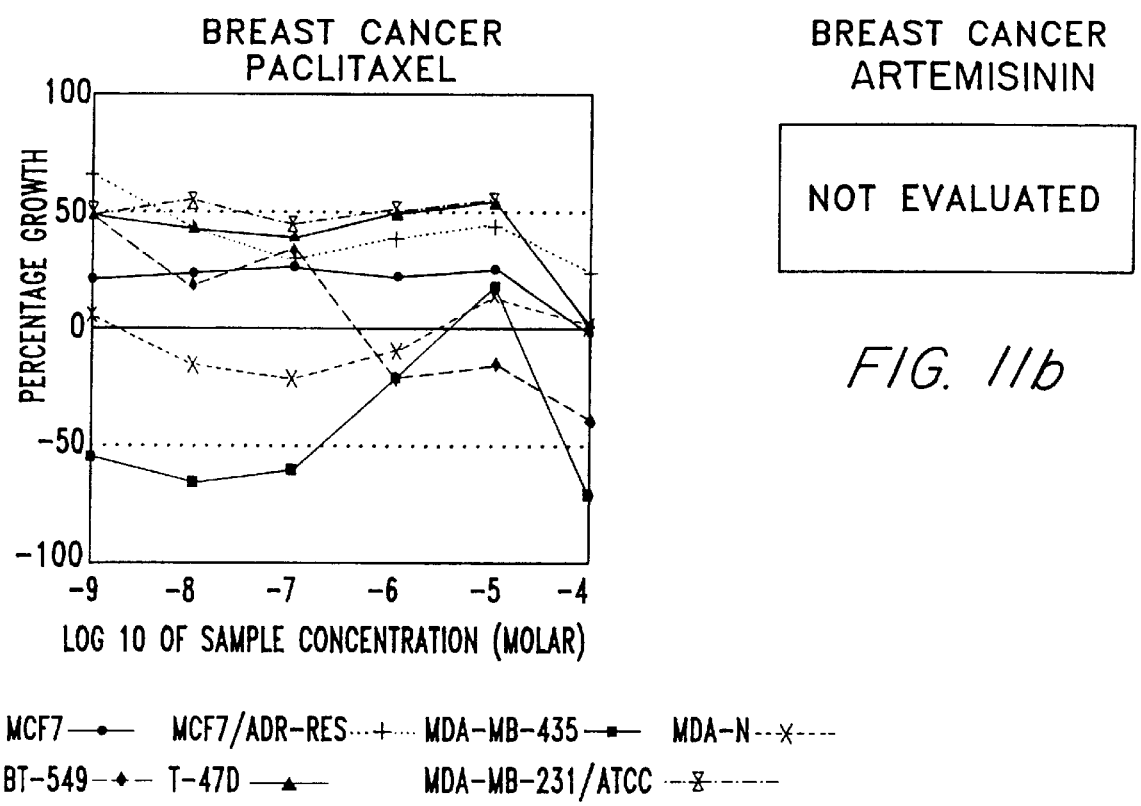

FIG. 11a depicts the dose response curves generated by exposing various breast cancer cell lines to various concentrations of paclitaxel.

FIG. 11b the dose response curves generated by exposing various breast cancer cell lines to various concentrations of artemisinin was not evaluated.

Figure 11C:
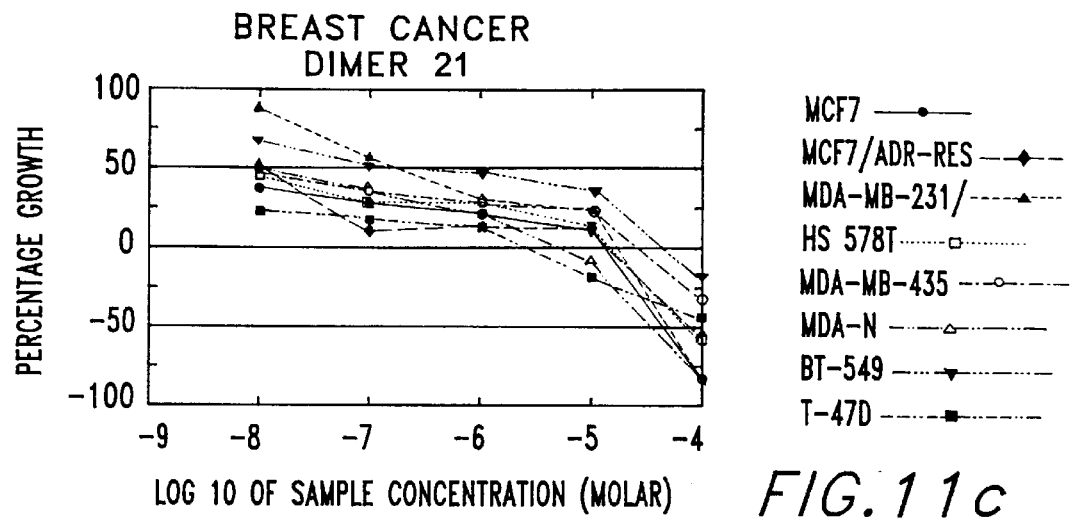

FIG. 11c depicts the dose response generated by exposing various breast cancer cell lines to various concentrations of the C-10 carbon-substituted dimer 21 of the present invention.

Figure 11D:
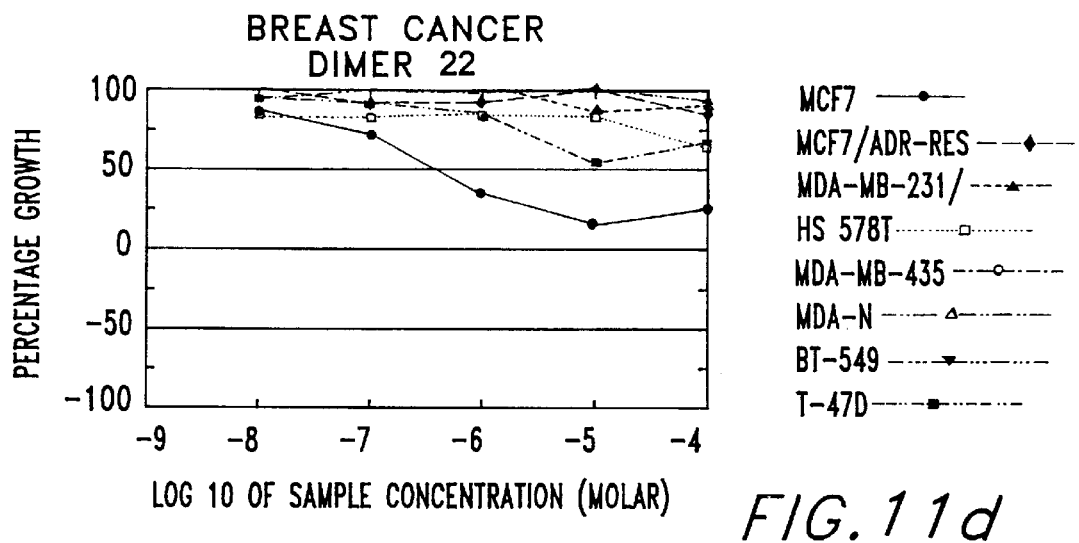

FIG. 11d depicts the dose response curves generated by exposing various breast cancer cell lines to various concentrations of the C-10 carbon-substituted dimer 22 of the present invention.

Figure 11E:
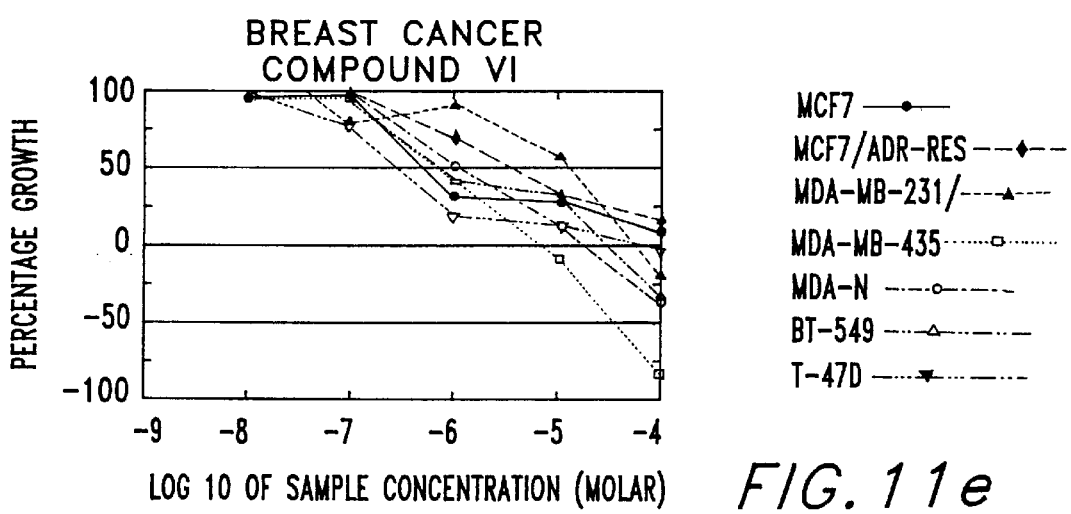

FIG. 11e depicts the dose response curves generated by exposing various breast cancer cell lines to various concentrations of compound VI.

DETAILED DESCRIPTION OF THE PREFERRED EMBODIMENT

The present invention provides a direct two-step procedure for the replacement of the pyranose anomeric 10-OH group in dihydroartemisinin (II-1) by a variety of carbon nucleophiles, resulting in the novel C-10 carbon-substituted monomeric and dimeric (VII) compounds:

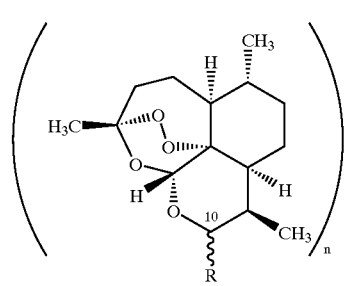

wherein, the monomers of the present invention are formed when n is 1 and R is an unsubstituted or substituted aryl, heteroaryl, polyethylene glycol, acetylenic, aroylmethylene, or alkanoylmethylene group or the dimers of the present invention are formed when n is 2 and R is a linker such as an unsubstituted or substituted alkyl, alkenyl, aryl, heteroaryl, polyethylene glycol, diketone, or a bis-acetylene group.

The synthesis of the C-10 carbon-substituted monomeric and dimeric compositions VII of the present invention have not been accomplished previously. Although they might be synthesized by other means, the present invention offers an efficient two-step process as described in further detail below. Preferably, the compounds of the present invention are synthesized by the two-step chemical operation illustrated below:

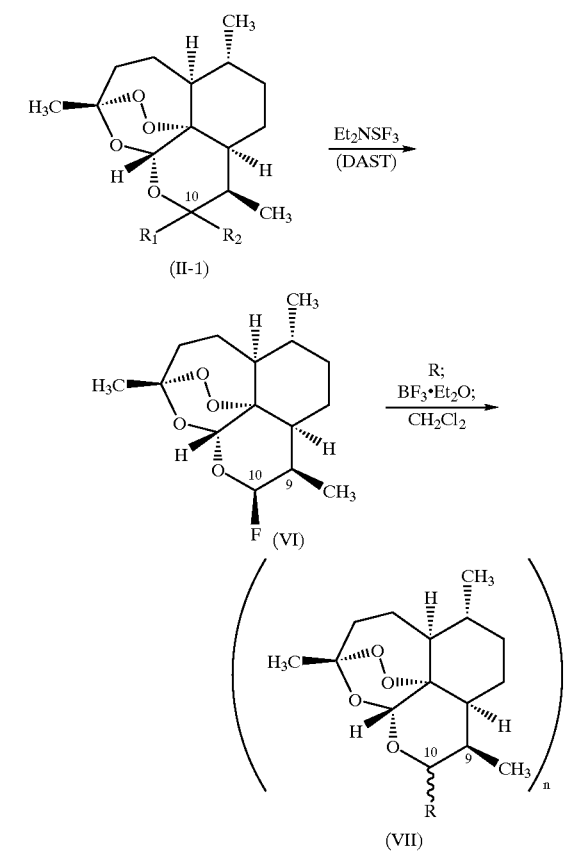

This process involves mild diethylaminosulfur trifluoride (DAST) fluorination of dihydroartemisinin (II-1), wherein $R_1$=H and $R_2$=OH, followed by the facile substitution of the anomeric fluorine atom in pyranosyl fluoride (VI) by various alkyl, alkenyl, alkynyl, aryl and heteroaryl nucleophiles (R) to form either α- or β-oriented C-10 carbon-substituted deoxoartemisinin monomeric or dimeric (VII) compounds. The simplicity and high chemical yields in this process of the present invention indicate that it can be used for the synthesis of a wide variety of other saturated, unsaturated, aromatic and heteroaromatic C-10 carbon-substituted analogs of the present invention. Several aspects of the process of the present invention are surprising and of value.

In general, the first step of the preferred process of the present invention, fluorination of the pyranose anomeric 10-OH group in dihydroartemisinin is accomplished by using an effective amount of a fluorinating agent. Effective fluorinating agents include, but are not limited to, 2-fluoropyridinium salts, hydrogen fluoride-pyridine, hexafluoropropene-amine complex and diethylaminosulfur trifluoride (DAST). An effective amount of one or more oxidizing agents can be utilized. In particular, one or more fluorinating agents from the above list can be employed, although diethylaminosulfur trifluoride is the preferred fluorinating agent. The relative effectiveness of the various possible fluorinating agents depends upon the concentration employed and other conditions of the reaction.

Various amounts of the fluorinating agent can be employed, but generally it should be present in the range of 1 to 10 molar equivalents of fluorinating agent per mole of dihydroartemisinin (II-1). Preferably, at least 1 equivalent of fluorinating agent per molar equivalent of dihydroartemisinin is needed for the reaction to proceed to completion.

To facilitate mixing of the starting materials, the fluorination is preferably accomplished utilizing an effective dissolution amount of a dihydroartemisinin solvent which is compatible with the particular fluorinating agent or agents employed. Typical solvents include tetrahydrofuran, water, acetone, aqueous dioxane, or mixtures thereof or other dihydroartemisinin solvents known to one of ordinary skill in the art.

In the preferred embodiment of the invention the fluorination of the pyranose anomeric 10-OH group in dihydroartemisinin is accomplished by dissolving the dihydroartemisinin using tetrahydrofuran and utilizing diethylaminosulfur trifluoride as the fluoridizing agent. The pyranose anomeric 10-OH group is fluorinated over a temperature range of −30° C. to 25° C. for 15 minutes to 24 hours for solutions which are approximately 1 to 2 mg/ml of dihydroartemisinin using 1 to 10 molar equivalents of the fluorinating reagent.

The second step of the process of the present invention, facile substitution of the anomeric fluorine atom in pyranosyl fluoride (VI) by various alkyl, alkenyl, alkynyl, aryl and heteroaryl carbon nucleophiles to form either α or β oriented C-10 carbon-substituted deoxoartemesinin (VII) compounds of the present invention is accomplished by dissolving the desired nucleophile and pyranose fluoride (VI) in a solvent which is compatible with the particular carbon nucleophiles employed. Typical solvents include dry methylene chloride, tetrahydrofuran or mixtures thereof or other solvents known to one of ordinary skill in the art.

In the preferred embodiment of the invention facile substitution of the anomeric fluoride atom in pyranosyl fluoride (VI) is accomplished by dissolving 1 to 10 molar equivalents and preferably 2 molar equivalents of an alkyl, alkenyl, alkynyl, aryl or heteroaryl carbon nucleophile with pyranosyl fluoride (VI) and cooling the mixture to −70 to −90° C. and preferably −78° C. Coupling of the carbon nucleophile with the pyranosyl fluoride occurs in the presence of boron trifluoride-etherate over a temperature range of −70° C. to room temperature.

Fluorination of readily available dihydroartemisinin lactol (II-1) where $R_1$=H and $R_2$=OH with DAST proceeded in high yield on a gram-scale to form a mixture of anomeric fluorides, with the β-fluoride VI vastly predominating and easily separated from the α-fluoride by immediate application of the crude product mixture to chromatography using a Florisil® column, exposure to water caused hydrolysis of these pyranosyl fluorides back into the reactant lactol II-1. After purification, however, 10β-fluoride VI is a stable crystalline solid. Coupling of either the α-fluoride or the β-fluoride VI with trimethylaluminum in the presence of boron trifluoride-etherate gave 10β-methyl derivative VII where n=1 and R=$CH_3$ with almost complete stereoselectivity, thereby implicating a common oxygen-stabilized C-10 carbocation intermediate. The relative stereochemistry at carbons 9 and 10 was established by the characteristic $^1$H NMR chemical shifts and coupling constants of the methine hydrogen atoms at these positions ($J_{9,10}$=10–11 Hz for trans and $J_{9,10}$=5.6–6.7 Hz for cis). Based on the characteristic $^1$H NMR chemical shifts for analogous C-9,10-disubstituted systems, we conclude that the structure is a 10β-methyl derivative (not shown) (rather than as 9α,10α-dimethyl) and, therefore, that the reaction probably does not proceed via the intermediacy of a C-9, 10-olefin (i.e., via the dehydrofluorinated intermediate). Several dimethyl aluminum acetylides, prepared from $Me_2AlCl$ and the corresponding lithium acetylides, coupled smoothly to form exclusively the 10β-acetylenic derivatives. Di- and tri-methoxylated benzenes and heteroaromatic N-methylpyrrole and furan coupled to produce exclusively, in stereochemical contrast, the 10α-oriented derivatives. Apparently, relatively small nucleophiles approach the intermediate cation from the β-face of the molecule, whereas relatively large aryl and heteroaryl nucleophiles approach from the α-face (i.e. directed by and trans to the C-9 methyl group). Coupling of pyranosyl fluoride VI with N-methylpyrrole proceeded equally well on 400 mg scale as on 20 mg scale, and larger scale executions of this and of the other coupling reactions reported here are not expected to be a problem.

In the course of these studies, it was also discovered that dihydroartemisinin (II-1) itself, like many 1-hydroxy carbohydrates, can be used directly as an electrophile donor in the presence of boron trifluoride-etherate for Friedel-Crafts arylation of reaction aromatics and heteromatics. Consequently, the C-10 carbon-substituted trioxanes of the present invention may be formed according to an alternative embodiment wherein conversion of the pyranose anomeric 10-OH group in dehydroartemisinin with a carbon nucleophile is accomplished by contacting dihydroartemisinin with an electron-rich aromatic or heteroaromatic nucleophile. The chemical yields of the process according to the preferred embodiment versus the second embodiment compare as follows: C-10α glycoside formation using the process of the second embodiment proceeded in 56% yield with 1,3-dimethoxybenzene (vs. 71% using glycosyl fluoride VI) and in 75% yield with N-methylpyrrole (vs. 86% using glycosyl fluoride VI). Although furan did not couple with lactol II-1, furan did couple in 31% yield with fluoride VI. Neither lactol II-1 nor fluoride VI, however, coupled with thiophene.

In summary, it was surprising to learn that the dihydroartemisinin lactol (II-1) as a pyranose sugar with a free anomeric hydroxyl group has led to this two-step protocol involving direct fluorination of readily available lactol II-1 and then C-glycoside formation for easy semi-synthesis of various artemisinin C-10 derivatives VII without destruction of the critical trioxane ring system. These C-10 carbon-substituted trioxanes are expected to be considerably more stable toward hydrolysis than the corresponding ether and ester derivatives (C-10 acetals) of dihydroartemisinin that are currently used clinically as chemotherapeutic antimalarial drugs. The biological activities of C-10 carbon-substituted trioxanes 21 and 22 disclosed below in Table I are discussed in further detail below.

TABLE I

Monomers of the Present Invention (see formula VII)

| Compound No. | n | R = nucleophile | C-10 Stereochemistry |
|---|---|---|---|
| 8 | 1 | —C≡C—Ph | β |
| 9 | 1 | —C≡C—PhCl-p | β |
| 10 | 1 | —C≡C—$C_6H_{13}$ | β |
| 11 | 1 | —C≡C—$SiMe_3$ | β |
| 12 | 1 | —O—∼—O—∼—O—∼—OH | β |
| 13 | 1 | 2,4-dimethoxyphenyl ($H_3CO$, $OCH_3$) | α |
| 14 | 1 | 2,4,6-trimethoxyphenyl (MeO, OMe, OMe) | α |
| 15 | 1 | 3,7-dimethoxynaphthyl (MeO, OMe) | α |
| 16 | 1 | N-methylpyrrolyl (Me—N) | α |
| 17 | 1 | 2-furyl | α |

TABLE II

Dimers of the Present Invention (see formula VII)

| Compound No. | n | R = Linker | C-10 Stereochemistry |
|---|---|---|---|
| 18 | 2 | ~CH2CH2-O-CH2CH2-O-CH2CH2-O-CH2CH2-O-CH2CH2~ | β, β |
| 19 | 2 | ~C(=O)-(CH2)x-C(CH3)2-(CH2)x-C(=O)~, x = 0–2 | β, β |
| 20 | 2 | ~CH2-C(=O)-C(=O)-CH2~ | |
| 21 | 2 | ~C(=O)-1,4-C6H4-C(=O)~ | β, β |
| 22 | 2 | ~C(=O)-1,3-C6H4-C(=O)~ | β, β |
| 23 | 2 | ~C(=O)-(2,6-pyridyl)-C(=O)~ | |
| 24 | 2 | ~C(=O)-C6H4-N(piperazine)N-C6H4-C(=O)~ | |
| 25 | 2 | ~C(=O)-ferrocenyl-C(=O)~ | |
| 26 | 2 | ~2,5-(H3CO,OCH3)-1,4-C6H2~ | α, α |

TABLE II-continued

Dimers of the Present Invention (see formula VII)

| Compound No. | n | R = Linker | C-10 Stereochemistry |
|---|---|---|---|
| 27 | 2 | 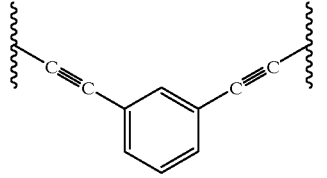 | β, β |
| 28 | 2 |  | β, β |

(↓) and (⌇) designates the point of attachment.

To determine the inhibitory effect of the compositions of the present invention on cell proliferation, screening assays were performed on a murine keratinocyte cell line PE. Cell line PE was chosen for its particular sensitivity to the induction of ornithine decarboxylase (ODC) activity by the extensively characterized tumor promoter TPA. Cell line PE was derived from a papilloma-induced in female SENCAR mice by a standard skin initiation/promotion protocol, see Yuspa, S. H., et al., *Carcinogenesis*, 7:949–958 (1986). PE cell culture medium consisted of Eagle's minimal essential medium without calcium chloride (Whittaker Bioproducts, Walkersville, Mass.) supplemented with 8% chelexed fetal calf serum and 1% antibiotic-antimycotic (Gibco BRL) and the addition of $CaCl_2$ to 0.05 mM $Ca^{++}$.

MTT [3-(4,5-dimethylthiazol-2-yl)-2,5-diphenyltetraxolium bromide] was purchased from Sigma Chemical Co. (St. Louis, Mo.), and TPA was supplied by L.C. Services (Woburn, Mass.). L-[$^{14}$C]ornithine (56 μCi/mol) was from Amersham/Searle Corp. (Arlington Heights, Ill.). Chemical solvents used in all assays of biological activity were of the highest grade commercially available.

Growth Inhibition. Growth curves, shown in FIGS. 1 and 2, for PE cells treated with calcitriol and the C-10 carbon-substituted dimers 21, 22, 26, 27, and 28 generated by assay for the reduction of the tetrazolium-based compound MTT, see Charmichael, et al., *Cancer Res.*, 47:936–942 (1987). A mitochondrial dehydrogenase reduces MTT to a blue formazan product with an absorbance maximum of 505 nm in DMSO; the number of viable cells can thus be determined spectrophotometrically. PE cells were seeded at a density of 5,000 cells/well in 50 μL of medium into 96-well microtiter plates. Twelve hours later, the medium was removed, and cells were treated with 100 μL of fresh medium into which the appropriate amount of calcitrol or analog dissolved in dimethyl sulfoxide (DMSO) had been added, with the concentration of DMSO held constant at 0.1%. The plates were fed once at 48 hours, with the readdition of the C-10 carbon-substituted trioxane dimers 21, 22, 26, 27, and 28 at this time. At 24-hour intervals following the initial treatment of the cells with compounds, 0.1 mg (50 μL of a 2 mg/mL solution) of MTT was added to each well. After 4 hours, the MTT was removed and DMSO added to dissolve the blue formazan dye. Using a microtiter plate reader, the $A_{505}$ was then determined and cell number calculated from blank-subtracted absorbance values. Results from the MTT assay for the inhibition of cell growth were independently confirmed by treating 100-cm$^2$ dishes of cells in an analogous manner for 96 hours, whereupon the cells were harvested by trypsinization and counted. Further, the viability of the cells treated with calcitrol or trioxane dimers was determined to be identical to control cells at 96 hours by trypan blue exclusion.

Antiproliferative activities, measured in vitro using murine keratinocytes as described previously, are shown in FIGS. 1 and 2. Note that the trioxane dimers 21, 22, 26, 27 and 28, even at physiologically relevant 100 nanomolar concentrations, are at least as antiproliferative as calcitrol (1α,25-dihydroxyvitamin $D_3$) that is the hormonally active form of vitamin D and that is used clinically as a drug to treat psoriasis, a skin disorder characterized by uncontrolled proliferation of cells.

To determine the cytotoxicity of the C-10 carbon-substituted trioxane dimers 21 and 22 of the present invention, screening assays were performed by the National Cancer Institute using a 60 cell line panel; some of these activities of trioxane dimers 21 and 22 are summarized in Tables II, III and IV (set out below). The screening assay is performed on a 96-well microtitre plates. Relatively high initial inoculation densities are used, in order to permit measurement of "time-zero" values and to enhance the screen's ability to detect and provide some differentiation between antiproliferative and cytotoxic response parameters. The specific inoculation densities (which range from 5,000 to 40,000 cells/well) used for each cell line are those which, for the respective line, were determined to give an optical density signal for both the "time-zero" value (at 24 hours) and the "no-drug" control (at 72 hours) above the noise level and within the linear range of the end-point assay (which measures cellular protein). The inoculated microtitre plates are pre-incubated for 24 hours at 37° C. prior to drug additions. The five drug dilutions tested routinely range from $10^{-4}$ to $10^{-8}$ molar. Higher or lower concentration ranges may be selected on a nonroutine basis if appropriate solubility and/or prior biological information or other screening data so dictate. Duplicate wells are prepared for all concentrations, (concentration is often denoted by placing brackets around a number); "time-zero" and "no drug" controls are also provided for each test. The minimum amount of compound required for a one-time evaluation in the routine screen can be calculated from the knowledge that each test requires a total of approximately 40 ml (0.04 liter)

of cell culture medium containing the highest desired drug concentration. Thus, the amount (grams) of sample required (assuming an upper test concentration limit of $10^{-4}$ M) is: molecular weight of compound×$10^{-4}$×0.04. After a 48 hour incubation (37° C.) with the test compound, the cells are fixed in situ to the bottoms of the microtitre wells by addition of 50 ul of either 50% trichloroacetic acid (for adherent cell lines) or 80% trichloroacetic acid (for settled cell suspension lines), followed by incubation for 60 minutes at 4° C. The cellular protein in each well is assayed using a sulforhodamine B (SRB) stain procedure. Briefly, after discarding the supernatants, the microtitre plates are washed 5 times with deionized water and air-dried. One hundred microliters of SRB solution (0.4% w/v in 1% acetic acid) is added to each microtitre well and incubated for 10 minutes at room temperature. Unbound SRB is removed by washing 5 times with 1% acetic acid. The plates are air-dried, the bound stain is solubilized with Tris buffer, and the optical densities read at 515 nm. SRB is a bright pink anionic dye which, in dilute acetic acid, binds electrostatically to the basic amino acids of TCA-fixed cells. Cryopreserved master stocks of all the lines are maintained, and cultures used for screening are replaced from the master stock after no more than twenty passages in the screening laboratory. The cell line panel consists of 60 lines, organized into nine, disease-related subpanels including leukemia, non-small-cell lung cancer, colon, CNS, melanoma, ovarian, renal, prostate and breast cancers.

The response parameters $GI_{50}$ and $LC_{50}$ are interpolated values representing the concentrations at which the percentage growth (PG) is +50 and −50, respectively:

$GI_{50}$ is the concentration for which the PG=+50. AT this value the increase from time $t_{zero}$ in the number or mass of cells in the test well is only 50% as much as the corresponding increase in the control well during this period of the experiment, see Table III. A drug effect of this intensity is interpreted as primary growth inhibition.

TGI is the concentration for which PG=0. At this value or mass of cells in the well as the end of the experiment equals the number or mass of cells in the well at time $t_{zero}$, see Table IV. A drug effect of this intensity is regarded as cytostasis.

$LC_{50}$ is the concentration for which the PG=−50. At this value, the number or mass of cells in the test well at the end of the experiment is half that at time $t_{zero}$, see Table V. This is interpreted as cytotoxicity.

TABLE III

| | | $Log_{10}GI_{50}$ | | | |
|---|---|---|---|---|---|
| Panel/ | | C-10 Carbon-Substituted Trioxane Dimers | | | |
| Cell Line | Artemisinin | Compond VI | Dimer 21 | Dimer 22 | Paclitaxel |
| Leukemia | | | | | |
| CCRP-CEM | — | −6.25 | <−8.00 | >−4.00 | −11.61 |
| HL-60(TB) | −4.26 | — | <−8.00 | >−4.00 | −11.57 |
| K-562 | −4.33 | −6.50 | <−8.00 | >−4.00 | −10.83 |
| MOLT-4 | −4.73 | −6.37 | <−8.00 | >−4.00 | −11.07 |
| RPMI-8226 | >−4.00 | — | <−8.00 | >−4.00 | <−13.00 |
| SR | >−4.00 | −6.37 | <−8.00 | >−4.00 | 8.34 |
| Non-Small Cell Lung Cancer | | | | | |
| A549/ATCC | −4.17 | −5.22 | <−8.00 | >−4.00 | — |
| EKVX | >−4.00 | −5.53 | −5.94 | >−4.00 | −9.67 |
| HOP-62 | >−4.00 | −4.89 | −6.38 | >−4.00 | — |
| HOP-92 | >−4.00 | −5.53 | −7.15 | >−4.00 | — |
| NCI-H226 | >−4.00 | −5.24 | −7.08 | −4.53 | — |
| NCI-H23 | >−4.00 | −6.20 | −7.92 | >−4.00 | −10.12 |
| NCI-H322M | — | −4.97 | −5.42 | >−4.00 | −12.16 |
| NCI-H460 | >−4.00 | −6.09 | −6.28 | >−4.00 | <−13.00 |
| NCI-H522 | — | −6.07 | <−8.00 | >−4.00 | — |
| Colon Cancer | | | | | |
| COLO 205 | >−4.00 | — | <−8.00 | >−4.00 | −11.07 |
| HCT-116 | −4.00 | −6.71 | <−8.00 | >−4.00 | <−13.00 |
| HCT-15 | >−4.00 | −6.47 | — | >−4.00 | −6.37 |
| HT29 | >−4.00 | −6.39 | <−8.00 | >−4.00 | <−13.00 |
| KM12 | >−4.00 | −6.36 | <−8.00 | >−4.00 | −11.43 |
| SW-620 | >−4.00 | −6.40 | <−8.00 | >−4.00 | −11.60 |
| HCC-2998 | — | −4.84 | — | — | — |
| CNS Cancer | | | | | |
| SF-268 | — | −4.86 | −7.20 | >−4.00 | — |
| SF-295 | — | −4.77 | −5.32 | >−4.00 | — |
| SF-539 | — | −4.85 | −7.78 | >−4.00 | −11.09 |
| SNB-19 | >−4.00 | −3.06 | −6.27 | >−4.00 | −8.98 |
| SNB-75 | >−4.00 | −4.84 | −6.93 | −5.36 | — |
| U251 | >−4.00 | −6.35 | <−8.00 | >−4.00 | −11.29 |
| Melanoma | | | | | |
| LOX IMVI | — | −6.45 | <−8.00 | >−4.00 | −11.80 |
| MALME-3M | — | −5.63 | −7.33 | >−4.00 | — |
| M14 | — | −4.76 | −5.90 | >−4.00 | −11.73 |
| SK-MEL-2 | — | −5.12 | −7.41 | >−4.00 | −9.53 |
| SK-MEL-28 | >−4.00 | −4.75 | −4.97 | >−4.00 | — |
| UACC-257 | >−4.00 | — | −7.68 | >−4.00 | −10.30 |

TABLE III-continued

$Log_{10}GI_{50}$

| Panel/ | | C-10 Carbon-Substituted Trioxane Dimers | | | |
|---|---|---|---|---|---|
| Cell Line | Artemisinin | Compond VI | Dimer 21 | Dimer 22 | Paclitaxel |
| UACC-62 | >−4.00 | −5.63 | −7.14 | >−4.00 | −10.46 |
| SK-MEL-5 | — | −6.31 | — | — | — |
| Ovarian Cancer | | | | | |
| IGROVI | −4.31 | −5.91 | −5.97 | −6.23 | −8.61 |
| OVCAR-3 | — | −5.54 | −6.16 | >−4.00 | −10.40 |
| OVCAR-4 | — | — | −5.80 | >−4.00 | −5.00 |
| OVCAR-5 | >−4.00 | −4.77 | <−8.00 | — | −9.38 |
| OVCAR-8 | >−4.00 | −5.69 | <−8.00 | >−4.00 | −10.75 |
| SK-OV-3 | — | −4.62 | −3.58 | >−4.00 | — |
| Renal Cancer | | | | | |
| 786-0 | >−4.00 | −5.81 | −7.82 | >−4.00 | −8.01 |
| A498 | >−4.00 | −4.55 | −5.74 | −4.33 | −7.14 |
| ACHN | >−4.00 | −5.99 | −7.71 | >−4.00 | — |
| CAKI-1 | — | −3.14 | −7.95 | >−4.00 | — |
| RXF 393 | −4.08 | −4.83 | −5.59 | >−4.00 | −8.32 |
| SN12C | −4.21 | −5.97 | −7.98 | >−4.00 | −9.53 |
| TK-10 | >−4.00 | −4.96 | −8.54 | >−4.00 | −7.89 |
| UO-31 | −4.06 | −5.96 | −7.62 | >−4.00 | −6.09 |
| Prostate Cancer | | | | | |
| PC-3 | −4.17 | −6.60 | <−8.00 | >−4.00 | −10.85 |
| DU-145 | — | −4.71 | −5.20 | >−4.00 | −9.38 |
| Breast Cancer | | | | | |
| MCF7 | >−4.00 | −6.28 | <−8.00 | −6.41 | −11.69 |
| MCF7/ADR-RES | — | −5.45 | −7.98 | >−4.00 | −8.48 |
| MDA-MB231/ATCC | −4.20 | −4.88 | −6.75 | >−4.00 | −8.54 |
| HS 578T | >−4.00 | — | <−8.00 | >−4.00 | — |
| MDA-MB-435 | — | −6.16 | <−8.00 | >−4.00 | <−13.00 |
| MDA-N | >−4.00 | −5.94 | −7.97 | >−4.00 | <−13.00 |
| BT-549 | −4.06 | −6.12 | −6.58 | >−4.00 | −9.31 |
| T-47D | — | −6.52 | <−8.00 | >−4.00 | −9.81 |
| MG MID | — | −5.63 | −7.23 | −4.12 | — |
| Delta | −4.07 | 1.08 | 0.77 | 2.20 | −10.15 |
| Range | 0.73 | 2.16 | 9.03 | 2.41 | 8.00 |

TABLE IV

$Log_{10}TGI$

| Panel/ | | C-10 Carbon-Substituted Trioxane Dimers | | | |
|---|---|---|---|---|---|
| Cell Line | Artemisinin | Compond VI | Dimer 21 | Dimer 22 | Paclitaxel |
| Leukemia | | | | | |
| CCRF-CEM | — | −4.27 | −1.34 | >−4.00 | >−4.00 |
| HL-60(TB) | −4.00 | — | −5.97 | >−4.00 | >−4.53 |
| K-562 | −4.00 | −4.90 | | >−4.00 | >−4.00 |
| MOLT-4 | −4.00 | −4.44 | −4.89 | >−4.00 | >−4.00 |
| RPMI-8226 | >−4.00 | — | <−8.00 | >−4.00 | >−4.00 |
| SR | >−4.00 | −4.86 | >−4.00 | >−4.00 | |
| Non-Small Cell Lung Cancer | | | | | |
| A549/ATCC | >−4.00 | −4.51 | −4.87 | >−4.00 | — |
| EKVX | >−4.00 | −4.05 | −4.58 | >−4.00 | — |
| HOP-62 | >−4.00 | −4.21 | −4.76 | >−4.00 | −4.80 |
| HOP-92 | >−4.00 | −4.67 | −4.76 | >−4.00 | — |
| NCI-H226 | >−4.00 | >−4.00 | −4.55 | >−4.00 | — |
| NCI-H23 | >−4.00 | −4.60 | >−4.00 | >−4.00 | — |
| NCI-H322M | — | >−4.00 | >−4.00 | >−4.00 | −4.46 |
| NCI-H460 | >−4.00 | −4.72 | >−4.00 | >−4.00 | −4.92 |
| NCI-H522 | — | −4.78 | −4.55 | >−4.00 | −11.20 |
| Colon Cancer | | | | | |
| COLO 205 | >−4.00 | — | −7.39 | >−4.00 | — |

TABLE IV-continued

| | Log₁₀TGI | | | | |
|---|---|---|---|---|---|
| Panel/ | | C-10 Carbon-Substituted Trioxane Dimers | | | |
| Cell Line | Artemisinin | Compond VI | Dimer 21 | Dimer 22 | Paclitaxel |
| HCT-116 | >−4.00 | >−4.00 | −4.90 | >−4.00 | −4.82 |
| HCT-15 | >−4.00 | −4.29 | −4.61 | >−4.00 | >−4.00 |
| HT29 | >−4.00 | >−4.00 | −4.82 | >−4.00 | — |
| KM12 | >−4.00 | −4.57 | −4.84 | >−4.00 | −4.36 |
| SW-620 | >−4.00 | −4.81 | −4.06 | >−4.00 | >−4.00 |
| HCC-2998 | — | −4.89 | — | — | — |
| CNS Cancer | | | | | |
| SF-268 | — | >−4.00 | −4.10 | >−4.00 | — |
| SF-295 | — | >−4.00 | −4.60 | >−4.00 | — |
| SF-539 | — | −4.39 | −4.84 | >−4.00 | — |
| SNB-19 | >−4.00 | >−4.00 | −4.38 | >−4.00 | >−4.00 |
| SNB-75 | >−4.00 | >−4.00 | −4.46 | >−4.00 | — |
| U251 | >−4.00 | −4.79 | −4.77 | >−4.00 | −4.32 |
| Melanoma | | | | | |
| LOX IMVI | — | −3.56 | −4.92 | >−4.00 | −4.65 |
| MALME-3M | −4.06 | >−4.00 | −4.55 | >−4.00 | −4.46 |
| M14 | >−4.00 | >−4.00 | −4.75 | >−4.00 | −4.62 |
| SK-MEL-2 | >−4.00 | −4.11 | −6.26 | >−4.00 | — |
| SK-MEL-28 | >−4.00 | >−4.00 | >−4.00 | >−4.00 | — |
| UACC-257 | >−4.00 | >−4.00 | −4.75 | >−4.00 | −4.52 |
| UACC-62 | >−4.00 | >−4.00 | −4.56 | >−4.00 | −4.71 |
| SK-MEL-5 | — | −4.87 | | | |
| Ovarian Cancer | | | | | |
| IGROVI | >−4.00 | −4.74 | −4.92 | >−4.00 | −4.19 |
| OVCAR-3 | — | >−4.00 | −4.55 | >−4.00 | −4.55 |
| OVCAR-4 | — | — | >4.00 | >−4.00 | −4.19 |
| OVCAR-5 | >−4.00 | >−4.00 | −4.84 | >−4.00 | −4.92 |
| OVCAR-8 | >−4.00 | −4.29 | −4.91 | >−4.00 | — |
| SK-OV-3 | — | >−4.00 | −4.67 | >−4.00 | — |
| Renal Cancer | | | | | |
| 786-0 | >−4.00 | −4.83 | −4.83 | >−4.00 | >−4.00 |
| A498 | >−4.00 | >−4.00 | −4.72 | >−4.00 | — |
| ACHN | >−4.00 | −4.90 | −4.16 | >−4.00 | −4.90 |
| CAKI-1 | — | −4.67 | −7.05 | >−4.00 | −4.04 |
| RXF 393 | >−4.00 | >−4.00 | −4.71 | >−4.00 | >−4.00 |
| SN12C | >−4.00 | >−4.00 | −4.91 | >−4.00 | −4.29 |
| TK-10 | >−4.00 | −4.43 | >−4.00 | >−4.00 | — |
| UO-31 | −4.00 | −5.30 | −4.24 | >−4.00 | — |
| Prostate Cancer | | | | | |
| PC-3 | >−4.00 | −4.33 | −4.94 | >−4.00 | >−4.00 |
| DU-145 | — | >−4.00 | −4.50 | >4.00 | >−4.00 |
| Breast Cancer | | | | | |
| MCF7 | >−4.00 | >−4.00 | −4.88 | >−4.00 | −4.05 |
| MCF7/ADR-RES | — | >−4.00 | −4.85 | >−4.00 | >−4.00 |
| MDA-MB231/ATCC | −4.00 | −4.25 | −4.79 | >−4.00 | −4.84 |
| HS 578T | >−4.00 | — | −4.82 | >−4.00 | — |
| MDA-MB-435 | — | −5.14 | −4.60 | >−4.00 | — |
| MDA-N | >−4.00 | −4.67 | −5.24 | >−4.00 | — |
| BT-549 | −4.00 | −4.51 | −4.31 | >−4.00 | −6.32 |
| T-47D | >−4.00 | −4.32 | −5.59 | >−4.00 | −4.05 |
| MG MID | — | −4.38 | −1.03 | −4.00 | — |
| Delta | −4.00 | 1.18 | 3.17 | 0.00 | −4.54 |
| Range | 0.06 | 1.56 | 4.00 | 0.00 | 7.20 |

*NCI indicates these values are not relevant

TABLE V

| | $Log_{10}LC_{50}$ | | | | |
|---|---|---|---|---|---|
| Panel/ | | C-10 Carbon-Substituted Trioxane Dimers | | | |
| Cell Line | Artemisinin | Compond VI | Dimer 21 | Dimer 22 | Paclitaxel |
| Leukemia | | | | | |
| CCRF-CEM | — | >4.00 | >−4.00 | >−4.00 | >−4.00 |
| HL-60(TB) | >−4.00 | — | >−4.00 | >−4.00 | >−4.53 |
| K-562 | >−4.00 | >−4.00 | >−4.00 | >−4.00 | >−4.00 |
| MOLT-4 | >−4.00 | >−4.00 | >−4.00 | >−4.00 | >−4.00 |
| RPMI-8226 | >−4.00 | — | >−4.00 | >−4.00 | >−4.00 |
| SR | >4.00 | >−4.00 | >−4.00 | >−4.00 | >−4.00 |
| Non-Small Cell Lung Cancer | | | | | |
| A549/ATCC | >−4.00 | >−4.00 | −4.43 | >−4.00 | — |
| EKVX | >−4.00 | >−4.00 | >−4.00 | >−4.00 | — |
| HOP-62 | >−4.00 | >−4.00 | −4.28 | >−4.00 | −4.10 |
| HOP-92 | >−4.00 | >−4.00 | −4.08 | >−4.00 | — |
| NCI-H226 | >−4.00 | >−4.00 | >−4.00 | >−4.00 | — |
| NCI-H23 | >−4.00 | >−4.00 | >−4.00 | >−4.00 | — |
| NCI-H322M | — | >−4.00 | >−4.00 | >−4.00 | >−4.00 |
| NCI-H460 | >−4.00 | −4.26 | >−4.00 | >−4.00 | >−4.00 |
| NCI-H522 | — | −4.19 | >−4.00 | >−4.00 | >−4.00 |
| Colon Cancer | | | | | |
| COLO 205 | >−4.00 | — | −7.12 | >−4.00 | >−4.41 |
| HCT-116 | >−4.00 | −4.37 | −4.29 | >−4.00 | >−4.00 |
| HCT-15 | >−4.00 | >−4.00 | >−4.00 | >−4.00 | >−4.00 |
| HT29 | >−4.00 | >−4.00 | −4.27 | >−4.00 | −4.39 |
| KM12 | >−4.00 | >−4.00 | −4.29 | >−4.00 | >−4.00 |
| SW-620 | >−4.00 | −4.20 | >−4.00 | >−4.00 | >−4.00 |
| HCC-2998 | — | >−4.00 | | | |
| CNS Cancer | | | | | |
| SF-268 | — | >−4.00 | >−4.00 | >−4.00 | — |
| SF-295 | — | >−4.00 | −4.11 | >−4.00 | — |
| SF-539 | — | >−4.00 | −4.42 | >−4.00 | >−4.00 |
| SNB-19 | >−4.00 | >−4.00 | >−4.00 | >−4.00 | >−4.00 |
| SNB-75 | >−4.00 | >−4.00 | >−4.00 | >−4.00 | — |
| U251 | >−4.00 | −4.37 | −4.38 | >−4.00 | −4.15 |
| Melanoma | | | | | |
| LOX IMVI | — | −4.5o | −4.31 | >−4.00 | >−4.15 |
| MALME-3M | >−4.00 | >−4.00 | >−4.00 | >−4.00 | −4.11 |
| M14 | >−4.00 | >−4.00 | −4.34 | >−4.00 | −4.13 |
| SK-MEL-2 | >−4.00 | >−4.00 | −4.60 | >−4.00 | >−4.00 |
| SK-MEL-28 | >−4.00 | >−4.00 | >−4.00 | >−4.00 | — |
| UACC-257 | >−4.00 | >−4.00 | >−4.00 | >−4.00 | −4.03 |
| UACC-62 | >−4.00 | >−4.00 | −4.02 | >−4.00 | −4.19 |
| SK-MEL-5 | — | −4.21 | — | — | — |
| Ovarian Cancer | | | | | |
| IGROVI | >−4.00 | −4.24 | −4.15 | >−4.00 | >−4.00 |
| OVCAR-3 | — | >−4.00 | >−4.00 | >−4.00 | >−4.00 |
| OVCAR-4 | — | — | >4.00 | >−4.00 | >−4.00 |
| OVCAR-5 | >−4.00 | >−4.00 | −4.22 | >−4.00 | >−4.00 |
| OVCAR-8 | >−4.00 | >−4.00 | −4.38 | >−4.00 | >−4.00 |
| SK-OV-3 | — | >−4.00 | −4.28 | >−4.00 | |
| Renal Cancer | | | | | |
| 786-0 | >−4.00 | −4.39 | −4.42 | >−4.00 | >−4.00 |
| A498 | >−4.00 | >−4.00 | −4.19 | >−4.00 | −4.13 |
| ACHN | >−4.00 | −4.41 | >−4.00 | >−4.00 | −4.45 |
| CAKI-1 | — | −4.32 | −4.56 | >−4.00 | >−4.00 |
| RXF 393 | >−4.00 | >−4.00 | −4.31 | >−4.00 | >−4.00 |
| SN12C | >−4.00 | >−4.00 | −4.07 | >−4.00 | >−4.00 |
| TK-10 | >−4.00 | >−4.00 | >−4.00 | >−4.00 | — |
| UO-31 | >−4.00 | −4.60 | >−4.00 | >−4.00 | — |
| Prostate Cancer | | | | | |
| PC-3 | >−4.00 | >−4.00 | −4.32 | >−4.00 | >−4.00 |
| DU-145 | — | >−4.00 | >−4.00 | >−4.00 | >−4.00 |
| Breast Cancer | | | | | |
| MCF7 | >−4.00 | >−4.00 | −4.27 | >−4.00 | >−4.00 |
| MCF7/ADR- | — | >−4.00 | −4.10 | >−4.00 | >−4.00 |

TABLE V-continued

| | $Log_{10}LC_{50}$ | | | | |
|---|---|---|---|---|---|
| Panel/ | | C-10 Carbon-Substituted Trioxane Dimers | | | |
| Cell Line | Artemisinin | Compond VI | Dimer 21 | Dimer 22 | Paclitaxel |
| RES | | | | | |
| MDA-MB231/ATCC | >−4.00 | >−4.00 | −4.33 | >−4.00 | −4.29 |
| HS 578T | >−4.00 | — | −4.14 | >−4.00 | — |
| MDA-MB-435 | — | −4.46 | >−4.00 | >−4.00 | — |
| MDA-N | >−4.00 | >−4.00 | −4.40 | >−4.00 | — |
| BT-549 | >−4.00 | >−4.00 | >−4.00 | >−4.00 | >−4.00 |
| T-47D | >−4.00 | >−4.00 | >−4.00 | >−4.00 | >−4.00 |
| MG MID | — | −4.03 | −4.19 | −4.00 | — |
| Delta | −4.00 | 0.52 | 2.93 | 0.00 | −4.06 |
| Range | 0.00 | 0.60 | 3.12 | 0.00 | 0.45 |

The C-10 carbon-substituted trioxane dimer 21 of the present invention and compound VI of the present invention in most instances are as potent and in some instances more potent than paclitaxel. The data in Tables III, IV and V are graphically represented in FIGS. 3a, b, c, d, and e through FIGS. 11e. Dose response curves, shown in the above mentioned Figures, are obtained by exposing various cancer cell lines to compounds having a known concentration ($[log_{10}$ M]), as discussed in detail above, and then plotting the percentage growth of each cell line for each concentration. The drug concentration limits that are tested are between $10^{-4}$ or −4.00M and $10^{-9}$ or −9.00M. The −4.00M value being the high concentration and the −9.00M value being the low concentration. Percentage growth is determined by dividing the number or mass of cells in the test well by the number or mass of cells in a control well. Referring to the leukemia cell line MOLT-4 in FIGS. 3a, 3b, 3c, 3d, and 3e the first comparison that is made between artemisinin, paclitaxel, compound VI and the C-10 carbon-substituted trioxane dimers 21 and 22 of the present invention are the drug concentrations which are necessary to inhibit growth, graphically represented in FIGS. 3a, 3b, 3c, 3d, and 3e as the concentration necessary to achieve the percentage growth value of +50. As discussed previously, the five drug dilutions routinely tested range from $10^{-4}$ to $10^{-9}$ molar. Therefore, concentrations less than or greater than $10^{-9}$ and $10^{-4}$ molar, respectively, that are required to achieve a desired result are not determined. Referring now to FIG. 3a, some concentration of paclitaxel that is less than $10^{-8}$M is necessary to achieve primary growth inhibition; in fact the lower concentrations have been determiend for this drug and the concentration at which primary growth inhibition occurs using paclitaxel is at $10^{-11}$ molar. FIG. 3b indicates that some concentration of artemisinin that is greater than $10^{-4}$ molar is necessary to achieve primary growth inhibition. Referring to the C-10 carbon-substituted trioxane dimers 21 and 22 dose response curves in FIGS. 3c and 3d, respectively, the leukemia cell line MOLT-4 displays primary growth inhibition at drug concentrations that are less than $10^{-7}$ and greater than $10^{-4}$, respectively, and compound VI displays primary growth inhibition at a concentration of about $10^{-7}$ molar. The drug concentration at which artemisinin is considered cytostatic, i.e. percentage growth is equal to 0, is at a concentration greater than $10^{-4}$ molar. The C-10 carbon-substituted trioxane dimers 21 and 22 reach cytostasis at drug concentrations of approximately $10^{-4}$M, and at some concentration greater than $10^{-4}$M, respectively, while the paclitaxel concentration necessary to achieve cytostasis is some value greater than $10^{-4}$M. Compound VI reaches cytostasis at a concentration between $10^{-4}$M and $10^{-3}$M. Cytotoxicity, i.e., the concentration for which the percentage growth is equal to −50, occurs at a concentration greater than $10^{-4}$M for paclitaxel, artemisinin, compound VI, and for both C-10 carbon-substituted trioxane dimers 21 and 22.

The potency of the C-10 carbon-substituted trioxane dimer 21 of the present invention, and compound VI, as compared to artemisinin and paclitaxel varies from cell line to cell line. The mean values for each drug are presented at the end of Tables III, IV and V and the C-10 carbon-substituted trioxane dimer 21 of the present invention and compound VI are more potent than artemisinin and equivalent to and in many instances higher in potency than paclitaxel.

The dihydroartemisinin condensation by-product disclosed by M. Cao et al., and tested by D. L. Klayman and H. J. Woerdenbag, discussed previously, was approximately twenty-two times more potent at 50% growth inhibition in one cancer cell line than artemisinin. With respect to the drug concentrations causing 50% growth inhibition, the dimer 21 was at least 100 times more potent than artemisinin. When interpreting the mean values, it is important to take into consideration that drug concentrations less than $10^{-9}$M and greater than 10M were not collected, and this factor is reflected in the range.

For a further comparison on the effects of the trioxane dimers of the present invention on various cancer cell lines versus the effects of artemisinin and paclitaxel on the same cell lines see FIGS. 4a, b, c, d and e for non-small cell lung cancer cell lines, FIGS. 5a, b, c, d and e for colon cancer cell lines, FIGS. 6a, b, c, d and e for CNS cancer cell lines, FIGS. 7a, b, c, d and e for melanoma cancer cell lines, FIGS. 8a, b, c, d and e for ovarian cancer cell lines FIGS. 9a, b, c, d and e for renal cancer cell lines, FIGS. 10a, c, d and e for prostate cancer cell lines and FIGS. 11a, c, d and e for breast cancer cell lines.

To determine the antimalarial effect of various C-10 carbon-substituted monomers, and dimers 21 and 22 of the present invention, screening assays were performed against chloroquine-sensitive *P. falciparum* (NF54), according to the method described below.

Determination of Antimalarial Activity

Activity was determined by measuring the incorporation of [$^3$H]hypoxanthine, by the methods of Desjardins and Milhouse, with the following modofications, see Desjardins, R. E.; Canfield, C. J.; Haynes, J. D.; Chulay, J. D. *Antimi-* crob. Agents Chemother., 16:710 (1979); Milhous, W. K.; Weatherly, N. F.; Bowdre, J. H.; Desjardins, R.; Antimicrob. Agents Chemother., 27: 525 (1985). Chloroquine-sensitive P. falciparum (NF54 strain) were maintained in a 2.4% suspension of type $O^+$ human erythrocytes (obtained weekly from a rotating pool of screened healthy volunteers) in RPMI 1640 (Gibco BRL #13200-076), supplemented with 25 mM N-2-hydroxyethylpiperazine-N'-2-ethanesulfonic acid (HEPES; Calbiochem #391338), 27 mM $NaHCO_3$ (Gibco BRL #11810-025), and 10% heat-inactivated human type $O^+$ serum (Interstate Blood Bank, Inc.), under 3% $O_2$, 4% $CO_2$, and 93% $N_2$. Parasitemia was maintained at 0.05–3% and doubling time at approximately 15 hours by twice weekly change of medium and replenishment with fresh erythrocytes.

Stock solutions (approximately 2.5 mg/mL of HPLC-purifed or recrystallized test compound) were prepared in dimethyl sulfoxide (DMSO; Sigma-Aldrich #27,043-1). DMSO solutions were diluted 500-fold in medium, serially diluted in 0.2% DMSO in medium (to maintain constant solvent concentration), then 100 µL aliquots were pipetted into microtiter plate wells (Costar 3595). Provisional $EC_{50}$ values were obtained in a survey of seven 5-fold dilutions yielding final concentrations (in triplicate) of 0.16–2500 ng/mL. Assays were later expanded to include ten concentrations (in quadruplicate) of approximately 1.8-fold dilutions which flank the provisional $EC_{50}$. Plates included at least 8 wells of no drug controls (4 with and 4 without DMSO) and 4 wells of uninfected erythrocytes. Parasite culture (0.25% parasitemia in 2.4% hematocrit; 100 µL per well) was added and the plate was incubated for 48 hours prior to the addition fo 25 µL [$^3$H]hypoxanthine (14.1 Ci/mmol, 1 mCi/mL in 70% ethanol, New England Nuclear NET-177, diluted to 25 µCi/mL with medium) and subsequent 20 hour incubation. Cells were harvested (Brandel MB-48R) onto GF-C glass filters (Brandel). The filters were washed five times with 3 mL water per sample spot, dried under a heat lamp, and counted (Beckman Model LS-6500) in scintillation cocktail (ICN Cytoscint).

Decays per minute (dpm) values were downloaded and analyzed (Power MFacintosh 7200/90; Microsoft Excel 5.0), to yield the mean and standard deviation at each drug concentration. Dose-response curves were fit to the experimental data (Delta Point DeltaGraph 3.5.3) by means of the Marquardt algorithm, were solved for the drug concentration that kills 50% of parasites, and were analyzed for goodness of fit ($R^2$ value).

The preliminary data summarizing the activities of C-10 carbon-substituted monomers 8–11 and 13–17, and dimers 21 and 22 are represented in Table VI, below.

TABLE VI

| In Vitro Antimalarial Activities | C-10 Stereo-chemistry | $IC_{50}$ (nM) |
|---|---|---|
| Artemisinin | | 10 |
| Artemether | | 5.4 |
| Monomer 8 | β | t |
| Monomer 9 | β | 16[s] |
| Monomer 10 | β | t |
| Monomer 11 | β | t |
| Monomer 13 | α | 8.9[s] |
| Monomer 14 | α | 11[s] |
| Monomer 15 | α | 11[s] |
| Monomer 16 | α | 8.4[s] |
| Monomer 17 | α | 1.5[s] |

TABLE VI-continued

| In Vitro Antimalarial Activities | C-10 Stereo-chemistry | $IC_{50}$ (nM) |
|---|---|---|
| p-Dimer 21 | β, β | 1.9 |
| m-Dimer 22 | β, β | 1.9 | t = to be tested
[e]Expansion data.
[s]survey data (preliminary).

Artemether and the C-10 carbon-substituted trioxane monomers 13, 16 and 17, and dimers 21 and 22 have $IC_{50}$ values lower than that of artemisinin thus indicating that these compounds are more potent than artemisinin.

The invention is further illustrated by the following non-limited examples. All scientific and technical terms have the meanings as understood by one with ordinary skill in the art. The specific examples which follow illustrate the synthesis of representative compounds of the instant invention and are not to be construed as limiting the invention in sphere or scope. The methods may be adapted to variation in order to produce compounds embraced by this invention but not specifically disclosed. Further, variations of the methods to produce the same comounds in somewhat different fashion will be evident to one skilled in the art.

EXAMPLES

Unless otherwise noted, reactions were run in flame-dried round-bottomed flasks under an atmosphere of ultra high purity (UHP) argon. Diethyl ether (ether) and tetrahydrofuran (THF) were distilled from sodium benzophenone ketyl prior to use. Dichloromethane ($CH_2Cl_2$) and triethylamine (TEA) were distilled from calcium hydride prior to use. All other compounds were purchased from Aldrich Chemical Company and used without further purification. All temperatures are understood to be in Centigrade (0° C.) when not specified. Analytical thin-layer chromatography (t.l.c.) was conducted with Silica Gel 60 $F_{254}$ plates (250 micrometer thickness, Merck). Column chromatography was performed using short path silica gel (particle size<230 mesh), flash silica gel (particle size 400–230 mesh), or Florisil® (200 mesh). Yields are not optimized. High performance liquid chromatography (HPLC) was carried out with a Rainin HPLX system equipped with two 25 mL/min preparative pump heads using Rainin Dynamax 10 mm×250 mm (semi-preparative) columns packed with 60 Å silica gel (8 µm pore size), either as bar silica or as C-18-bonded silica. Melting points were measured using a Mel-Temp metal-block apparatus and are uncorrected. Nuclear magnetic resonance (NMR) spectra were obtained either on a Varian XL-400 spectrometer, operating at 400 MHz for $^1$H and 100 MHz for $^{13}$C or a varian XL-500 spectrometer, operating at 500 Mhz for $^1$H and 125 MHz for $^{13}$C. Chemical shifts are reported in parts per million (ppm, δ) downfield from tetramethylsilane. Splitting patterns are described as singlet (s), doublet (d), triplet (t), quarter (q), multiplet (m), and broad (b). The solvents employed for taking NMR spectra are DMSO-$d_6$ (perdeuterodimethysulfoxide), $D_2O$ (deuterated water), $CDCl_3$ (deuterochloroform) and other conventional deuterated solvents. Combination of $CH_3CN$ and $H_2O$ in different concentrations are used as HPLC solvent system. Infrared (IR) spectra were obtained using a Perkin-Elmer 1600 FT-IR spectrometer. Resonances are reported in wavenumbers ($cm^{-1}$). Low resolution (LRMS) and high resolution (HRMS) mass spectra were obtained on a VG Instruments 70-S spectrometer run at 70 eV for concentration ionization (EI) and run with ammonia ($NH_3$)

as a carrier for chemical ionization (CI). Combustion analyses were conducted by Atlantic Microlab (Norcross, Ga.). Various methods of purifying the products of the present invention are known and understood by those skilled in the art and the purification methods presented in the Examples is solely listed by way of example and is not intended to limit the invention.

The synthetic descriptions and specific examples that follow are only intended for the purposes of illustration, and are not to be construed as limiting in any manner to make compounds of the present invention by other methods.

Example I

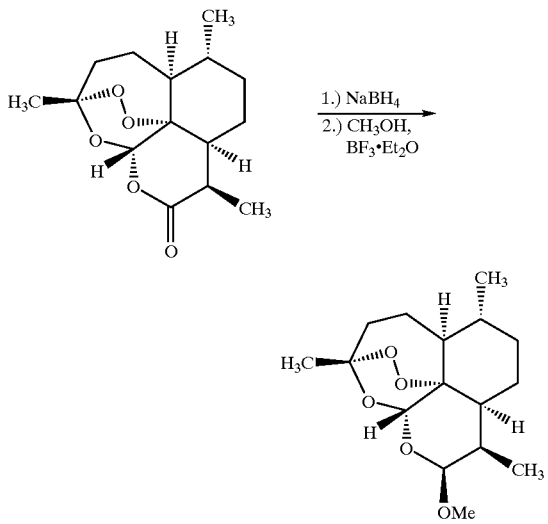

To a solution of artemisinin (0.34 g, 1.24 mmol) in methanol (25 mL) and THF (5 mL) at −15° C. was added sodium borohydride (0.34 g, 9.30 mmol) in four equal portions over 1 hour. The resulting reaction mixture was stirred at −15° C. for 2 hours and quenched with glacial acetic acid (0.55 mL, 9.60 mmol) at −15° C.

To the mixture at room temperature was added water (30 mL) and CH$_2$Cl$_2$ (30 mL). The two layers were separated, and the aqueous phase was extracted with CH$_2$Cl$_2$ (30×2 mL). The combined organic layers were washed with brine, dried over magnesium sulfate, filtered and concentrated under reduced pressure to afford crude dihydroartemisinin white solid: mp 149°–153° C.

To a solution of the crude dihydroartemisinin in chloroform (40 mL) and methanol (1 mL, 24.8 mmol) was added boron trifluoride etherate (0.16 mL, 1.24 mmol) at 0° C. The reaction was stirred at 0° C. for 15 minutes, slowly warmed up to room temperature and stirred at room temperature for 3 hours. The reaction was monitored by TLC until all starting material was consumed. The reaction mixture was quenched with water (50 mL) and diluted with chloroform (25 mL). The two phases were separated, and the aqueous layer was extracted with chloroform (30×2 mL). The combined organic layers were washed with brine, dried over magnesium sulfate, filtered and concentrated under reduced pressure to afford crude product which was further purified by column chromatography on Florisil (1%–10% EtOAc/hexanes) to give two artemisinin isomers as white solids: β-isomer (0.29 g, 0.98 mmol, 79%) mp 73°–74.5° C.; α-isomer (0.05 g, 0.17 mmol, 14%), with each having a $^1$H NMR spectrum identical to that reported in the literature.

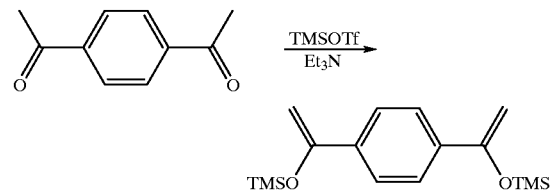

To a stirred solution of diacetylbenzene (1 eq.), ether and THF at room temperature was added TEA (2.2 eq.) via gas-tight syringe. Trimethylsilyl trifluoromethanesulfonate (TMSOTf; 2.2 eq.) was slowly added to the reactio mixture at room temperature via gas-tight syringe. The resulting mixture was stirred at room temperature for 2 hours.

The two layers were separated, and the top layer was concentrated under reduced pressure. The mixture was diluted with dry ether (30 mL) and filtered. The resulting filtrate was concentrated under reduced pressure to provide crude product as light yellow oil. Purification by Kügelrohr afforded the desired product that was used immediately for coupling with β-artemether. bis-TMS-enol ether of 1,4-diacetylbenzene (1.50 g, 4.89 mmol, 49% yield) was prepared as a colorless oil: $^1$H NMR (CDCl$_3$) δ7.56 (s, 4H), 4.95 (d, J=1.8 Hz, 2H) 4.45 (d, J=1.8 Hz, 2H), 0.29 (s, 18H); $^{13}$C NMR (CDCl$_3$) δ155.26, 137.22, 124.88, 91.30, 0.11.

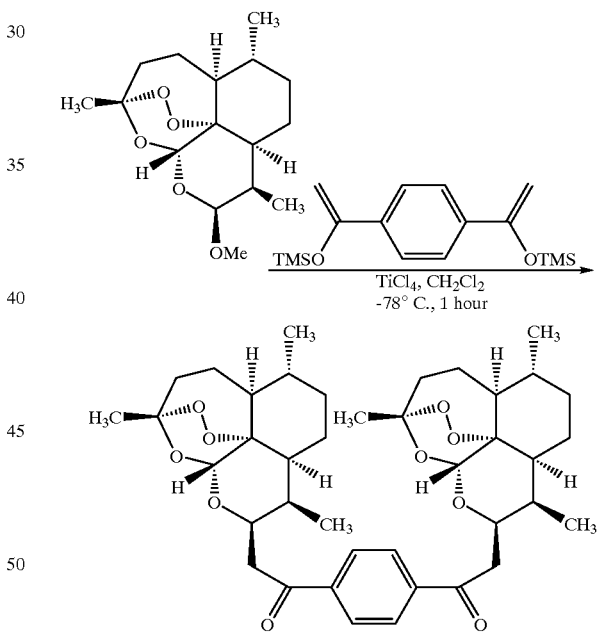

To a stirred solution of β-artemether (1 eq.) in CH$_2$Cl$_2$ at −78° C. added a 1M solution of TiCl$_4$ in CH$_2$Cl$_2$ (1.1 eq.) via gas-tight syringe. A solution of the bis-TMS-enol ether (0.55 eq.) in CH$_2$Cl$_2$ at room temperature was then added to the reaction mixture via gas-tight syringe. The resulting reaction mixture was stirred at −78° C. for 1 hour.

The reaction was quenched at −78° C. with water (3 mL) and diluted with ether (5 mL). The two layers were separated, and the aqueous phase was extracted with ether (10×2 mL). The combined organic layers were washed with brine, dried over magnesium sulfate, filtered, and concentrated under reduced pressure to give crude product. Column chromatography on Florisil (1%–30% EtOAc/hexanes)

afforded the desired product as a solid. The material was further purified using HPLC. p-dimer 21 (13 mg, 0.019 mmol, 13%) was obtained after HPLC (silica, 25% EtOAc/hexanes, 3 mL/min, 254 nm, $R_t$=18.5 min) as a white solid: mp 87°–88° C.; $^1$H NMR (CDCl$_3$) δ8.02 (s, 4H), 5.33 (s, 2H), 5.11–5.06 (m, 2H), 3.20 (d ABq, Jd=5.6 Hz, $\Delta v_{AB}$=84.5 Hz, $J_{AB}$=16 Hz, 4H), 2.84–2.75 (m, 2H), 2.35–2.27 (m, 2H), 2.02–1.97 (m, 2H), 1.96–1.89 (m, 2H), 1.87–1.80 (m, 2H), 1.77–1.67 (m, 4H), 1.47–1.23 (m, 10H), 1.31 (s, 6H), 0.98 (d, J=6 Hz, 6H), 0.90 (d, J=7.6 Hz, 6H); $^{13}$C NMR (CDCl$_3$) δ197.58, 139.98, 128.39, 102.93, 89.56, 80.83, 70.00, 52.00, 44.01, 40.50, 37.54, 36.51, 34.41, 29.92, 25.80, 24.79, 20.11, 12.97; HRMS (CI) m/z calculated for $C_{40}H_{58}NO_{10}$ (M+NH$_4^+$) 712.4601, found 712.4054.

Example II

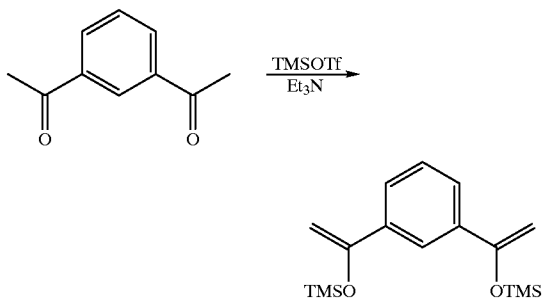

To a stirred solution of diacetylbenzene (1 eq.), ether and THF at room temperature was added triethylamine (2.2 eq.) via gas-tight syringe. Trimethylsilyl trifluoromethanesulfonate (TMSOTf; 2.2 eq.) was slowly added to the reaction mixture at room temperature via gas-tight syringe. The resulting mixture was stirred at room temperature for 2 hours.

The two layers were separated, and the top layer was concentrated under reduced pressure. The mixture was diluted with dry ether (30 mL) and filtered. The resulting filtrate was concentrated under reduced pressure to provide crude product as light yellow oil. Purification by Kügelrohr afforded the desired product that was used immediately for coupling with β-artemether. bis-TMS-enol ether of 1,3-diacetylbenzene (1.80 g, 5.87 mmol, 59% yield) was obtained as a colorless oil: $^1$H NMR (CDCl$_3$) δ7.83–7.82 (m, 1H), 7.53–7.50 (m, 2H), 7.29–7.25 (m, 1H), 4.93 (d, J=1.6 Hz, 2H), 4.44 (d, J=1.6 Hz, 2H), 0.27 (s, 18H); $^{13}$C NMR (CDCl$_3$) δ155.49, 137.27, 127.78, 125.06, 122.10, 91.18, 0.13.

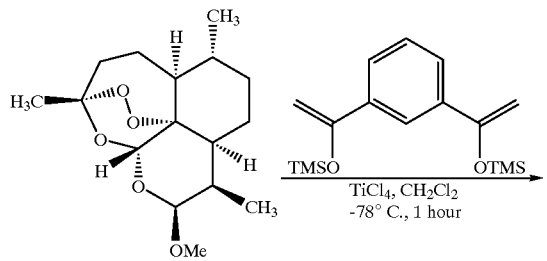

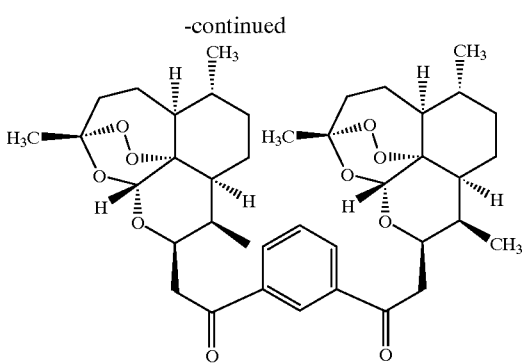

To a stirred solution of β-artemether (1 eq.) in CH$_2$Cl$_2$ at −78° C. added a 1M solution of TiCl$_4$ in CH$_2$Cl$_2$ (1.1 eq.) via gas-tight syringe. A solution of the bis-TMS-enol ether (0.55 eq.) in CH$_2$Cl$_2$ at room temperature was then added to the reaction mixture via gas-tight syringe. The resulting reaction mixture was stirred at −78° C. for 1 hour.

The reaction was quenched at −78° C. with water (3 mL) and diluted with ether (5 mL). The two layers were separated, and the aqueous phase was extracted with ether (10×2 mL). The combined organic layers were washed with brine, dried over magnesium sulfate, filtered, and concentrated under reduced pressure to give crude product. Column chromatography on Florisil (1%–30% EtOAc/hexanes) afforded the desired product as a solid. The material was further purified using HPLC. m-dimer 22 (45 mg, 0.065 mmol, 33%) was obtained after HPLC (silica, 25% EtOAc/hexanes, 3 mL/min, 254 run, $R_t$=19.4 min) as a white solid: mp 78°–79° C.; $^1$H NMR (CDCl$_3$) δ8.52–8.50 (m, 1H), 8.15–8.13 (m, 2H), 7.59–7.54 (m, 1H), 5.34 (s 2H), 5.11–5.05 (m, 2H), 3.11 (d ABq, Jd=6.4 Hz, $\Delta v_{AB}$=93.4 Hz, J AB=16.4 Hz, 4H), 2.86–2.77 (m, 2H), 2.34–2.26 (m, 2H), 2.02–1.97 (m, 2H), 1.96–1.89 (m, 2H), 1.86–1.82 (m, 2H), 1.73–1.67 (m, 4H), 1.45–1.22 (m, 10H), 1.30 (s, 6H), 0.97 (d, J=6 Hz, 6H), 0.91 (d, J=8 Hz, 6H); $^{13}$C NMR (CDCl$_3$) δ197.28, 137.15, 132.37, 128.93, 102.99, 89.40, 80.82, 70.17, 52.04, 44.11, 40.00, 37.45, 36.49, 34.40, 29.88, 25.81, 24.76, 20.11, 13.07; LRMS (CI, rel intensity) 712 (M+NH$_4$+, 1), 620 (28), 446 (37), 400 (97), 383 (100), 369 (28), 365 (95), 284 (30), 270 (28), 222 (14), 183 (17); HRMS (CI) m/z calculated for $C_{40}H_{58}NO_{10}$(M+NH$_4^+$) 712.4061, found 712.4069.

Example III

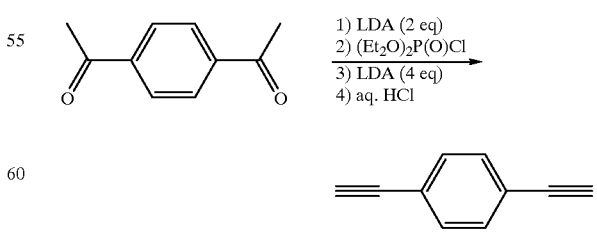

A 100 mL round-bottomed flask was charged with THF (55 mL) and lithium diisopropylamide (LDA; 1.5M in cyclohexane, 8.70 mL, 12.9 mmol, Aldrich) at −78° C. To this mixture was added a solution of 1,4-diacetylbenzene (1.00 g, 6.17 mmol, Aldrich) in THF (10 mL) at −78° C. The resulting yellow slurry was stirred at −78° C. for 1 hour. Diethyl chlorophosphate (1.96 mL, 13.6 mmol, Aldrich) was then added to the mixture via syringe. The resulting orange-brown mixture was stirred at −78° C. for 15 minutes and then slowly warmed up to room temperature and stirred for 15 minutes.

To a solution of LDA (18.5 mL, 27.8 mmol) in THF (60 mL) at −78° C. was added the above orange-brown mixture via cannula. The resulting dark blue-green reaction mixture was stirred at −78° C. for 40 minutes and slowly warmed up to room temperature. The reaction was monitored by thin layer chromatography until all starting material diketone was consumed (3.5 hours at room temperature).

The reaction was quenched with 1N HCl (3 mL) and diluted with water (25 mL). Two layers were separated and the aqueous was extracted with ether (25 mL×2). The combined organic layers were washed with 1N HCl (25 mL), water (25 mL) and saturated $NaHCO_3$ (25 mL). The organic phase was dried over $MgSO_4$, filtered and concentrated under reduced pressure to give a crude product. Column chromatography on silica (flash, 1% EtOAc/hexanes) afforded 1, 4 diethynylbenzene (0.620 g, 4.91 mmol, 80%) as a white crystalline solid: —mp 91–92° C. (lit. 96.5° C.) With $^1H$ and $^{13}C$ NMR spectra identical to those reported in the literature.

The reaction was quenched with water (3 mL) and diluted with ether (10 mL). Two layers were separated and the aqueous was extracted with ether (10 mL×2). The combined organic layers were washed with brine, dried over $MgSO_4$, filtered, and concentrated under reduced pressure to provide a crude product. Purification by column chromatography (Florisil®, 1%→5% ethyl acetate/hexanes) gave dimer 28 (0.010 g, 0.015 mmol, 15%) as a white solid: $^1H$ NMR ($CDCl_3$) δ7.34 (s, 4 H), 5.62 (s, 2 H), 4.96 (d, J=5.6 Hz, 2H), 2.85 (m, 2H, 2.38 (ddd, J=14.4, 13.6, 4.0 Hz, 2 H), 2.19 (apparent dq, Jd=3.3 Hz, Jq=13.6 Hz, 2 H, 2.06 (m, 2 H), 1.92–1.78 (m,6 H, 1.70–1.51 (m, 6 H), 1.45 (s, 6 M, 1.42–1.25 (m, 4 M, 1.04 (d, JI=7.6 Hz, 6 H), 0.96 (d, J=6.4 Hz, 6 H), $^{13}$ C NMR (CDCl3) δ131.4, 122.7, 104.3, 89.6, 88.9, 88.3, 80.9, 67.8, 52.7, 45.4, 37.4, 36.3, 34.6, 30.3, 26.1, 24.6, 23.0, 20.3, 13.9.

Example IV

Preparation of C-10 carbon-substituted Dimer 26 of the Present Invention a) Preparation of 10α-(1',3'-Dimethoxyphenyl) deoxoartemisininin

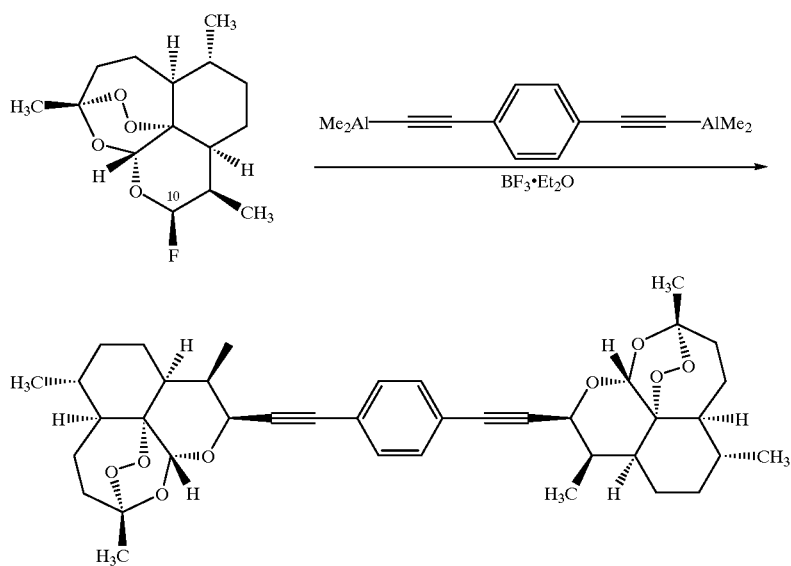

A 10 mL round-bottomed flask was charged with 1,4-diethynylbenzene (0.013 g, 0.1 mmol) and ether (1 mL) at 0° C. To this mixture was added n-BuLi (1.6M in hexanes, 0.13 mL, 0.21 mmol, Aldrich). The resulting white slurry was stirred at 0° C. for 30 minutes. Dimethyl aluminum chloride (1.0M in hexanes, 0.21 mL, 0.21 mmol, Aldrich) was then added to the reaction mixture at 0° C. The resulting yellowish mixture was stirred at 0° C. for 0.5 hours. To this reaction mixture at −78° C. was added boron trifluoride diethyl etherate ($BF_3 \cdot Et_2O$; 0.027 mL, 0.21 mmol, Aldrich) and a solution of C-10 β-fluorodeoxoartemisinin (0.060 g, 0.21 mmol) in $CH_2Cl_2$ (2 mL). The reaction mixture was stirred at −78° C. for 30 minutes, slowly warmed up to −50° C. and stirred for 2 hours. The reaction was finally warmed up to −40° C. and stirred for 12 hours.

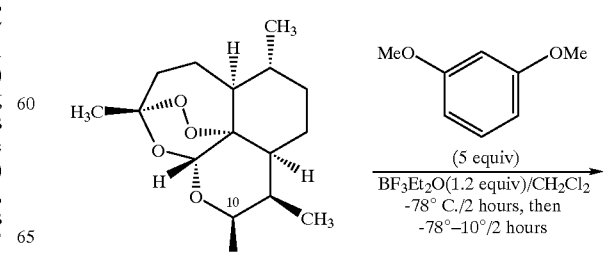

37

-continued

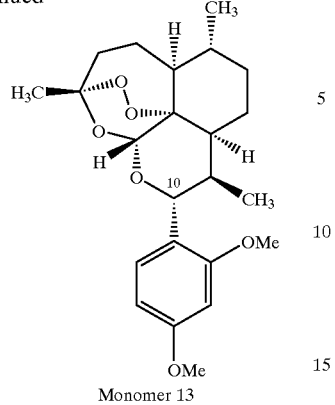

Monomer 13

38

-continued

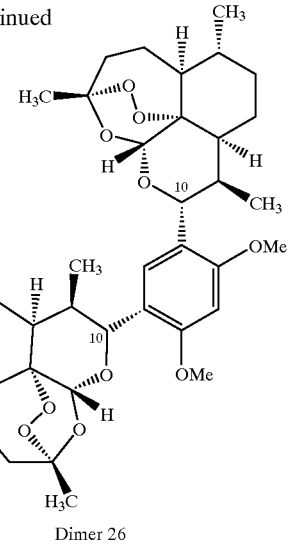

Dimer 26 b) Preparation of 1,3-Dimethoxybezene dimer 26

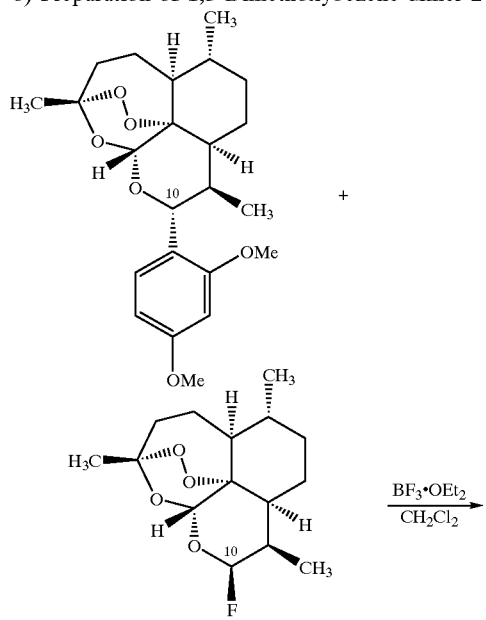

10α-(1',3'-Dimethoxyphenyl)deoxoartemisinin monomer 13 (64.6 mg, 0.16 mmol, 2 equiv) and the 10-deoxoartemisinin β-fluoride (22.9 mg, 0.08 mmol) wer dissolved in dry $CH_2Cl_2$ (0.8 mL) and cooled to −78° C. $BF_3Et_2O$ (14 μL, 0.11 mmol) was then added, and the mixture was stirred at −70° C. for 1 hour and then allowed to warm to −40° C. over 1 hour. After being stirred at this temperature for additional 4 hours, the reaction was quenched with saturated aqueous $NaHCO_3$ solution (1 mL) and then diluted with $CH_2Cl_2$ (10 mL) and water (5 mL). The organic phase was separated, and aqueous phase was extracted with $CH_2Cl_2$ (10 mL×2). The organic portion was combined, washed with water, dried over anhydrous $MgSO_6$, filtered, and concentrated under reduced pressure. Purification by column chromatography (flash gel, 33% EtOAc/hexanes) gave the desired 1,3-dimethoxybenzene dimer 26 (39.8 mg, 0.059 mmol, 74%) as a white solid. m.p.=168–169.2° C.; $^1H$ NMR (300 MHz, $CDCl_3$) δ7.91 (br s, 1H), 6.31 (s. 1H), 5.39 (s. 2H), 4.91 (d, J =9.9 Hz, 2H), 3.76 (s, 6H), 2.56 (m, 2H), 2.33 (m, 2H, 1.99 (m, 2H), 1.89–0.88 (m, 18H), 1.43 (s. 6H), 0.95 (d,J=6.2 Hz, 6H), 0.58 (s. 6H), $^{13}C$ NMR (75MH$_2$, $CDCl_2$) δ157.14, 127.8, 122.8, 104.4, 94.2, 92.4, 80.6, 70.0, 56.1, 52.5, 46.8, 37.3, 36.9, 34.8, 34.8, 26.4, 25.3, 22.0, 20.8, 13.0; IR(KBr) 2934, 2868, 1608, 1509, 1457, 1377, 1294, 1201, 1068, 883, 847 cm$^{-1}$. Note: The α,α-stereochemistry of anomeric centers was assigned based upon the proton NMR coupling constant ($J_{9\,10}$=9.9 Hz).

Example V

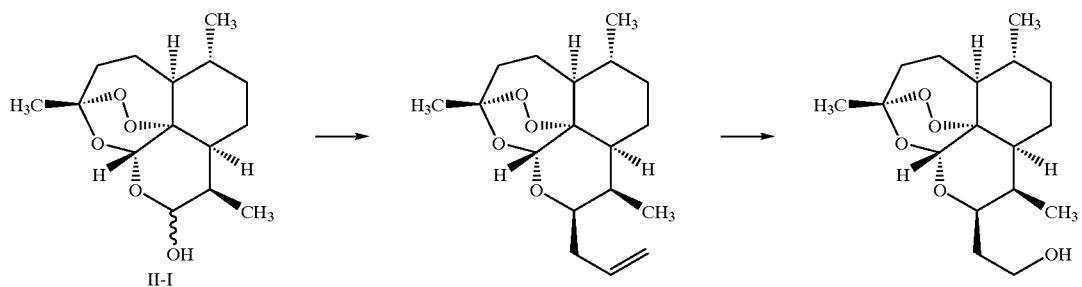

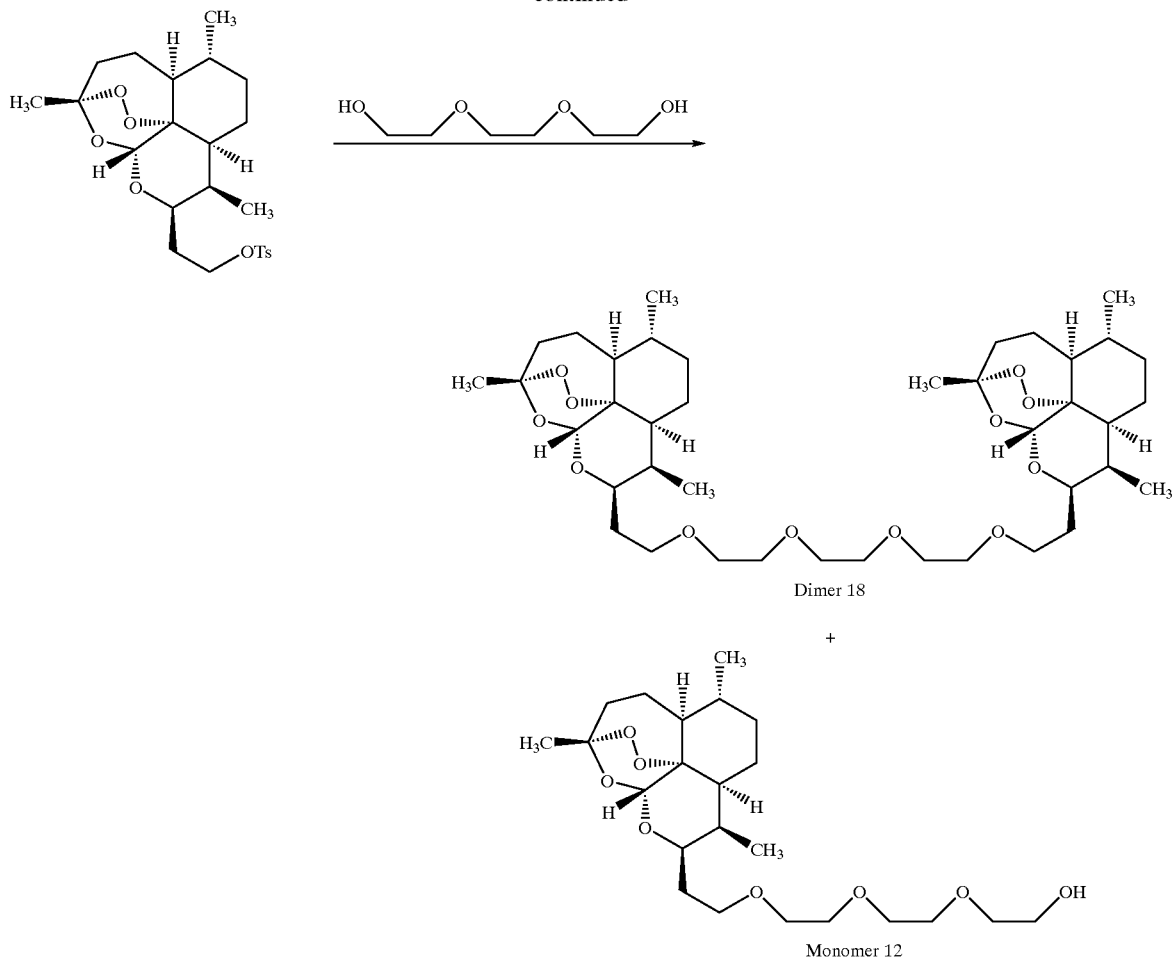

Dimer 18

+

Monomer 12

Compound dihydroartemisinin (II-1) was treated with trimethylallylsilane, $BF_3 \cdot Et_2O$ to form 10-β allyldeoxoartemisinin. 10-β allyldeoxoartemisinin was then converted to 10-β hydroxyethylartemisinin via oxidation ($O_3$) and reduction ($LiBH_4$). TsCl will then be reacted with this alcohol to form a tosylate. Triethylene glycol (TEG) is reacted with this tosylate to form dimer 18 (ββ) and monomer 12.

Example VI

Preparation of the Pyranosyl Fluoride Intermediate used to Form C-10 Carbon-substituted Derivatives of the Trioxane 10-deoxoartemisinin of the Present Invention A representative fluorination is as follows:

A 250 mL flame-dried round-bottomed flask was charged with dihydroartemisinin (II-I, 1.30 g, 4.57 mol) and dry tetrahydrofuran (100 mL). To this mixture at −30° C. was added diethylaminosulfur trifluoride (DAST, 1.34 mL, 6.82 mmol). The resulting reaction mixture was stirred at −30° C. for 15 minutes, slowly warmed up to room temperature and stirred for 1 hour. The reaction was concentrated under reduced pressure. The crude product was purified immediately without aqueous workup by column chromatography (Florisil®, 1%→5% ethyl acetate/hexanes) to give 10β-fluoride VI (1.08 g, 3.75 mmol, 82%) and 10α-fluoride (0.012 g, 0.366 mmol, 8%) as white solids.

10β-fluoride VI: mp=108.0–109.0° C.; $^1H$ NMR (300 MHz, $CDCl_3$) δ5.60 (dd, $J_{H-F}$=54.4 Hz, $J_{H-H}$=2.3 Hz, 1H), 5.56 (d, $J_{H-F}$=1.9 Hz, 1H), 2.63 (d of m, $J_{H-F}$=33.3 Hz, 1H), 2.38 (m, 1 H), 2.03 (m, 1 H), 1.93–1.80 (in, 2 H), 1.73–1.21 (in, 7 H), 1.43 (s, 3 H), 1.00 (d, J=7.4 Hz, 3 H), 0.96 (d, J=6.2 Hz, 3 H); $^{13}C$ NMR (75 MHz, $CDC_{13}$) δ111.2 (d, $J_{C-F}$=223 Hz), 104.9, 89.1, 80.9, 52.6, 43.8 (d, $J_{C-F}$=1.8 Hz), 37.8, 36.6, 34.9, 31.1 (d, $J_{C-F}$=22.7 Hz), 26.2, 25.0, 24.6 (d, $J_{C-F}$=5.9 Hz), 20.6, 12.7; $^{19}F$ NMR (282 MHz, $CDC_{13}$, $CFC_{13}$ (ex)) φ134.7 (dd, J=53.7, 36.7 Hz); IR (KBr) 2947, 2871, 1453, 1381, 1181, 11, 1040, 982, 950, 914, 867 $cm^{-1}$.

10α-fluoride: mp=99.0–100.0° C.; $^1H$ NMR (300 MHz, $CDCl_3$) δ5.44 (s, 1H), 5.27 (dd, $J_{H-F}$ =53.6 Hz, $J_{H-H}$–9.1 Hz, 1 H), 2.53 (m, 1 H), 2.40 (n, 1 H), 2.03 (m, 1 H), 1.94–1.05 (m, 9 H), 1.46 (s, 3 H), 0.99 (d, J=7.1 Hz, 3 H), 0.96 (d, J=7.1 Hz, 3 H); 13C NMR (75 MHz, CDCl3) δ108.8 (d, $J_{C-F}$=209 Hz), 105.0, 91.7 (d. $J_{CH-F}$=5.8 Hz), 80.2, 51.7, 45.4 (d, $J_{C-F}$ 9.6 Hz), 37.7, 36.5, 34.5, 33.2 (d, $J_{C-F}$=19.0 Hz), 26.2, 25.0, 22.5, 20.6, 12.0; $^{19}F$ NMR (282 MHz, $CDCl_3$, $CFCl_3$ (ex)) φ-140.7 (ddd, J=53.7, 10.8, 4.6 Hz); IR (KBr) 2946, 2880, 1456, 1380, 1205, 1111, 1042, 878, 846 $cm^{-1}$.

Example VII

Preparation of C-10 Carbon-Substituted Monomer 9 of the Present Invention

10β-(4'-Chlorophenylethynyl) deoxoartemisinin: 4-Chlorophenylacetylene (0.520 g, 3.84 mmol) was dissolved in dry diethyl ether (10 mL) and the solution was cooled to −78° C. Methyllithium (1.4M in diethyl ether, 2.49 mL, 3.49 mmol) was added slowly by syringe. The clear solution was warmed to 0° C. and stirred for 30 min. Dimethyl aluminum chloride (1.0M in hexanes, 3.49 mL, 3.49 mmol) was added slowly by syringe. The resulting cloudy white suspension was stirred at 0° C. for 30 minutes. The reaction was then cooled to −78° C. 10β-Fluorodeoxoartemisinin (0.500 g, 1.75 mmol) in dry dichloromethane (50 mL) at −78° C. was added by cannula. Boron trifluoride diethyl etherate (0.300 g, 2.10 mmol) was added slowly by syringe. The reaction was warmed to −50° C. and stirred for 3 hours. Distilled water (50 mL) was added and the separated aqueous phase was extracted with dichloromethane (3×50 mL). The combined organic solution was dried over magnesium sulfate and concentrated under vacuum. The remaining oil was purified by column chromatography (Florisil®, 5% ethyl acetate/hexanes) to provide monomer 9 (0.588 g, 1.46 mmol, 83%) as a colorless oil $[\alpha]^{25}_D$=+64.5 (c=1.33, CHCl$_3$). HPLC: 10:90 ethyl acetate: hexanes, 3 mL/min., R$_t$=12.1 min. $^1$H NMR (CDCl$_3$ 400 Mhz) δ7.27–7.34 (4H, m), 5.64 (1H, s), 4.96 (1H, d, J=5.6 Hz), 2.85 (1H, m), 2.38 (1H, ddd, J=4.0, 13.2, 14.4 Hz), 2.19 (1H, ddd, J=3.2, 13.6, 13.6 Hz) 2.06 (1H, dd, J=2.8, 4.8, 14.4, Hz), 1.78–1.94 (2H, m), 1.45 (3H, s, 1.20–1.72 (6H, m), 1.04 (3H, d, J=7.2 Hz), 0.96 (3H, d, J=6.0 Hz). $^{13}$C NMR (CDCl$_3$, 100 MHz) δ134.4, 132.6, 128.6, 121.1, 104.2, 89.5, 87.9, 87.6, 80.9, 67.8, 52.6, 45.3, 37.4, 36.2, 34.6, 30.3, 26.1, 23.0, 20.3, 13.9, IR (neat): 2940, 1488, 1377, 1227, 1188, 1089, 1052, 1014, 990, 960, 924, 873, 825 cm$^{-1}$.

Example VIII

Preparation of C-10 Carbon Substituted Monomer 15 of the Present Invention

A flame-dried 10 mL round-bottomed flask was charged with 2,7-dimethoxynaphthalene (0.113 g, 0.601 mmol) and β fluoride VI (0.034 g, 0.119 mmol) in dried dichloromethane (1 mL). To this mixture at −78° C. was added boron trifluoride diethyl etherate (0.018 mL, 0.143 mmol) via gas-tight syringe. The mixture turned bright yellow and then dark orange in 20 minutes at −78° C. The reaction mixture was stirred at −78° C. for 1 hour. TLC indicated no starting material fluoride. The reaction was quenched at −78° C. with distilled water (2 mL) and diluted with chloroform (4 mL). The two layers were separated and the aqueous phase was extracted with chloroform (4 mL×3). The combined organic layers were washed with brine (2 mL), dried over magnesium sulfate, filtered, and concentrated under reduced pressure. The crude product was purified by column chromatography (flash gel, 1%@5% ethyl acetate/hexanes) to give the monomer 15 (0.044 g, 0.095 mmol, 80%) with $^1$H NMR similar to that of subsequent material after HPLC.

Further purification by HPLC (silica, 15% ethyl acetate/hexanes, 3.0 mL/min, 264 nm, room temperature=11.1 min) afforded white solid 10α-(2',7'-dimethoxynaphth-3'-yl)deoxoartemisinin monomer 15: mp=149.0–151.0° C.; $[\alpha]_D^{25}$=+246.4° C. (c=1.29, CHCl$_3$); $^1$H NMR (400 MHz, CDCl$_3$) δ8.39 (d, J=2.4 Hz, 1 H), 7.67 (d, J=8.8 Hz, 1 H), 7.62 (d, J=8.8 Hz, 1 H), 7.05 (d, J =2.4 Hz, 1 H), 6.99 (dd, J=8.8, 2.4 Hz, 1 H), 5.69 (d, J=11.2 Hz, 1 H), 5.50 (s, 1 H), 4.02 (s, 3 H), 3.90 (s, 3 H), 3.38 (m, 1 H), 2.43 (apparent dt, J=4.0, 14.0 Hz, 1 H), 2.09 (ddd, J=16.0, 4.0, 2.8 Hz, 1 H), 1.94 (m, 1 H), 1.82–1.54 (m, 7 H), 1.44 (s, 3 H), 1.35 (m, 1 H), 1.02 (d, J=6.4 Hz, 3 H), 0.47 (d, J=7.2 Hz, 3 H); $^{13}$C NMR (100 MHz, CDCl$_3$) δ157.8, 155.3, 134.0, 129.52, 129.48, 125.4, 119.3, 116.9, 110.2, 104.6, 104.1, 93.0, 81.3, 70.2, 56.7, 56.1, 52.4, 46.3, 37.4, 36.4, 34.3, 30.4, 26.2, 24.8, 21.3, 20.4, 13.2; IR (CHCl$_3$) 3011, 2930, 2883, 1627, 1248, 1216, 1210, 1043, 784, 768, 748; cm$^{-1}$ analysis calculated for C$_{27}$H$_{34}$O$_6$: C 71.34, H7.54, found: C 71.27, H 7.52.

Example IX

Preparation of C-10 Carbon Substituted Monomer 16 of the Present Invention

β fluoride VI (0.400 g, 1.40 mmol) and N-methylpyrrole (0.568 g, 7.00 mmol) were dissolved in dry dichloromethane (25 mL) and the solution was cooled to −78° C. Boron trifluoride diethyl etherate (0.238 g, 0.206 mL, 1.68 mmol) was added slowly by syringe. Teh reaction was stirred for 30 minutes at −78° C. and then the temperature was raised to −40° C. After 5 hours at −40C, the reaction was quenched with distilled water (10 mL). The aqueous phase was separated and extracted with dichloromethane (10 mL×2). The combined organic solution was dried over magnesium sulfate and concentrated under reduced pressure. The resulting oil was purified by column chromatography (Florisil®, 10% ethyl acetate/hexanes) to provide the product (0.417 g, 1.20 mmol, 86%) 10α-(N-methylpyrrol-2'-yl)deoxoartemisinin monomer 16 as a white foam: $[\alpha]_D^{25}$=+105.8° (c=1.65, CHCl$_3$); HPLC: silica, 10% ethyl acetate/hexanes, 3 mL/min, 254 nm, Rt=12.5 min; $^1$H NMR (400 MHz, CDCl$_3$) δ6.55 (dd, J=2.0, 2.4 Hz, 1 H), 6.00–5.97 (in, 2 H), 5.39 (s, 1 H), 4.50 (d, J=11.2 Hz, 1 H), 3.84 (s, 3 H), 2.90–2.78 (m, 1 H), 2.39 (dt, J=4.0, 14.0 Hz, 1 H), 2.04 (ddd, J=14.4, 4.8, 2.8 Hz, 1 H), 1.94–1.87 (m, 1 H), 1.40 (s, 3 H), 0.99 (d, J=6.4 Hz, 3 H), 1.80–0.80 (in, 8 H), 0.61 (d, J=7.2 Hz, 3 H); $^{13}$C NMR (100 MHz, CDCl$_3$) δ129.6, 123.6, 109.4, 106.0, 104.0, 91.8, 80.6, 72.4, 51.9, 45.8, 37.3, 36.2, 35.0, 34.1, 30.8, 26.0, 24.7, 20.9, 20.3, 14.3; IR (CHCl$_3$) 2927, 1454, 1377, 1321, 1042, 927, 880, 828, 711 cm$^{-1}$.

The foregoing description is considered as illustrative only of the principles of the invention. Furthermore, since numerous modifications and changes will readily occur to those skilled in the art, it is not desired to limit the invention to the exact construction and processes shown as described above. Accordingly, all suitable modifications and equivalents may be resorted to falling within the scope of the invention as defined by the claims which follow.

What is claimed is:

1. A compound of formula:

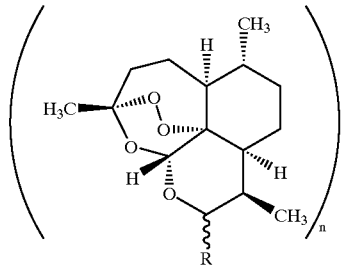

and the enantiomers and diastereomers thereof, wherein:

a.) n is 1, and R is selected from the group consisting of acetylenic, polyethylene glycol, aroylmethylene, or alkanoylmethylene group.

2. The compound according to claim 1, wherein n is 1 and R is selected from the group consisting of:

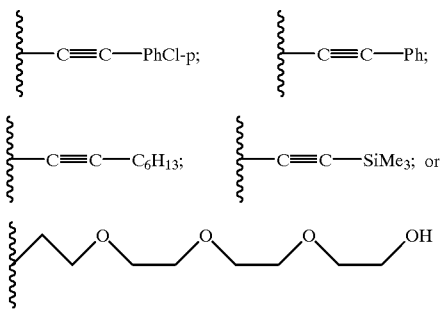

3. A compound of formula:

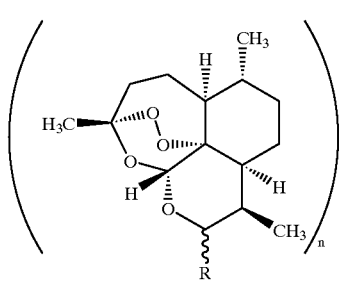

and the enantiomers and diastereomers thereof, wherein:

n is 2, and R is selected from the group consisting of an unsubstituted or substituted aryl, heteroaryl, alkenyl, alkyl, diketone, polyethylene glycol, or bis-acetylene group.

4. The compound according to claim 3, wherein n is 2 and R is selected from the group consisting of:

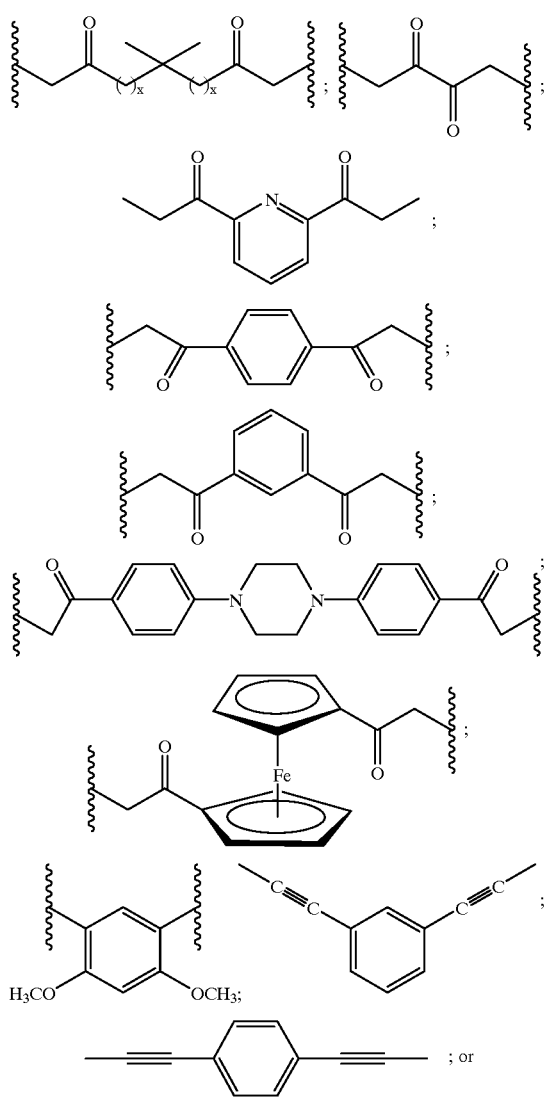

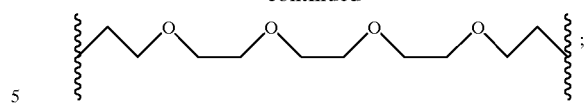

wherein x is 0–2.

5. A compound of formula:

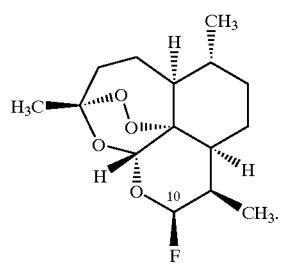

6. A method for treating cancer, which comprises administering to a patient suffering from said cancer a C-10 carbon-substituted trioxane of the formula:

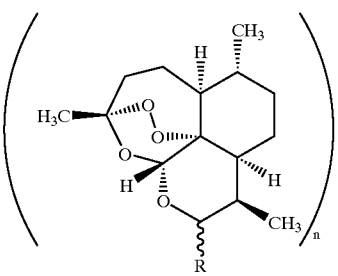

and the enantiomers and diastereomers thereof, wherein:

a.) n is 1, and R is selected from the group consisting of an unsubstituted or substituted aryl, heteroaryl, acetylenic, polyethylene glycol, aroylmethylene or alkanoylmethylene group; or b.) n is 2, and R is selected from the group consisting of an unsubstituted or substituted aryl, heteroaryl, alkenyl, alkyl, diketone, polyethylene glycol, or bis-acetylene group.

7. The method according to claim 6, wherein n is 1 and R is selected from the group consisting of:

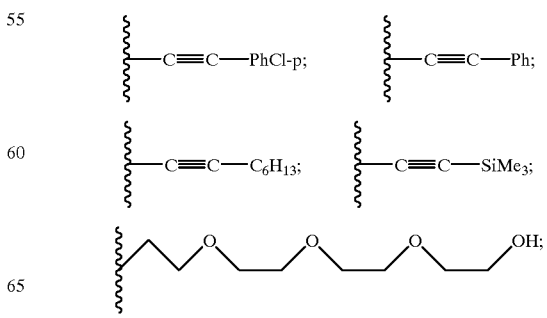

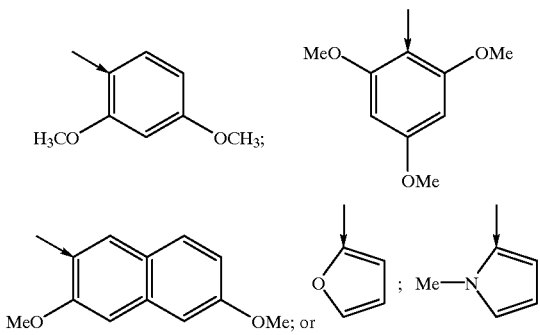

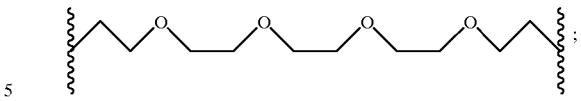

wherein, x is 0–2.

wherein ↓ designates the point of attachment.

8. The method according to claim 6, wherein n is 2 and R is selected from the group consisting of:

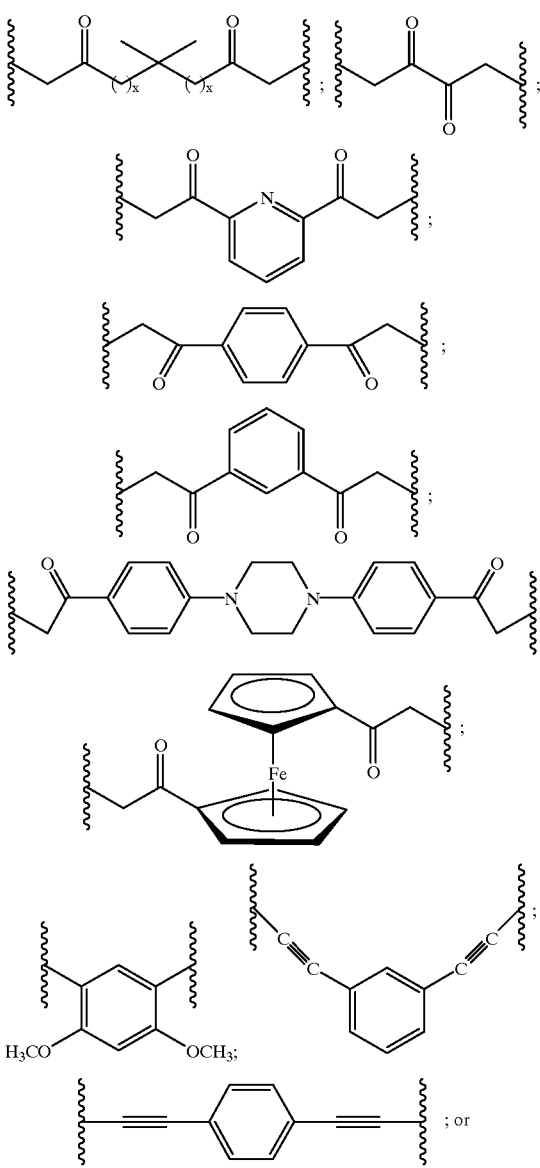

9. The method according to claim 6, wherein said cancer is selected from the group of cancers consisting of leukemia, non-small-cell lung cancer, colon cancer, central nervous system cancer, melanoma, ovarian cancer, renal cancer, protate cancer, and breast cancer.

10. The method according to claim 7, wherein said cancer is selected from the group of cancers consisting of leukemia, non-small-cell lung cancer, colon cancer, central nervous system cancer, melanoma, ovarian cancer, renal cancer, protate cancer, and breast cancer.

11. The method according to claim 8, wherein said cancer is selected from the group of cancers consisting of leukemia, non-small-cell lung cancer, colon cancer, central nervous system cancer, melanoma, ovarian cancer, renal cancer, protate cancer, and breast cancer.

12. A method for treating malaria, which comprises administering to a patient suffering from said malaria a C-10 carbon-substituted trioxane of the formula:

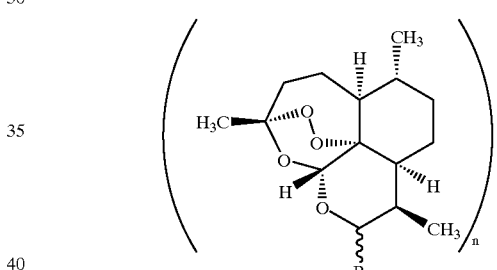

and the enantiomers and diastereomers thereof, wherein:

a.) n is 1, and R is selected from the group consisting of an acetylenic, polyethylene glycol, aroylmethylene, or alkanoylmethylene group.

13. The method according to claim 12, wherein n is 1 and R is selected from the group consisting of:

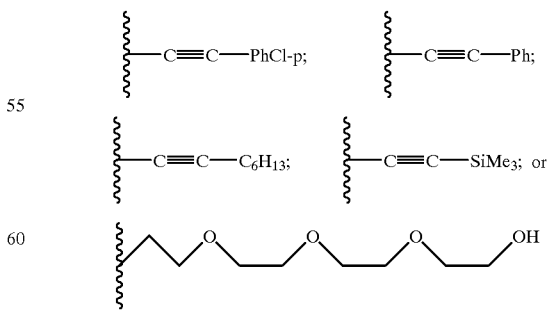

14. A method for treating malaria, which comprises administering to a patient suffering from said malaria a C-10 carbon-substituted trioxane of the formula:

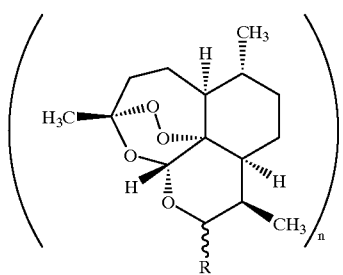

and the enantiomers and diastereomers thereof, wherein: n is 2, and R is selected from the group consisting of an unsubstituted or substituted aryl, heteroaryl, alkenyl, alkyl, diketone, polyethylene glycol, or bis-acetylene group.

15. The method according to claim 14, wherein n is 2 and R is selected from the group consisting of:

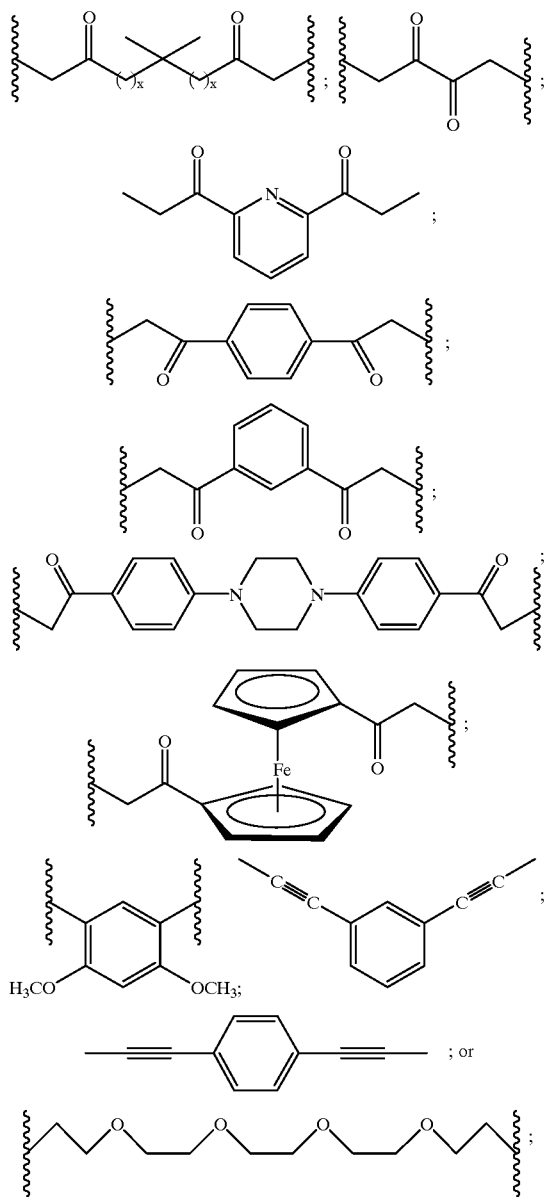

wherein x is 0–2.

16. A process for converting the pyranose anomeric 10-OH group in dihydroartemesinin with a carbon nucleophile comprising:

contacting dihydroartemisinin with diethylaminosulfur trifluoride to produce β pyranosyl fluoride;

purifying said β pyranosyl fluoride; and reacting said β pyranosyl fluoride with a carbon nucleophile.

17. A process for converting the pyranose anomeric 10-OH group in dihydroartemesinin with a carbon nucleophile comprising:

contacting dihydroartemisinin with an electron-rich aromatic or heteroaromatic nucleophile.

18. A process for converting the pyranose anomeric 10-OH group in dihydroartemesinin with a carbon nucleophile comprising:

contacting dihydroartemisinin with alcohol under acidic conditions to produce the corresponding C-10 ether;

reacting said C-10 ether with an enol derivative.

19. The process according to claim 18, wherein said enol derivative is bis-enol silyl ether.

20. The process according to claim 18, wherein said enol derivative is mono-enol silyl ether.

21. The process according to claim 18, wherein said alcohol is methanol and said corresponding C-10 ether is artmether.

22. The process according to claim 18, wherein said alcohol is ethanol and said corresponding C-10 ether is artmether.

23. A process for converting the 10-OMe group in artemether with a carbon nucleophile comprising:

reacing artemether with an enol derivative.

24. The process according to claim 17, wherein said enol derivative is bis-enol silyl ether.

25. The process according to claim 17, wherein said enol derivative is mono-enol silyl ether.

26. A method of treating cancer, which comprises administering to a patient suffering from said cancer a compound of formula:

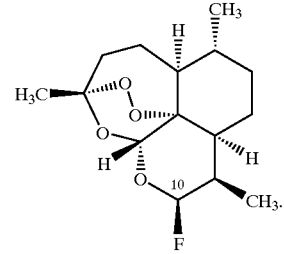

27. The method according to claim 26, wherein said cancer is selected from the group of cancers consisting of leukemia, non-small-cell lung cancer, colon cancer, central nervous system cancer, melanoma, ovarian cancer, renal cancer, prostate cancer, and breast cancer.

28. A method of treating a disease resulting from the profliferation of cells comprising subjecting said proliferative cells to a compound of formula:

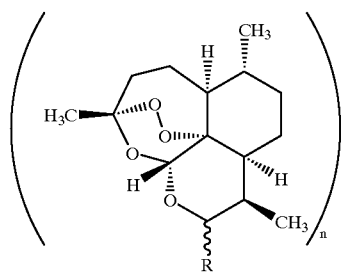

and the enantiomers and diastereomers thereof, wherein:
  a.) n is 1 and R is selected from the group consisting of an unsubstituted or substituted aryl, heteroaryl, acetylenic, polyethylene glycol, aroylmethylene or alkanoylmethylene group; or
  b.) n is 2, and R is selected from the group consisting of an unsubstituted or substituted aryl, heteroaryl, alkenyl, alkyl, diketone, polyethylene glycol, or bis-acetylene group.

29. The method according to claim 28, wherein n is 1 and R is selected from the gruop consisting of:

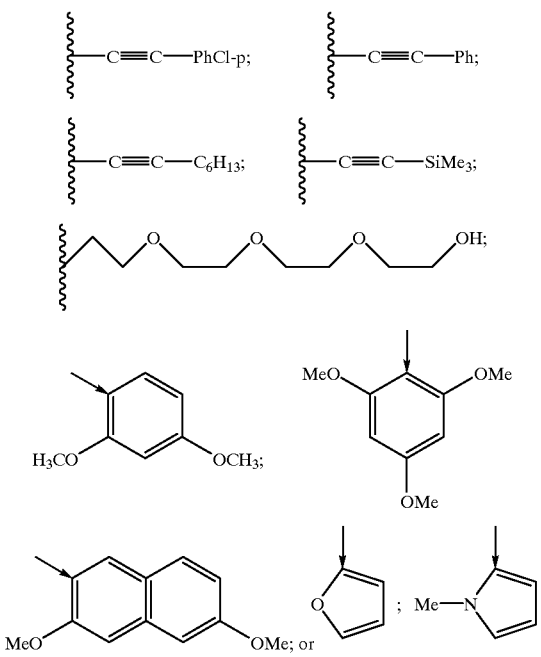

wherein ↓ designates the point of attachment.

30. The method according to claim 28, wherein n is 2 and R is selected from the group consisting of:

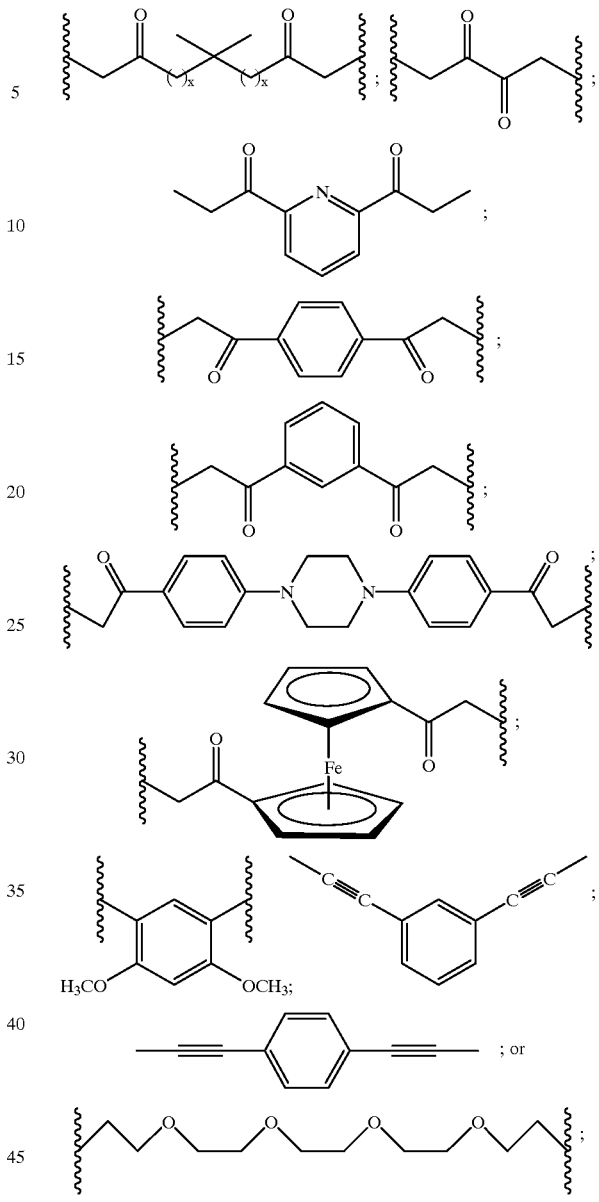

wherein, x is 0–2.

* * * * *